US010106502B2

(12) United States Patent
Hu et al.

(10) Patent No.: US 10,106,502 B2
(45) Date of Patent: Oct. 23, 2018

(54) DIRECT INHIBITORS OF KEAP1-NRF2 INTERACTION AS ANTIOXIDANT INFLAMMATION MODULATORS

(71) Applicants: Rutgers, The State University of New Jersey, New Brunswick, NJ (US); The Broad Institute, inc., Cambridge, MA (US)

(72) Inventors: Longqin Hu, Belle Mead, NJ (US); Sadagopan Magesh, Highland Park, NJ (US); Lin Chen, Piscataway, NJ (US); Timothy Lewis, Marlborough, MA (US); Ben Munoz, Netwonville, MA (US); Lili Wang, Chestnut Hill, MA (US)

(73) Assignees: RUTGERS, THE STATE UNIVERSITY OF NEW JERSEY, New Brunswick, NJ (US); THE BROAD INSTITUTE, INC., Cambridge, MA (US)

( * ) Notice: Subject to any disclaimer, the term of this patent is extended or adjusted under 35 U.S.C. 154(b) by 0 days.

(21) Appl. No.: 15/718,987

(22) Filed: Sep. 28, 2017

(65) Prior Publication Data

US 2018/0148408 A1 May 31, 2018

Related U.S. Application Data

(63) Continuation of application No. 15/463,728, filed on Mar. 20, 2017, which is a continuation of application No. 14/355,419, filed as application No. PCT/US2012/062833 on Oct. 31, 2012.

(60) Provisional application No. 61/553,318, filed on Oct. 31, 2011.

(51) Int. Cl.

| | |
|---|---|
| ***A01N 43/42*** | (2006.01) |
| ***A61K 31/44*** | (2006.01) |
| ***C07D 209/48*** | (2006.01) |
| ***A61K 31/472*** | (2006.01) |
| ***C07D 207/452*** | (2006.01) |
| ***C07D 405/12*** | (2006.01) |
| ***C07D 401/06*** | (2006.01) |
| ***C07D 335/06*** | (2006.01) |
| ***C07D 401/14*** | (2006.01) |
| ***G01N 33/50*** | (2006.01) |
| ***C07D 217/16*** | (2006.01) |
| ***A61K 31/4725*** | (2006.01) |

(52) U.S. Cl.

CPC .......... *C07D 209/48* (2013.01); *A61K 31/472* (2013.01); *A61K 31/4725* (2013.01); *C07D 207/452* (2013.01); *C07D 217/16* (2013.01); *C07D 335/06* (2013.01); *C07D 401/06* (2013.01); *C07D 401/14* (2013.01); *C07D 405/12* (2013.01); *G01N 33/5023* (2013.01)

(58) Field of Classification Search

None

See application file for complete search history.

(56) References Cited

U.S. PATENT DOCUMENTS

| | | | | |
|---|---|---|---|---|
| 4,362,875 | A | 12/1982 | Seubert | |
| 6,004,991 | A | 12/1999 | Fourtillan et al. | |
| 6,143,789 | A | 11/2000 | Lefoulon et al. | |
| 2007/0032517 | A1 | 2/2007 | Debenham et al. | |
| 2009/0042980 | A1 | 2/2009 | Lipton et al. | |
| 2009/0156605 | A1 | 6/2009 | Alien et al. | |
| 2009/0163545 | A1 * | 6/2009 | Goldfarb .............. | A61K 31/122 514/312 |
| 2010/0029012 | A1 | 2/2010 | Kern et al. | |
| 2011/0112196 | A1 | 5/2011 | Lukashev | |

OTHER PUBLICATIONS

Hu, Longqin: "The Prodrug Approach to Better Targeting", Meeting Report, Aug. 2004, pp. 28-32.

Blaisdell, Thomas: "Enantiomeric Separation of Racemic Drugs Using Chiral Self-Assembled Monolayers", A Major Qualifying Project Report Submitted to the Faculty of Worcester Polytechnic Institute, Apr. 29, 2010.

Goldfarb, David S.: Accession No. 2009:846108 Caplus, 2009.

Chen, et al., "Kinetic Analyses of Keapl-Nrf2 Interaction and Determination of the Minimal Nrf2 Peptide Sequence Required for Keapl Binding Using Surface Plasmon Resonance," Chem. Bioi. Drug Des. Dec. 2011, vol. 78, No. 6, pp. 1014-1021.

Christov, et al., "Integrated Synthetic, Pharmacological, and Computational Investigation of cis-2-(3,5-Dichlorophenylcarbamoyl)cyclohexanecarboxylic acid Enantiomers as Positive Allosteric Modulators of Metabotropic Glutamate Receptor Subtype?4," Chem Med Chem, Jan. 2011, vol. 6, No. 6, pp. 131-140.

Roskowski, et al., "Enantioselective Synthesis of (R)-(-)-praziquantel (PZQ)" Tetrahedron: Asymmetry, 2006, vol. 17, No. 9, pp. 1415-1419 (Abstract).

* cited by examiner

*Primary Examiner* — Jean P Cornet

(74) *Attorney, Agent, or Firm* — Fox Rothschild LLP

(57) ABSTRACT

A method of identifying compounds as direct inhibitors of Keap1-Nrf2 interaction through high-throughput screening and lead development. The direct inhibitors of Keap1-Nrf2 interaction are more specific and free of various undesirable effects than existing indirect inhibitors, and are potential drug candidates of chemopreventive and therapeutic agents for treatment of various diseases or conditions involving oxidative stress and/or inflammation, including but not limited to cancers, diabetes, Alzheimer's, and Parkinson's. Novel compounds are identified and methods of preventing or treating diseases or conditions related to Keap1-Nrf2 interaction activity by use of the novel compounds identified or compositions containing such compounds are also disclosed.

11 Claims, 17 Drawing Sheets

LH601D

[ISOMERS] nM

LH601B

LH601A

LH602

BRD-A69788832-001-06-6
LH601
IC50: 3uM

BRD-K09114961-001-03-6
IC50: 26uM

□ BRD-A697788832-001-06-6

□ BRD-K09114961-001-03-6

□ BRD-A697788832-001-06-6

□ BRD-K09114961-001-03-6

BRD-A09671526-001-05-0
LH602
IC50: 2.7uM

BRD-K91732811-001-06-9
IC50: 55uM

□ BRD-A0967 1526-001-05-0

□ BRD-A0967 1526-001-05-0

□ BRD-K91732811-001-06-9

BRD-K56215778-001-06-9
IC50: 37uM

BRD-K42553821-001-05-9
IC50: 91uM

□ BRD-K56215778-001-06-9

□ BRD-K42553821-001-05-9

□BRD-K56215778-001-06-9

□ BRD-K42553821-001-05-9

BRD-A83249228-001-07-1
IC50: 135uM

□ BRD-A83249228-001-07-1

□ BRD-A83249228-001-07-1

BRD-K11951445-001-04-1
IC50: 19uM

□ BRD-K11951445-001-04-1

DIRECT INHIBITORS OF KEAP1-NRF2 INTERACTION AS ANTIOXIDANT INFLAMMATION MODULATORS

CROSS-REFERENCE TO RELATED APPLICATIONS

This application is a continuation of U.S. patent application Ser. No. 15/463,728 filed Mar. 20, 2017, which is a continuation of U.S. patent application Ser. No. 14/355,419 filed Apr. 30, 2014, which is a U.S. national phase of International Application No. PCT/US12/62833 filed Oct. 31, 2012, which claims priority under 35 U.S.C. § 119(e) to U.S. Provisional Patent Application Ser. No. 61/553,318, filed on Oct. 31, 2011, which is hereby incorporated by reference in its entirety.

STATEMENT REGARDING FEDERALLY SPONSORED RESEARCH

The invention described herein was supported in whole or in part by grants from the National Institute of Health via Grant No. R03 MH093197 and No. R01 CA133791. The U.S. Government has certain rights in this invention.

FIELD OF THE INVENTION

The present invention relates to use of Keap1-Nrf2 protein-protein interaction as a target in discovery of drug candidates, and the discovery of small molecule direct inhibitors of Keap1-Nrf2 protein-protein interaction and potent activators of Nrf2 and ARE-mediated genes to modulate inflammatory processes.

BACKGROUND OF THE INVENTION

Inflammatory as well as normal physiological processes produce a host of harmful oxidizing substances such as reactive oxygen species (ROS), reactive nitrogen species (RNS), reactive electrophilic metabolites, and lipid peroxidation products. To protect against these harmful substances, the human body has developed intrinsic antioxidant response mechanisms to upregulate a number of antioxidative and cytoprotective enzymes that include glutathione S-transferases (GST), UDP-glucuronyl transferase 1A1 (UGT1A1), NAD(P)H:quinone oxidoreductase 1 (NQO1), catalase, superoxide dismutase 1 (SOD1), and heme oxygenase 1 (HO-1). There are three major cellular components involved in the regulation of antioxidant response; they are Kelch-like ECH-associated protein 1 (Keap1), nuclear factor erythroid 2-related factor 2 (Nrf2), and antioxidant response elements (ARE). The Keap1-Nrf2-ARE is the main signaling pathway that regulates a series of cytoprotective proteins at the transcriptional level including Nrf2 itself as shown in FIG. 1. This signaling pathway induces an adaptive response for oxidative stress which can otherwise lead to many inflammatory diseases. In fact, inflammation has been recognized as an underlying contributor to virtually every chronic disease. Thus, targeting the Keap1-Nrf2-ARE signaling pathway is an attractive strategy to discover preventive and therapeutic agents as antioxidant inflammation modulators (AIMs) for diseases and conditions, including cancer, diabetes, Alzheimer's, and Parkinson's, that involve oxidative stress and inflammation.

Some of the known Nrf2-ARE inducing agents are already in human clinical trials as chemopreventive agents for cancer or as therapeutic agents for conditions involving inflammation. For example, sulforaphane, an isothiocyanate found in cruciferous vegetables and a known ARE inducer, is being tested in clinical trials for the treatment and prevention of prostate cancer and for the treatment of chronic obstructive pulmonary disease (COPD). Bardoxolone methyl, another potent inducer of the Nrf2 pathway, was tested in phase III clinical trials as a first-in-class AIM for the treatment of advanced chronic kidney disease (CKD) in patients with type 2 diabetes mellitus. However, all currently known small molecule Nrf2/ARE inducers are believed to be irreversible modifying agents of cysteine sulfhydryl groups and these include many natural products (e.g., sulforaphane, curcumin, and epigallocatechin gallate from natural sources such as fruits, vegetables, and tea products) and synthetic compounds (e.g., oltipraz, anethole dithiolethione, bardoxolone methyl). All these compounds are either chemically reactive or can be converted to chemically reactive metabolites that readily oxidize or form covalent adduct with the sulfhydryl group of cysteines. It is believed that this modification of cysteine residues in Keap1 is responsible for the disruption of Keap1-Nrf2 complex formation and degradation, leading to subsequent translocation of Nrf2 into the nucleus. Thus, these known modulators are all considered indirect irreversible inhibitors of Keap1-Nrf2 interaction. The reactivity of these compounds raises safety concerns over their long-term use as chemopreventive and therapeutic agents. Development as such is questionable because of concerns about their long-term toxicity. Indeed, bardoxolone methyl was recently withdrawn from Phase III clinical trials citing safety concerns over adverse events and increased rate of death.

Direct disruption of Keap1-Nrf2 protein-protein interaction using small molecule inhibitors, though more challenging, represents an attractive novel strategy to promote translocation of Nrf2 to the nucleus and elevate the expression of ARE enzymes. The only direct inhibitors of Keap1-Nrf2 interaction currently known are the peptides based on the Nrf2 Neh domain that are used in the crystallographic studies. Multiple charges are present on these peptides and their poor membrane permeability and susceptibility to proteolysis prevented their use directly in cellular and in vivo assays. Therefore, there is an urgent need to discover potent small molecule direct inhibitors of Keap1-Nrf2 protein-protein interaction as proposed in this application.

SUMMARY OF THE INVENTION

The present invention is designed to meet the foregoing need, pertaining to use of Keap1-Nrf2 protein-protein interaction as a novel target in discovery of drug candidates, and the discovery of small molecule direct inhibitors of Keap1-Nrf2 protein-protein interaction as potent activators of Nrf2 and ARE-mediated genes to modulate inflammatory processes, in particular identification of lead compounds and development of useful drug candidates through modification and derivatization of these lead compounds to find suitable candidates for development into therapeutic agents.

These inhibitors are useful as pharmacological probes for the elucidation of the role of the important Keap1-Nrf2-ARE pathway in inflammation, a central theme in a variety of diseases and conditions. In addition, they can potentially be developed into chemopreventive and therapeutic agents for a variety of diseases and conditions including, but not limited to, cancer, diabetes, Alzheimer's, and Parkinson's.

Thus, in one aspect, the present invention provides a method of identifying lead or candidate compounds useful for developing small-molecule therapeutic agents for treatment of inflammatory diseases or conditions associated with Keap1-Nrf2 protein-protein interaction, the method comprising screening a plurality of compounds against a Keap1-Nrf2 interaction target using an assay selected from FP, TR-FRET, and SPR-based solution competition assays.

In another aspect, the invention provides methods of preventing or treating an inflammatory disease or disorder, comprising administering to a subject in need thereof a therapeutically effective amount of an agent that is a non-peptide small molecule direct inhibitor of Keap1-Nrf2 protein-protein interaction.

In one embodiment of this aspect, the invention provides a method of preventing or treating an inflammatory disease or disorder, comprising administering to a subject in need thereof a therapeutically effective amount of a compound of formula (I):

(I)

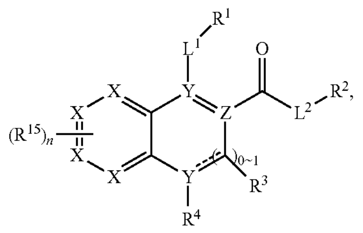

or a stereoisomer, a prodrug, or a pharmaceutically acceptable salt or solvate thereof, wherein:

"$\overline{\underline{\ \ }}$" at each occurrence is independently a single or double bond;

X at each occurrence is independently nitrogen (N) or carbon (C or CH);

Y at each occurrence is independently nitrogen (N) or carbon (C or CH);

Z is nitrogen (N) or carbon (C or CH);

$L^1$ is —$[C(R^{10})_2]_i$—, wherein $R^{10}$ at each occurrence is independently hydrogen, halogen, $C_1$-$C_4$ alkyl, or $C_1$-$C_4$ haloalkyl, and i is 0, 1, 2, or 3;

$L^2$ is —$[C(R^{20})_2]_j$—, $C_3$-$C_8$ cycloalkylene, $C_6$-$C_{10}$ arylene, 5- to 10-membered heteroarylene, or 5- to 10-membered heterocyclylene, each optionally substituted by one to three substituents independently selected from halogen, hydroxyl, $C_1$-$C_4$ alkyl, and $C_1$-$C_4$ haloalkyl, —$OR^9$, and —$NR^aR^b$, wherein $R^{20}$ at each occurrence is independently hydrogen, halogen, $C_1$-$C_4$ alkyl, or $C_1$-$C_4$ haloalkyl, and wherein j is an integer selected from 1 through 6;

$R^1$ is an amido or imido group, said amido or imido group comprising a group selected from unsubstituted or substituted $C_6$-$C_{10}$ aryls and unsubstituted or substituted 5- to 10-membered heteroaryls;

$R^2$ is selected from

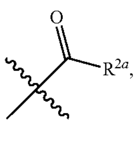

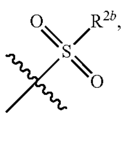

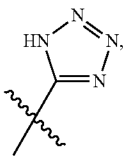

-continued

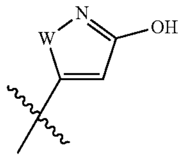

(W=O, S, or NH),

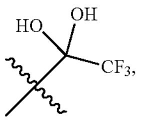

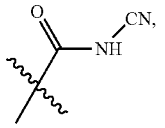

and

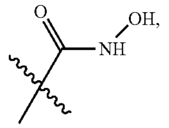

wherein $R^{2a}$ and $R^{2b}$ are each independently —$OR^9$ or —$NR^aR^b$;

$R^3$ and $R^4$ are each independently hydrogen, halogen, hydroxyl, $C_1$-$C_6$ alkyl, $C_1$-$C_6$ haloalkyl, $C_1$-$C_6$ alkoxy, $C_1$-$C_6$ haloalkoxy, $C_3$-$C_8$ cycloalkyl, $C_6$-$C_{10}$ aryl, 5- to 10-membered heterocyclyl, 5- to 10-membered heterocyclyl, —CN, nitro, —$COOR^{11}$, or —$NR^aR^b$;

$R^9$ at each occurrence is independently hydrogen, $C_1$-$C_6$ alkyl, $C_1$-$C_6$ haloalkyl, or benzyl;

wherein any said cycloalkyl or heterocyclyl is optionally substituted by one or more substituents independently selected from halogen, hydroxyl, $C_1$-$C_6$ alkyl, $C_1$-$C_6$ haloalkyl, $C_1$-$C_6$ alkoxy, $C_1$-$C_6$ haloalkoxy, —CN, nitro, oxo, —$COOR^{11}$, and —$NR^aR^b$;

each said aryl or heteroaryl is optionally substituted by one or more substituents independently selected from halogen, hydroxyl, $C_1$-$C_6$ alkyl, $C_1$-$C_6$ haloalkyl, $C_1$-$C_6$ alkoxy, $C_1$-$C_6$ haloalkoxy, —CN, nitro, —$COOR^{11}$, and —$NR^aR^b$;

$R^a$ and $R^b$ at each occurrence are independently hydrogen or $C_1$-$C_6$ alkyl;

$R^{11}$ at each occurrence is independently hydrogen, $C_1$-$C_6$ alkyl, or benzyl;

$R^{15}$ at each occurrence is independently hydrogen, halogen, hydroxyl, $C_1$-$C_6$ alkyl, $C_1$-$C_6$ haloalkyl, $C_1$-$C_6$ alkoxy, $C_1$-$C_6$ haloalkoxy, —CN, nitro, —$COOR^{11}$, —$CONR^aR^b$, and —$NR^aR^b$; and n at each occurrence is independently 0 or an integer selected from 1 to 4.

In another embodiment of aspect, the invention provides a method of preventing or treating an inflammatory disease or disorder, comprising administering to a subject in need thereof a therapeutically effective amount of a compound of formula (II):

(II)

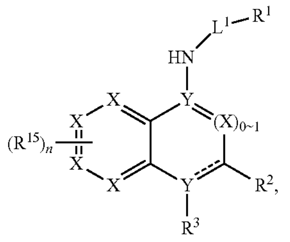

or a stereoisomer, a prodrug, or a pharmaceutically acceptable salt or solvate thereof, wherein:

"$\overline{\underline{\ \ }}$" at each occurrence is independently a single or double bond;

X at each occurrence is independently nitrogen (N) or carbon (C or CH);

Y at each occurrence is independently nitrogen (N) or carbon (C or CH);

$L^1$ is 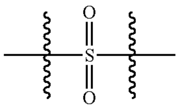 or 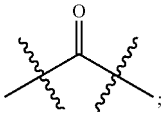;

$R^1$ is selected from unsubstituted or substituted $C_6$-$C_{10}$ aryls and unsubstituted or substituted 5- to 10-membered heteroaryls;

$R^2$ is

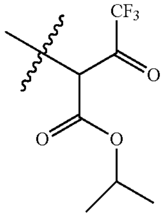 [SMILES: *C(C(=O)OC(C)C)C(=O)C(F)(F)F]

or a bioisosteric group thereof;

$R^3$ is hydrogen, halogen, hydroxyl, $C_1$-$C_6$ alkyl, $C_1$-$C_6$ haloalkyl, $C_1$-$C_6$ alkoxy, $C_1$-$C_6$ haloalkoxy, —$COOR^{11}$, or —$NR^aR^b$;

wherein any said cycloalkyl, or heterocyclyl is optionally substituted by one or more substituents independently selected from halogen, hydroxyl, $C_1$-$C_6$ alkyl, $C_1$-$C_6$ haloalkyl, $C_1$-$C_6$ alkoxy, $C_1$-$C_6$ haloalkoxy, —CN, nitro, oxo, —$COOR^{11}$, and —$NR^aR^b$;

each said aryl or heteroaryl is optionally substituted by one or more substituents independently selected from halogen, hydroxyl, $C_1$-$C_6$ alkyl, $C_1$-$C_6$ haloalkyl, $C_1$-$C_6$ alkoxy, $C_1$-$C_6$ haloalkoxy, —CN, nitro, —$COOR^{11}$, and —$NR^aR^b$;

$R^a$ and $R^b$ are each independently hydrogen or $C_1$-$C_6$ alkyl; $R^{15}$ at each occurrence is independently hydrogen, halogen, hydroxyl, $C_1$-$C_6$ alkyl, $C_1$-$C_6$ haloalkyl, $C_1$-$C_6$ alkoxy, $C_1$-$C_6$ haloalkoxy, —CN, nitro, —$COOR^{11}$, —$CONR^aR^b$, and —$NR^aR^b$;

n at each occurrence is independently 0 or an integer selected from 1 to 4; and $R^{11}$ at each occurrence is independently hydrogen, $C_1$-$C_6$ alkyl, or benzyl.

In another aspect, the present invention provides compounds of formula (Ia):

(Ia)

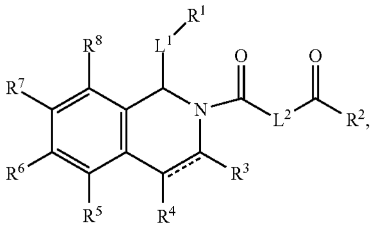

or a stereoisomer, a prodrug, or a pharmaceutically acceptable salt or solvate thereof, wherein:

"$\overset{\text{---}}{=}$" is a single or double bond;

$L^1$ is —$[C(R^{10})_2]_i$—, wherein $R^{10}$ at each occurrence is independently hydrogen, halogen, $C_1$-$C_4$ alkyl, and i is 1, 2, or 3;

$L^2$ is —$[C(R^{20})_2]_j$—, $C_3$-$C_8$ cycloalkylene, $C_6$-$C_{10}$ arylene, 5- to 10-membered heteroarylene, 5- to 10-membered heterocyclylene, wherein $R^{20}$ at each occurrence is independently hydrogen, halogen, or $C_1$-$C_4$ alkyl, and j is an integer selected from 1 through 6;

$R^1$ is selected from

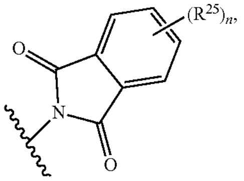

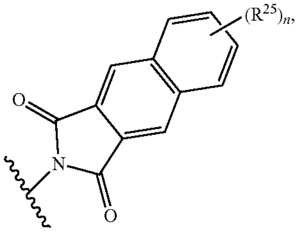

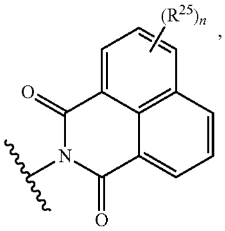, 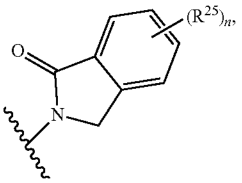

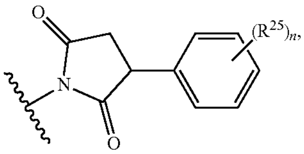

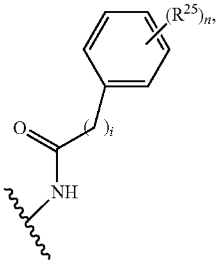 and 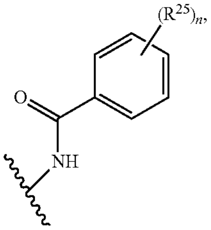

(i = 1, 2, or 3)

wherein n at each occurrence is independently 0 or an integer from 1 to 4, and $R^{25}$ at each occurrence is independently hydrogen, halogen, hydroxyl, $C_1$-$C_6$ alkyl, $C_1$-$C_6$ haloalkyl, $C_1$-$C_6$ alkoxy, $C_1$-$C_6$ haloalkoxy, —CN, nitro, —$COOR^{11}$, —$CONR^aR^b$, substituted or unsubstituted $C_6$-$C_{10}$ aryl, and —$NR^aR^b$;

$R^2$ is —$OR^9$ or —$NR^aR^b$;

$R^3$ through $R^8$ are each independently hydrogen, halogen, hydroxyl, $C_1$-$C_6$ alkyl, $C_1$-$C_6$ haloalkyl, $C_1$-$C_6$ alkoxy, $C_1$-$C_6$ haloalkoxy, $C_3$-$C_8$ cycloalkyl, $C_6$-$C_{10}$ aryl, 5- to 10-membered heteroaryl, 5- to 10-membered heterocyclyl, —CN, nitro, —$COOR^{11}$, or —$NR^aR^b$;

$R^9$ at each occurrence is independently hydrogen or $C_1$-$C_6$ alkyl;

wherein any said cycloalkyl, or heterocyclyl is optionally substituted by one or more substituents independently selected from halogen, hydroxyl, $C_1$-$C_6$ alkyl, $C_1$-$C_6$ haloalkyl, $C_1$-$C_6$ alkoxy, $C_1$-$C_6$ haloalkoxy, —CN, nitro, oxo, —$COOR^{11}$, and —$NR^aR^b$;

each said aryl or heteroaryl is optionally substituted by one or more substituents independently selected from halogen, hydroxyl, $C_1$-$C_6$ alkyl, $C_1$-$C_6$ haloalkyl, $C_1$-$C_6$ alkoxy, $C_1$-$C_6$ haloalkoxy, —CN, nitro, —$COOR^{11}$, and —$NR^aR^b$;

$R^a$ and $R^b$ are each independently hydrogen or $C_1$-$C_6$ alkyl; and $R^{11}$ at each occurrence is independently hydrogen or $C_1$-$C_6$ alkyl;

provided that the compound of formula (I) is not

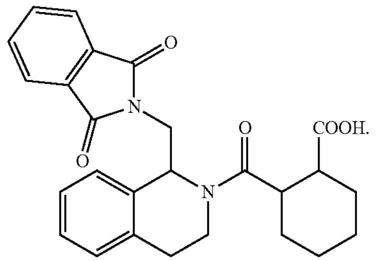 [SMILES: O=C(O)C1CCCCC1C(=O)N1CCc2ccccc2C1CN1C(=O)c2ccccc2C1=O]

In another aspect, the invention provides a composition comprising a compound of formula (I) according to any of embodiments described herein, and a pharmaceutically acceptable carrier.

In another aspect, the invention provides a method of treating a disease or disorder associated with Keap1-Nrf2 interaction, comprising administering to a subject in need thereof a therapeutically effective amount of the compound of formula (I), (II), or (Ia), or composition thereof, according to any of the embodiments described herein.

The present invention thus provides use of a compound of formula (I), (II), or (Ia), or composition thereof, according to any of the embodiments described herein in the manufacture of a medicament for treatment of an inflammatory disease or disorder associated with Keap1-Nrf2 interaction.

In any of the aspects or embodiments described above, the disease or disorder can include any of those associated with Keap1-Nrf2 interaction and/or caused by oxidative stress and inflammation, including but not limited to cancers, diabetes, Alzheimer's, Parkinson's.

About 100 LH601 analogs are synthesized to derive a preliminary structure-activity relationship (SAR) around this hit molecule, many of which have shown ability to effectively block the interaction between Keap1 and Nrf2.

These and other aspects of the present invention will be better appreciated in view of the following drawings, detailed descriptions, and claims.

DETAILED DESCRIPTION OF THE INVENTION

Figure 1:
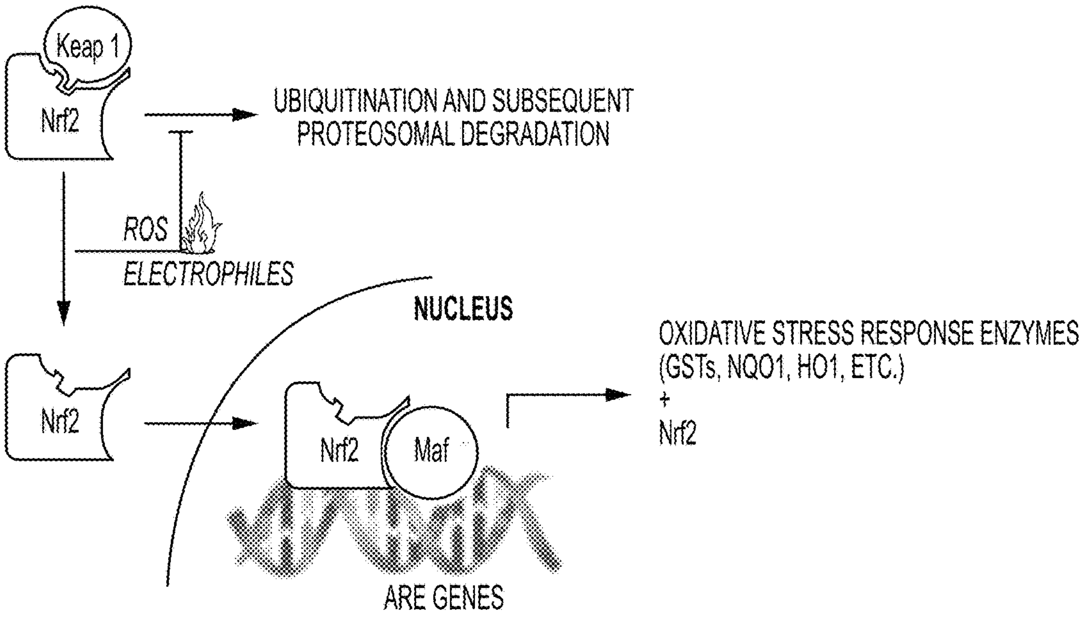
FIG. 1 illustrates a simplified scheme depicting the activation of Nrf2 transcription factor. Nrf2 is sequestered in the cytosol by the protein inhibitor, Keap1, and is transcriptionally inactive. Reactive oxygen species or electrophiles either cause the dissociation of Keap1 or inhibition of ubiquitination and degradation of Keap1-Nrf2 complex, both of which would allow more Nrf2 to translocate to the nucleus and form a transcriptionally active complex with Maf, leading to the induced expression of Nrf2 itself and oxidative stress response enzymes that deactivate reactive oxygen species and electrophiles.

The present invention provides a novel approach to the discovery and identification of drug candidates for treatment of inflammatory diseases or disorders. It provides new methods for fighting oxidative stress and inflammation mediated diseases, including but not limited to cancers, diabetes, Alzheimer's, and Parkinson's. The method protects cells and tissues against various oxidative, inflammatory, and carcinogenic compounds or metabolites derived from exogenous or endogenous sources. In particular, the invention uses Keap1-Nrf2 protein-protein interaction as a novel target for the discovery of direct inhibitors of Keap1-Nrf2 protein-protein interaction to obtain potent activators of Nrf2 and ARE-mediated genes to modulate inflammatory processes.

Oxidative stress and inflammation are byproducts of normal cellular processes. Oxidative stress can damage cellular proteins, membranes and genes, and can lead to inflammation. Oxidative stress and inflammation are not diseases themselves, but they are implicated in many diseases and conditions including cancer, Alzheimer's, Parkinson's, asthma, and diabetes. Controlling oxidative stress can reduce inflammation and potentially prevent and treat the many oxidative stress-related diseases and conditions. The Keap1-Nrf2-ARE system has been identified as the central regulatory pathway in response to oxidative stress. Keap1 binding to Nrf2 prevents Nrf2 from entering the nucleus and leads to ubiquitination and subsequent degradation of Nrf2 under normal conditions; it acts as a chemical sensor that controls the steady state level of Nrf2 based on cellular redox conditions. Keap1-Nrf2 protein-protein interaction is, thus, an attractive target to regulate the cellular Nrf2 level and ARE gene expression, for the control of oxidative stress and inflammation and for the management of many diseases and conditions.

Most research efforts in chemoprevention and antioxidant inflammation modulation over the past decade have focused on natural products that are isolated from fruit, vegetables, and tea products, but are indirect inhibitors of Keap1-Nrf2 interaction. These compounds include sulforaphane, phenethyl isothiocyanate, curcumin, resveratrol and epigallocatechin gallate (EGCG). Structurally, these compounds are either chemically reactive (an isothiocyanate or a Michael acceptor) or can be metabolized to chemically reactive species that covalently modify Keap1 and activate Nrf2-mediated ARE genes. To obtain direct inhibitors of Keap1-Nrf2 interaction, the present invention involves using state-of-the-art methodologies in drug design—high throughput screening for lead discovery, X-ray crystallography (co-crystal structures), structure-based rational drug design, and computer-assisted lead optimization. The direct inhibitors of Keap1-Nrf2 interaction identified will be useful as pharmacological probes for the elucidation of Keap1-Nrf2-ARE signaling pathway and as potential preventive and therapeutic agents for a variety of diseases and conditions.

In one aspect, the present invention provides the discovery of novel Nrf2 activators/ARE inducers through high throughput screening of the MLPCN small molecule library. The screening provided novel leads for further optimization into potent direct inhibitors of the protein-protein interaction between Keap1 and Nrf2, including developing and submitting the HTS FP assay to the MLPCN, screening lead optimization efforts in terms of analog design and synthesis, investigating their in vitro and in vivo biological activities, including chemopreventive and anti-inflammatory properties using a variety of molecular biological techniques and in vivo pharmacology studies, crystallizing and analyzing the cocrystal structure of Keap1 Kelch domain with potent direct inhibitors obtained.

The method of identifying novel direct inhibitors of the Keap1-Nrf2 interaction, as illustrated in FIG. 7, also includes synthesizing analogs of the identified lead compounds, for example, the eight lead compounds identified in a Keap1-retest in dose-response curves and screening their inhibitory activity against the Keap1-Nrf2 interaction:

(1R,2S)-rel-2-[[1-[(1,3-dihydro-1,3-dioxo-2H-isoindol-2-yl)methyl]-3,4-dihydro-2(1H)-isoquinolinyl]carbonyl]cyclohexanecarboxylic acid (Hit 1, LH601, BRD-A69788832-001-06-6), $IC_{50}$: 3 μM

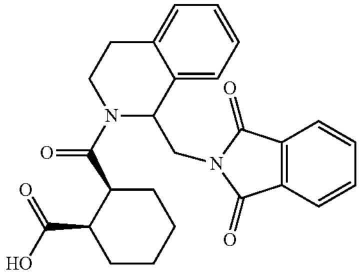 [SMILES: O=C(O)[C@@H]1CCCC[C@@H]1C(=O)N1CCc2ccccc2C1CN1C(=O)c2ccccc2C1=O]

4-[[(2,4-Dimethylphenyl)sulfonyl]amino]-1-hydroxy-α-(2,2,2-trifluoroacetyl)-2-naphthaleneacetic acid, 1-methylethyl ester (Hit 2, LH602, BRD-A09671526-001-05-0), $IC_{50}$: 2.7 μM

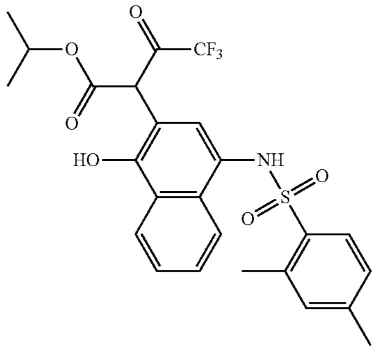 [SMILES: Cc1ccc(S(=O)(=O)Nc2cc(C(C(=O)OC(C)C)C(=O)C(F)(F)F)c(O)c3ccccc23)c(C)c1]

3-(Aminosulfonyl)-4-chloro-N-(3,4-dihydro-2H-1-benzothiopyran-4-yl)benzamide (BRD-A83249228-001-07-1), $IC_{50}$: 135 uM

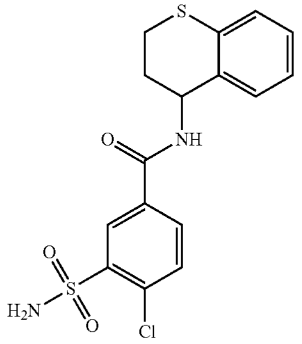 [SMILES: NS(=O)(=O)c1cc(C(=O)NC2CCSc3ccccc32)ccc1Cl]

2-[[[2-[2-[1-(2,4-dimethoxyphenyl)ethylidene]hydrazinyl]-5-nitrophenyl]sulfonyl]amino] benzoic acid (BRD-K09114961-001-03-6), $IC_{50}$: 26 μM

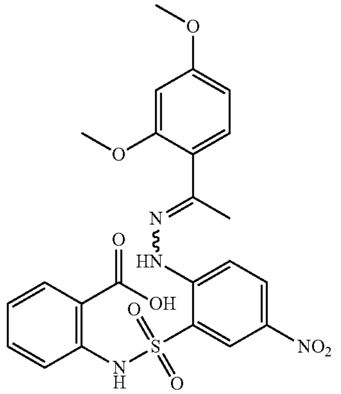 [SMILES: COc1ccc(C(C)=NNc2ccc([N+](=O)[O-])cc2S(=O)(=O)Nc2ccccc2C(=O)O)c(OC)c1]

8,9-Didehydro-6,8-dimethyl-ergoline (BRD-K56215778-001-06-9), $IC_{50}$: 37 μM

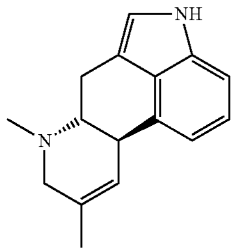

1,2-Dihydro-2-oxo-N-(7,8,9,10-tetrahydro-7-oxobenzo[b]naphtho[2,1-d]furan-5-yl) benz[cd]indole-6-sulfonamide (BRD-K91732811-001-06-9), $IC_{50}$: 55 μM

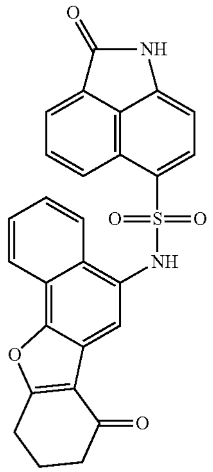 [SMILES: O=C1CCCc2oc3c(cc(NS(=O)(=O)c4ccc5c6c(cccc46)C(=O)N5)c4ccccc43)c21]

3-(2-Furanyl)-N-[[[4-[[(6-methoxy-4-pyrimidinyl)amino]sulfonyl]phenyl]amino]-thioxomethyl]-2-Propenamide (BRD-K42553821-001-05-9), $IC_{50}$: 91 μM

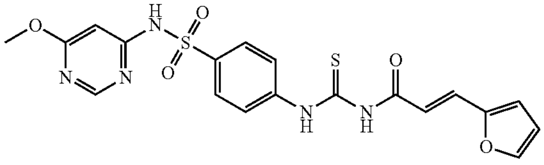 [SMILES: COc1cc(NS(=O)(=O)c2ccc(NC(=S)NC(=O)/C=C/c3ccco3)cc2)ncn1]

3,5-Bis(2,5-dihydro-2,5-dioxo-1H-pyrrol-1-yl)-benzoic acid (BRD-K11951445-001-04-1), $IC_{50}$: 19 μM

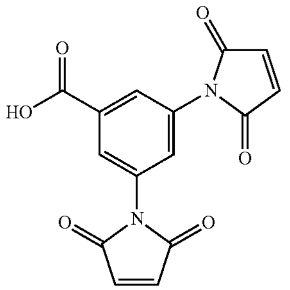 [SMILES: O=C(O)c1cc(N2C(=O)C=CC2=O)cc(N2C(=O)C=CC2=O)c1]

Using the described strategy, a number of novel compounds have been identified as director inhibitors of Keap1-Nrf2 interaction, and structure-activity relationship (SAR) have been revealed for the Lead Compound LH601.

Thus, in one aspect, the present invention provides methods of preventing or treating an inflammatory disease or disorder, comprising administering to a subject in need thereof a therapeutically effective amount of an agent that is a non-peptide small molecule direct inhibitor of Keap1-Nrf2 protein-protein interaction.

In one aspect, the present invention provides a method of preventing or treating an inflammatory disease or disorder, comprising administering to a subject in need thereof a therapeutically effective amount of a compound of formula (I):

(I)

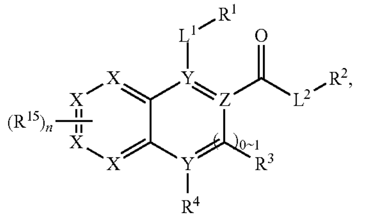

or a stereoisomer, a prodrug, or a pharmaceutically acceptable salt or solvate thereof, wherein:

"═" at each occurrence is independently a single or double bond;

X at each occurrence is independently nitrogen (N) or carbon (C or CH);

Y at each occurrence is independently nitrogen (N) or carbon (C or CH);

Z is nitrogen (N) or carbon (C or CH);

$L^1$ is —$[C(R^{10})_2]_i$—, wherein $R^{10}$ at each occurrence is independently hydrogen, halogen, $C_1$-$C_4$ alkyl, or $C_1$-$C_4$ haloalkyl, and i is 0, 1, 2, or 3;

$L^2$ is —$[C(R^{20})_2]_j$—, $C_3$-$C_8$ cycloalkylene, $C_6$-$C_{10}$ arylene, 5- to 10-membered heteroarylene, or 5- to 10-membered heterocyclylene, each optionally substituted by one to three substituents independently selected from halogen, hydroxyl, $C_1$-$C_4$ alkyl, and $C_1$-$C_4$ haloalkyl, —$OR^9$, and —$NR^aR^b$, wherein $R^{20}$ at each occurrence is independently hydrogen, halogen, $C_1$-$C_4$ alkyl, or $C_1$-$C_4$ haloalkyl, and wherein j is an integer selected from 1 through 6;

$R^1$ is an amido or imido group, said amido or imido group comprising a group selected from unsubstituted or substituted $C_6$-$C_{10}$ aryls and unsubstituted or substituted 5- to 10-membered heteroaryls;

$R^2$ is selected from

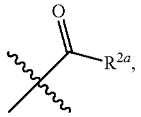 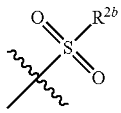, 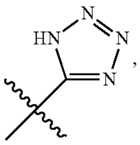,

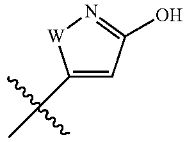

(W=O, S, or NH),

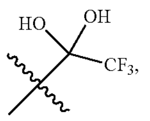 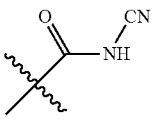, and

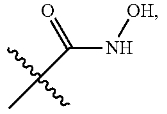

wherein $R^{2a}$ and $R^{2b}$ are each independently —$OR^9$ or —$NR^aR^b$;

$R^3$ and $R^4$ are each independently hydrogen, halogen, hydroxyl, $C_1$-$C_6$ alkyl, $C_1$-$C_6$ haloalkyl, $C_1$-$C_6$ alkoxy, $C_1$-$C_6$ haloalkoxy, $C_3$-$C_8$ cycloalkyl, $C_6$-$C_{10}$ aryl, 5- to 10-membered heterocyclyl, 5- to 10-membered heterocyclyl, —CN, nitro, —$COOR^{11}$, or —$NR^aR^b$;

$R^9$ at each occurrence is independently hydrogen, $C_1$-$C_6$ alkyl, $C_1$-$C_6$ haloalkyl, or benzyl;

wherein any said cycloalkyl or heterocyclyl is optionally substituted by one or more substituents independently selected from halogen, hydroxyl, $C_1$-$C_6$ alkyl, $C_1$-$C_6$ haloalkyl, $C_1$-$C_6$ alkoxy, $C_1$-$C_6$ haloalkoxy, —CN, nitro, oxo, —$COOR^{11}$, and —$NR^aR^b$;

each said aryl or heteroaryl is optionally substituted by one or more substituents independently selected from halogen, hydroxyl, $C_1$-$C_6$ alkyl, $C_1$-$C_6$ haloalkyl, $C_1$-$C_6$ alkoxy, $C_1$-$C_6$ haloalkoxy, —CN, nitro, —$COOR^{11}$, and —$NR^aR^b$;

$R^a$ and $R^b$ at each occurrence are independently hydrogen or $C_1$-$C_6$ alkyl;

$R^{11}$ at each occurrence is independently hydrogen, $C_1$-$C_6$ alkyl, or benzyl;

$R^{15}$ at each occurrence is independently hydrogen, halogen, hydroxyl, $C_1$-$C_6$ alkyl, $C_1$-$C_6$ haloalkyl, $C_1$-$C_6$ alkoxy, $C_1$-$C_6$ haloalkoxy, —CN, nitro, —$COOR^{11}$, —$CONR^aR^b$, and —$NR^aR^b$; and n at each occurrence is independently 0 or an integer selected from 1 to 4.

In one embodiment of this aspect, the

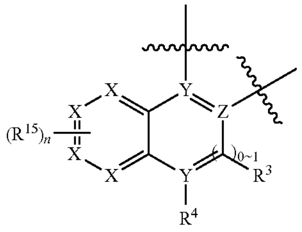

moiety of formula (I) is selected from:

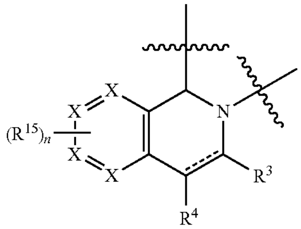

,

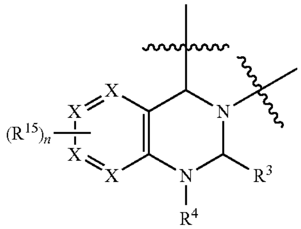

,

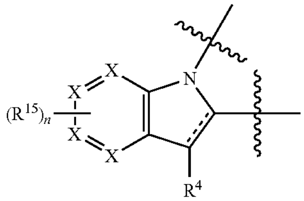

, and

-continued

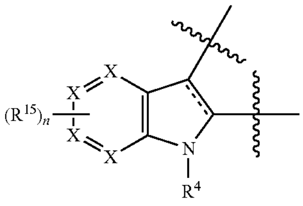

.

In a preferred embodiment of this aspect, the

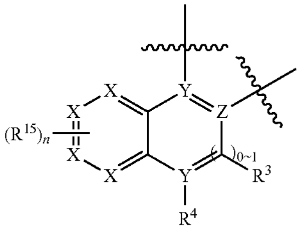

moiety of formula (I) is

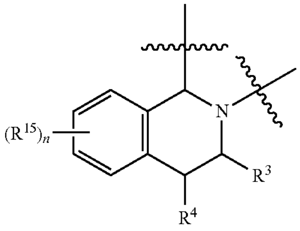

.

In another embodiment of this aspect, the

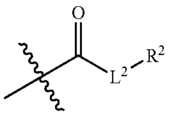

moiety of formula (I) is selected from:

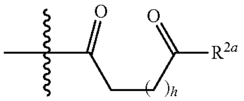

(h=0 or an integer between 1-5), $R^{12}$

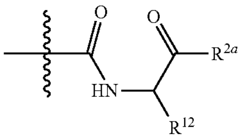

=H or $C_1$-$C_4$ alkyl),

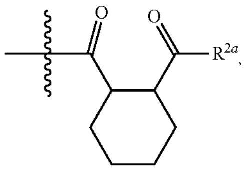

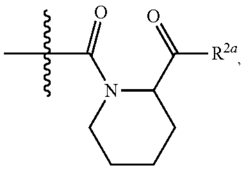

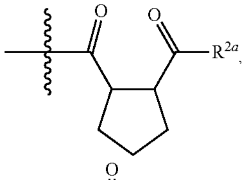

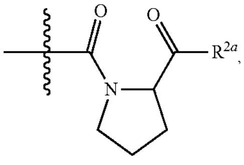

and

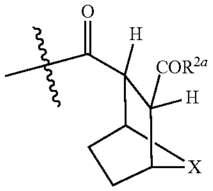

($X=CH_2$ or O).

In another embodiment of this aspect, the

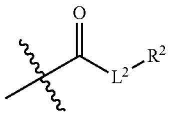

moiety of formula (I) is selected from:

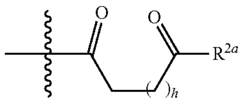

(h=1 or 2) and

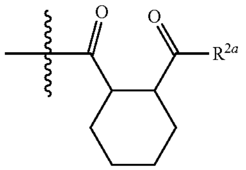

wherein $R^{2a}$ is OH.

In another embodiment of this aspect, in the compound of formula (I), the amido or imido of $R^1$ group has a formula of

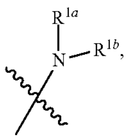

wherein $R^{1a}$ and $R^{1b}$ are each independently hydrogen or a group selected from:

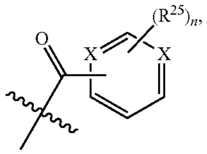

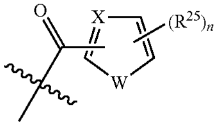

(W=O, S, or NH),

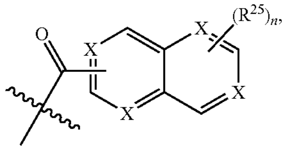

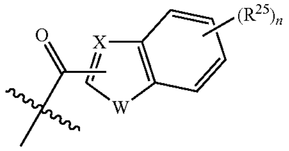

(W=O, S, or NH),

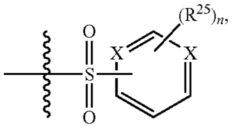

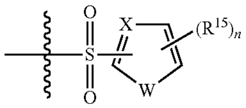

(W=O, S, or NH),

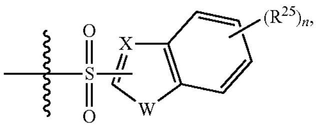

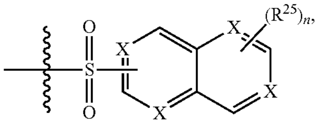

or alternatively $R^{1a}$ and $R^{1b}$ together form a group selected from:

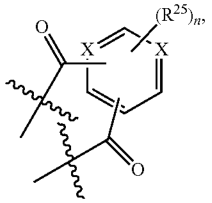

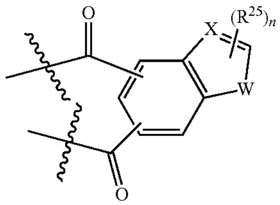

(W=O, S, or NH),

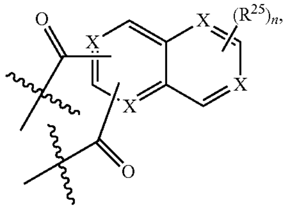

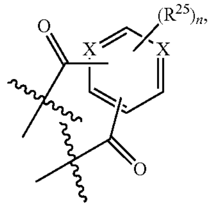

-continued

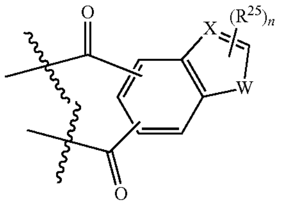

(W=O, S, or NH), and

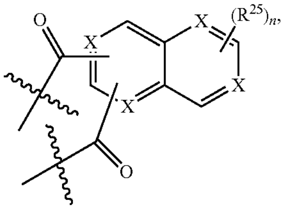

wherein n at each occurrence is independently 0 or an integer from 1 to 4, and $R^{25}$ at each occurrence is independently hydrogen, halogen, hydroxyl, $C_1$-$C_6$ alkyl, $C_1$-$C_6$ haloalkyl, $C_1$-$C_6$ alkoxy, $C_1$-$C_6$ haloalkoxy, —CN, nitro, —$COOR^{11}$, —$CONR^aR^b$, substituted or unsubstituted phenyl, and —$NR^aR^b$.

In another embodiment of this aspect, $R^{1a}$ and $R^{1b}$ together form a group selected from:

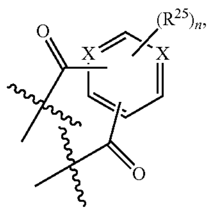

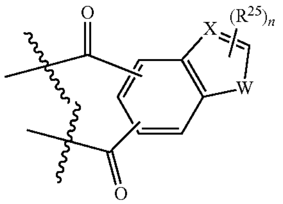

(W=O, S, or NH),

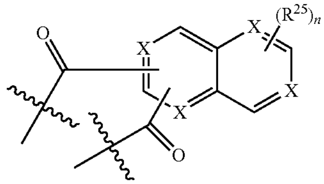

,

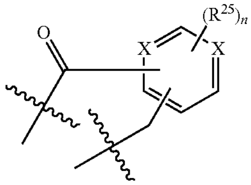

,

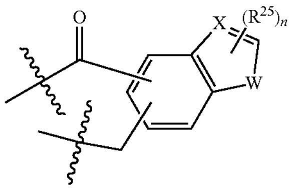

(W=O, S, or NH), and

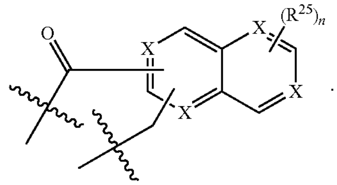

.

In another embodiment of this aspect, $R^{1a}$ and $R^{1b}$ together form a group selected from:

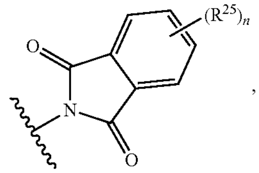

,

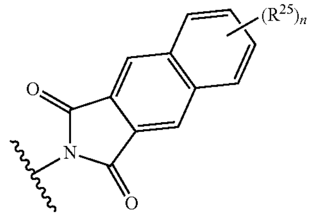

,

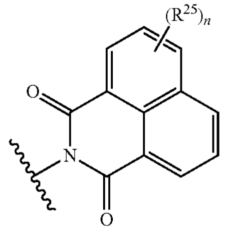

,

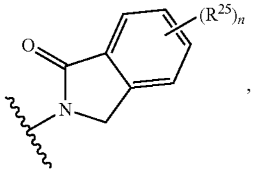

, and

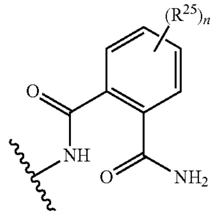

, wherein n at each occurrence is independently 0, 1, or 2; and $R^{25}$ at each occurrence is independently halogen, hydroxyl, $C_1$-$C_6$ alkyl, $C_1$-$C_6$ haloalkyl, $C_1$-$C_6$ alkoxy, $C_1$-$C_6$ haloalkoxy, —CN, nitro, —$COOR^{11}$, phenyl, and —$NR^aR^b$, wherein $R^{11}$, $R^a$, and $R^b$ are each independently hydrogen or $C_1$-$C_6$ alkyl.

As a person of skill in the art would appreciate, any combinations of the embodiments described above with respect to the various moieties of formula (I) are within the scope of the disclosure.

In another embodiment of this aspect, the agent is a compound of formula (Ia):

(Ia)

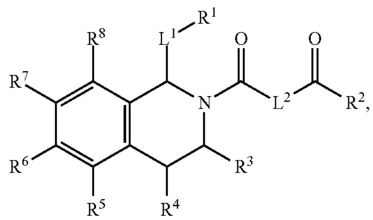

or a stereoisomer, a prodrug, or a pharmaceutically acceptable salt or solvate thereof, wherein:

"═══" is a single or double bond;

$L^1$ is —[C($R^{10}$)$_2$]$_i$—, wherein $R^{10}$ at each occurrence is independently hydrogen, halogen, $C_1$-$C_4$ alkyl, or $C_1$-$C_4$ haloalkyl, and i is 0, 1, 2, or 3;

$L^2$ is —[C($R^{20}$)$_2$]$_j$—, $C_3$-$C_8$ cycloalkylene, $C_6$-$C_{10}$ arylene, 5- to 10-membered heteroarylene, 5- to 10-membered heterocyclylene, wherein $R^{20}$ at each occurrence is independently hydrogen, halogen, or $C_1$-$C_4$ alkyl, or $C_1$-$C_4$ haloalkyl, and wherein j is an integer selected from 1 through 6;

$R^1$ is an amido or imido group, said amido or imido group comprising a group selected from $C_6$-$C_{14}$ aryls and 5- to 10-membered heteroaryls;

$R^2$ is —$OR^9$ or —$NR^aR^b$;

$R^3$ through $R^8$ are each independently hydrogen, halogen, hydroxyl, $C_1$-$C_6$ alkyl, $C_1$-$C_6$ haloalkyl, $C_1$-$C_6$ alkoxy, $C_1$-$C_6$ haloalkoxy, $C_3$-$C_8$ cycloalkyl, $C_6$-$C_{10}$ aryl, 5- to 10-membered heterocyclyl, 5- to 10-membered heterocyclyl, —CN, nitro, —$COOR^{11}$, or —$NR^aR^b$;

$R^9$ at each occurrence is independently hydrogen, $C_1$-$C_6$ alkyl, $C_1$-$C_6$ haloalkyl, or benzyl;

wherein any said cycloalkyl, or heterocyclyl is optionally substituted by one or more substituents independently selected from halogen, hydroxyl, $C_1$-$C_6$ alkyl, $C_1$-$C_6$ haloalkyl, $C_1$-$C_6$ alkoxy, $C_1$-$C_6$ haloalkoxy, —CN, nitro, oxo, —$COOR^{11}$, and —$NR^aR^b$;

each said aryl or heteroaryl is optionally substituted by one or more substituents independently selected from halogen, hydroxyl, $C_1$-$C_6$ alkyl, $C_1$-$C_6$ haloalkyl, $C_1$-$C_6$ alkoxy, $C_1$-$C_6$ haloalkoxy, —CN, nitro, —$COOR^{11}$, and —$NR^aR^b$;

$R^a$ and $R^b$ are each independently hydrogen or $C_1$-$C_6$ alkyl; and $R^{11}$ at each occurrence is independently hydrogen or $C_1$-$C_6$ alkyl.

In another embodiment of this aspect, the compound of formula (Ia) is defined as follows:

"═══" is a single bond;

$L^1$ is —($CH_2$)$_i$—, wherein i is 1 or 2;

$L^2$ is —($CH_2$)$_j$— (j is 1, 2, or 3) or $C_3$-$C_8$ cycloalkylene;

$R^1$ is selected from

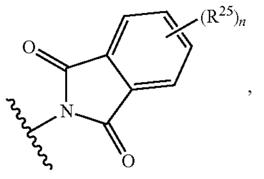

,

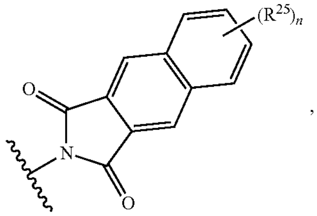

,

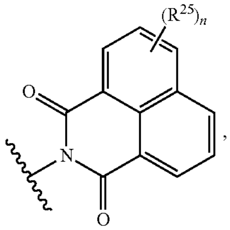

,

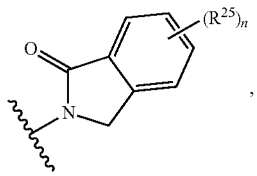

,

-continued and

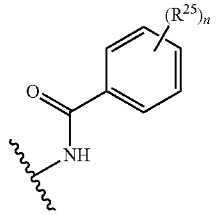

, wherein n at each occurrence is independently 0 or an integer from 1 to 4, and $R^{25}$ at each occurrence is independently hydrogen, halogen, hydroxyl, $C_1$-$C_6$ alkyl, $C_1$-$C_6$ haloalkyl, $C_1$-$C_6$ alkoxy, $C_1$-$C_6$ haloalkoxy, —CN, nitro, —$COOR^{11}$, —$CONR^aR^b$, substituted or unsubstituted phenyl, and —$NR^aR^b$;

$R^2$ is —$OR^9$ or —$NR^aR^b$;

$R^3$ through $R^8$ are each independently hydrogen, halogen, hydroxyl, $C_1$-$C_6$ alkyl, $C_1$-$C_6$ haloalkyl, $C_1$-$C_6$ alkoxy, $C_1$-$C_6$ haloalkoxy, $C_6$-$C_{10}$ aryl, nitro, —CN, or —$NR^aR^b$;

$R^9$ at each occurrence is independently hydrogen, $C_1$-$C_6$ alkyl, or benzyl; and $R^a$ and $R^b$ are each independently hydrogen or $C_1$-$C_6$ alkyl.

In another embodiment of this aspect, the compound of formula (Ia) is defined as follows:

"═══" is a single bond;

$L^1$ is —$CH_2$— or —($CH_2$)$_2$—;

$L^2$ is —($CH_2$)$_j$— (j=1, 2, or 3), cyclohexylene, or cyclopentylene;

$R^1$ is

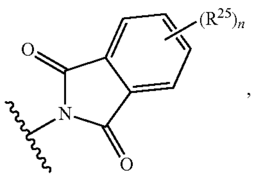

,

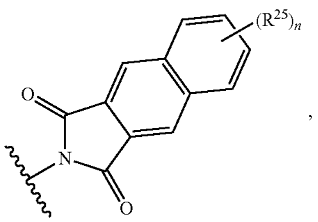

,

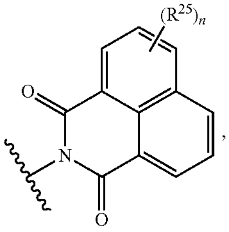

,

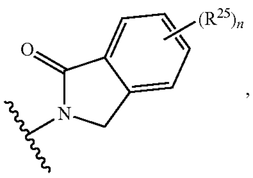

, and

-continued

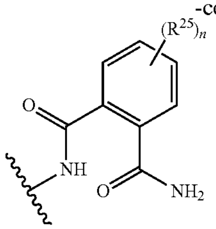

, wherein n at each occurrence is independently 0, 1, or 2; and $R^{25}$ at each occurrence is independently halogen, hydroxyl, $C_1$-$C_6$ alkyl, $C_1$-$C_6$ haloalkyl, $C_1$-$C_6$ alkoxy, $C_1$-$C_6$ haloalkoxy, —CN, nitro, —$COOR^{11}$, phenyl, and —$NR^aR^b$;

$R^2$ is —$OR^9$;

$R^3$ and $R^4$ are each hydrogen;

$R^5$ through $R^8$ are each independently hydrogen, halogen, hydroxyl, $C_1$-$C_6$ alkyl, $C_1$-$C_6$ haloalkyl, $C_1$-$C_6$ alkoxy, $C_1$-$C_6$ haloalkoxy, phenyl, or —$NR^aR^b$;

$R^9$ is hydrogen; and $R^a$ and $R^b$ are each independently hydrogen or $C_1$-$C_6$ alkyl.

In another embodiment of this aspect, the compound of formula (Ia) is defined as follows:

“==” is a single bond;

$L^1$ is —$CH_2$— or —$(CH_2)_2$—;

$L^2$ is —$(CH_2)_2$—, —$(CH_2)_3$—,

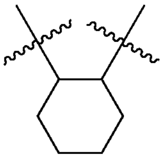

or

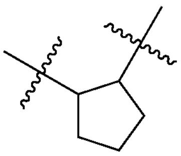

;

$R^1$ is selected from:

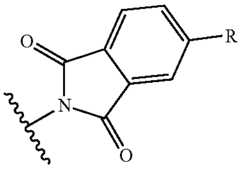

(R=H, F, Cl, Br, -Ph, —$NO_2$, —$NH_2$, $C_1$-$C_4$ alkyl, or —$CO_2H$),

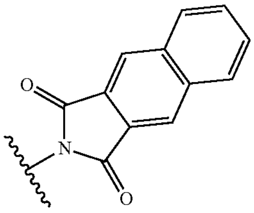

,

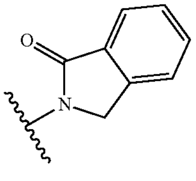

,

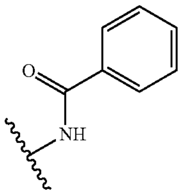

,

-continued

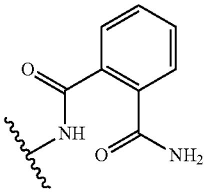

,

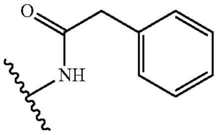

,

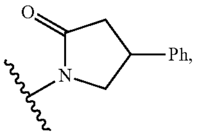

and

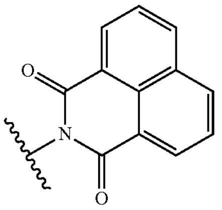

;

$R^2$ is —OH, —$OCH_3$, —$OCH_2Ph$, or —$NH_2$;

$R^3$ and $R^4$ are each hydrogen; and $R^5$ through $R^8$ are each independently hydrogen, F, Cl, Br, OMe, —$NO_2$, or —$NH_2$.

In another embodiment of this aspect, the compound of formula (Ia) is defined as follows:

“==” is a single bond;

$L^1$ is —$CH_2$—;

$L^2$ is

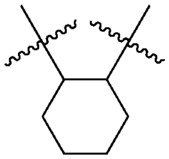

or

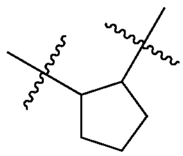

;

$R^1$ is selected from:

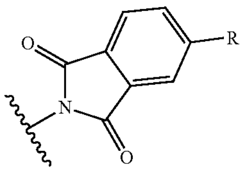

(R=H, F, Br, or -Ph),

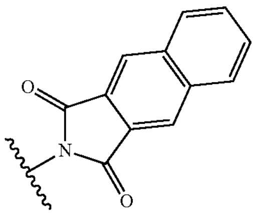

,

-continued
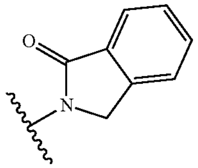
,
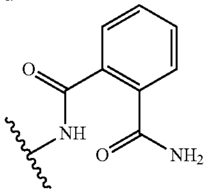
,
and
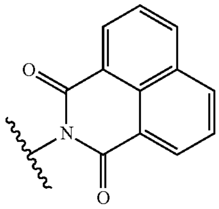
;
$R^2$ is —OH;
$R^3$ and $R^4$ are each hydrogen; and
$R^5$ through $R^8$ are each independently hydrogen, F, OMe, or —$NH_2$.
In another embodiment of this aspect, the compound of formula (Ia) is selected from:
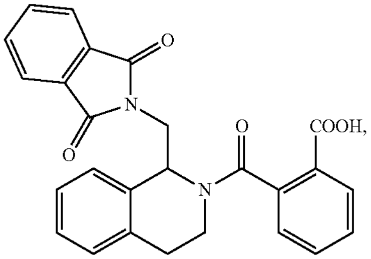
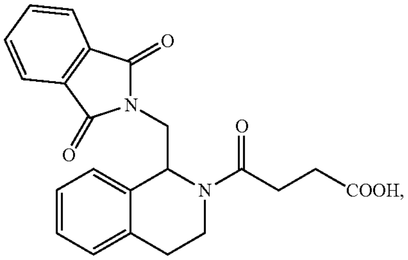
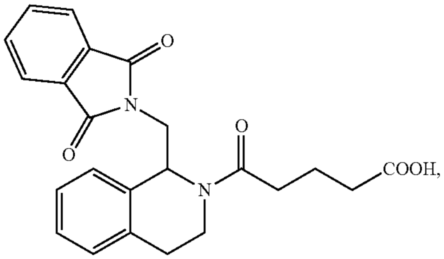
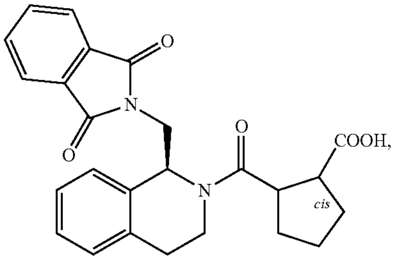
-continued
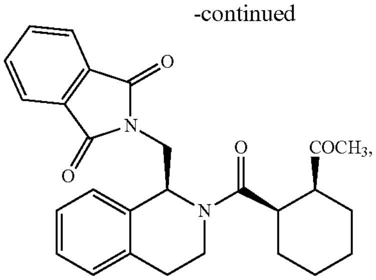
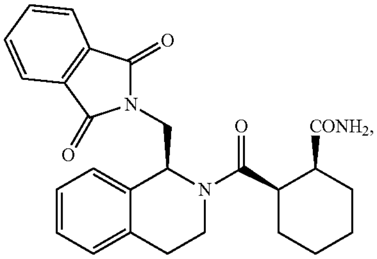
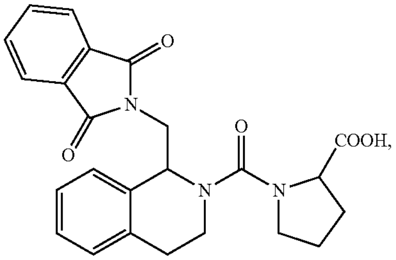
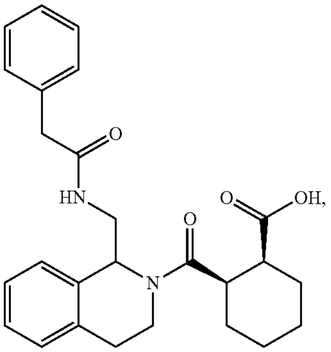
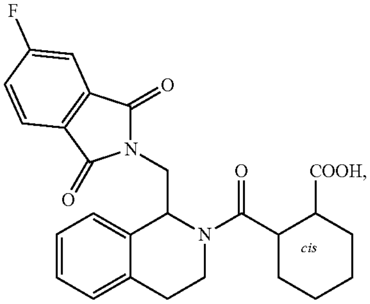
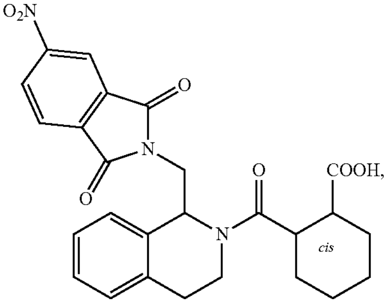

-continued
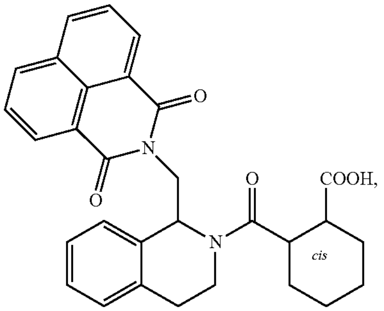
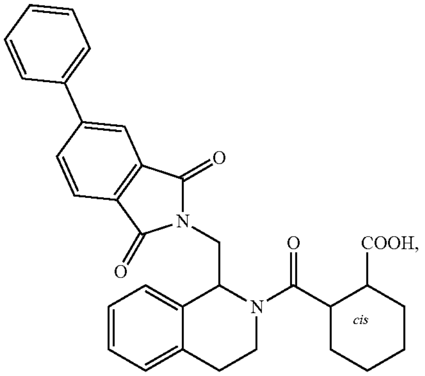
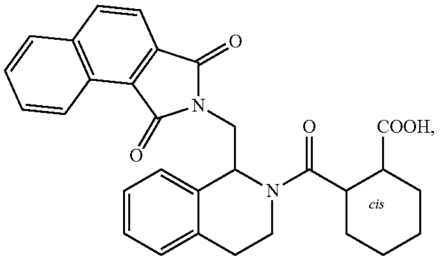
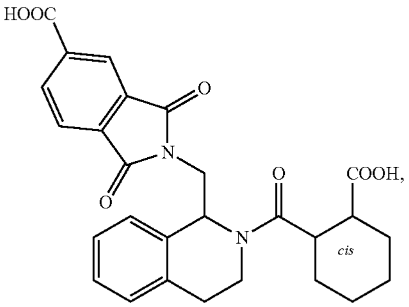
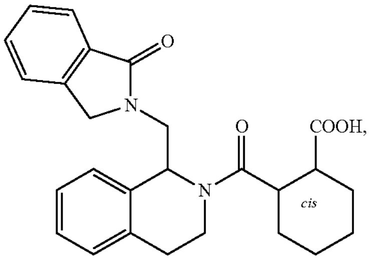
-continued
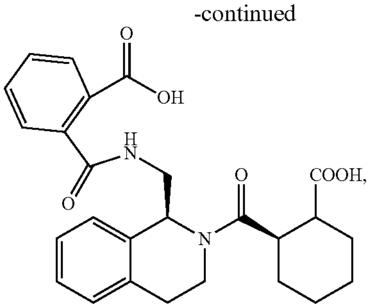
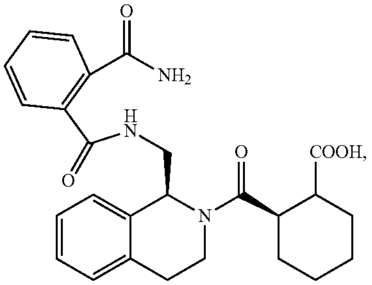
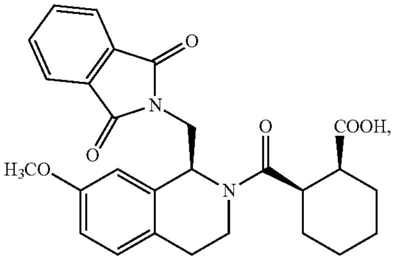
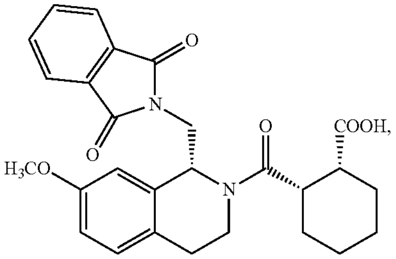
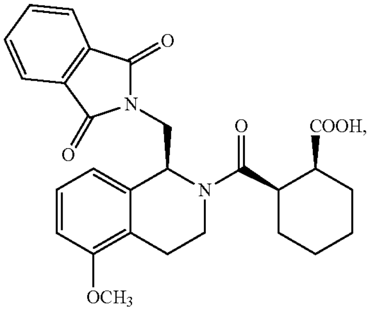
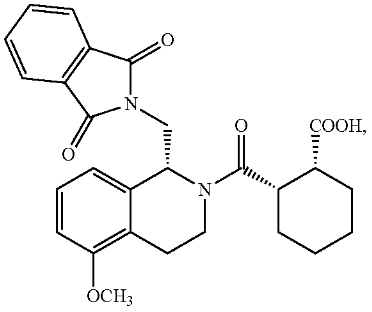

-continued
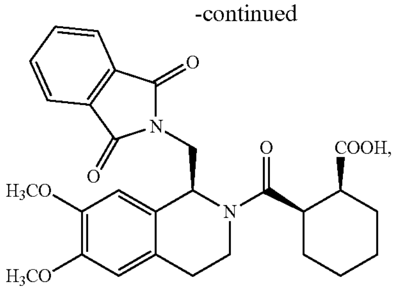
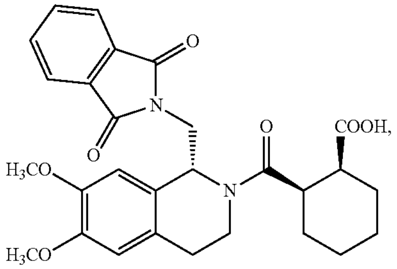
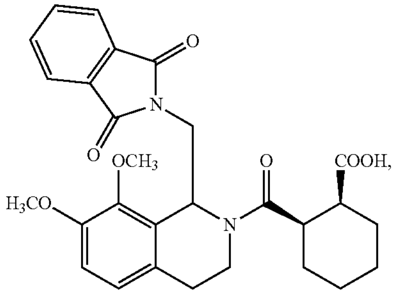
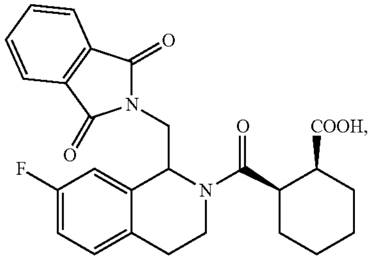
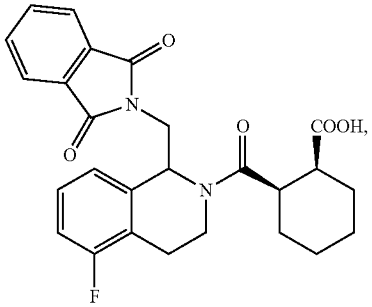
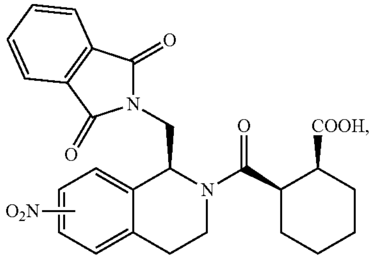
-continued
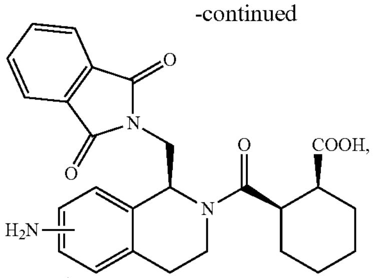
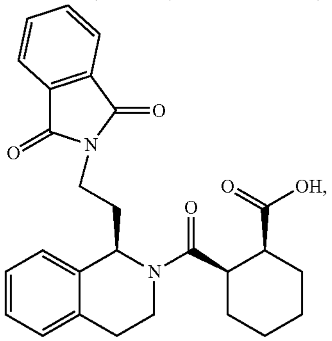
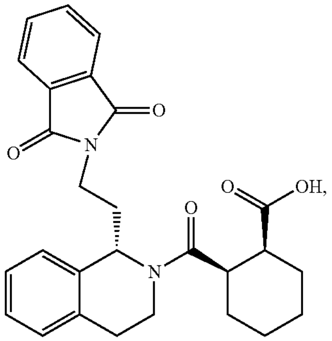
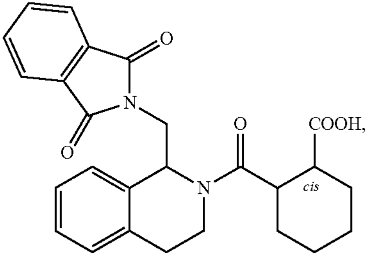 [SMILES: O=C(O)C1CCCCC1C(=O)N1CCc2ccccc2C1CN1C(=O)c2ccccc2C1=O]
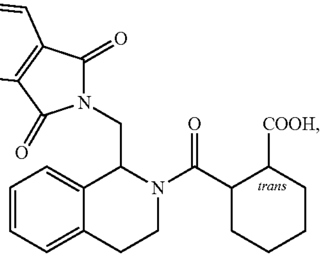
and
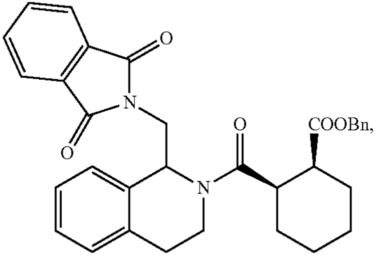

or a stereoisomer, a prodrug, or a pharmaceutically acceptable salt or solvate thereof.
In a preferred embodiment of this aspect, the compound of formula (Ia) is selected from the group consisting of:
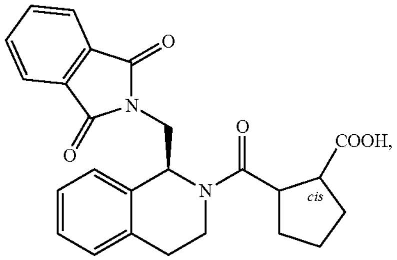
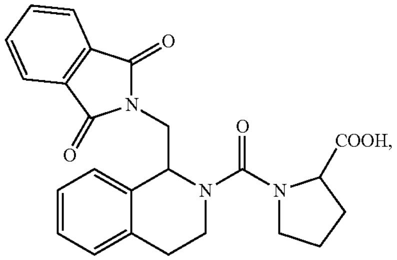
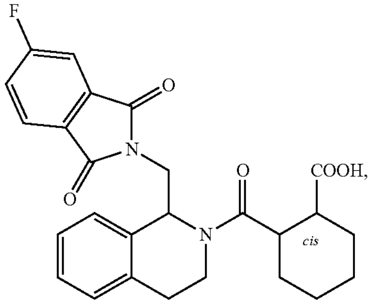
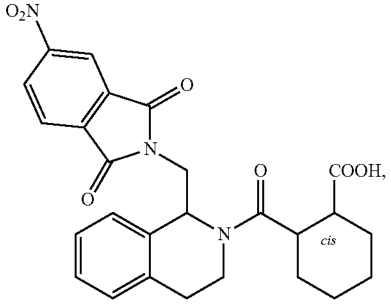
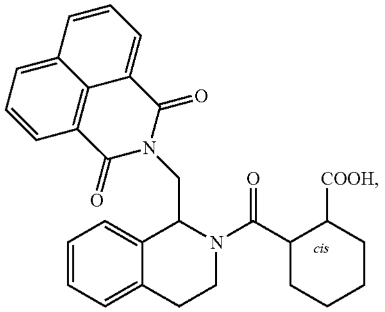
-continued
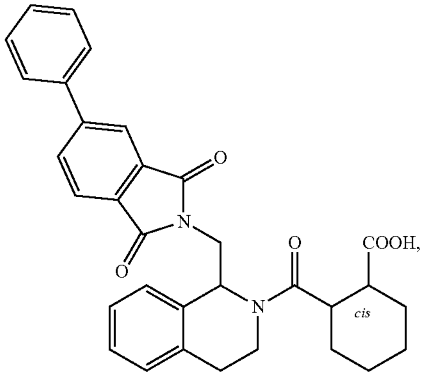
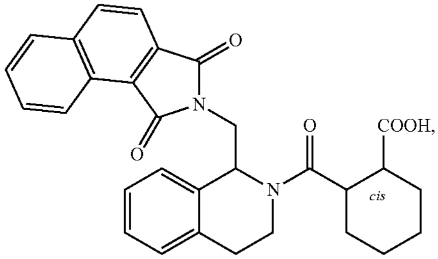
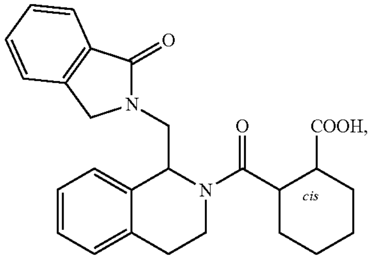
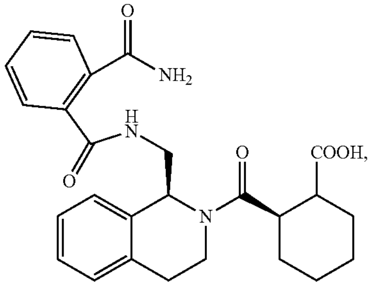
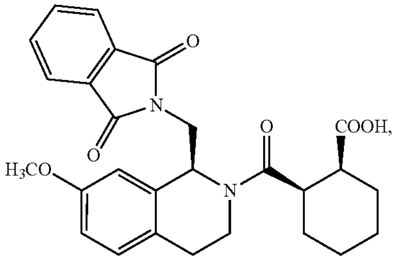

-continued

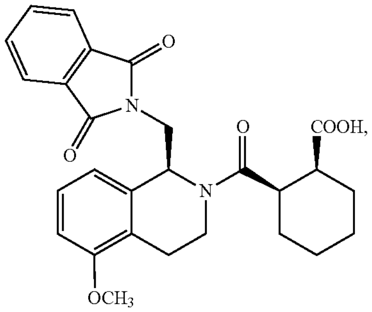

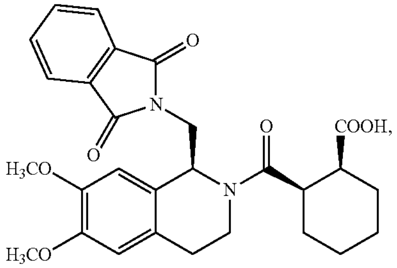

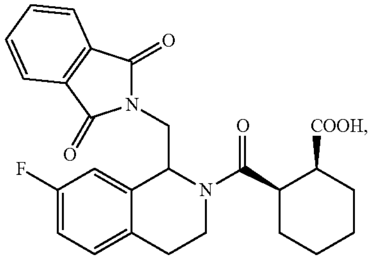

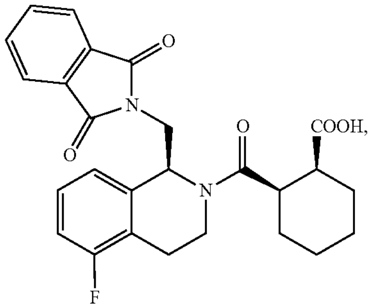

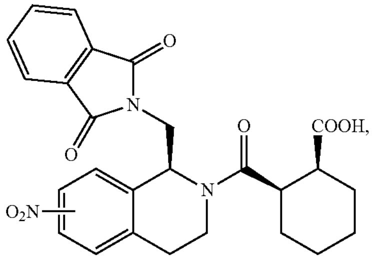

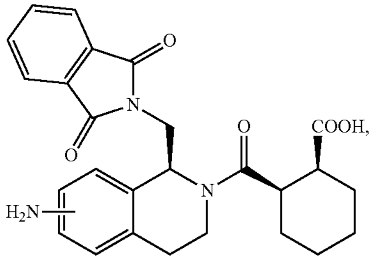

and

-continued

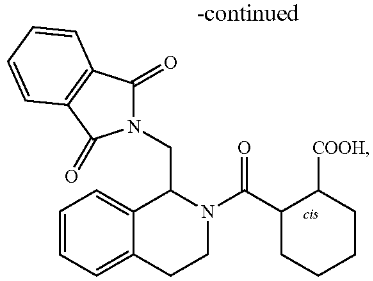

or a stereoisomer, a prodrug, or a pharmaceutically acceptable salt or solvate thereof.

In another aspect, the present invention provides a method of preventing or treating an inflammatory disease or disorder, comprising administering to a subject in need thereof a therapeutically effective amount of a compound of formula (II):

(II)

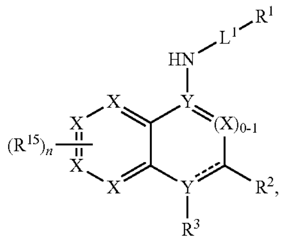

or a stereoisomer, a prodrug, or a pharmaceutically acceptable salt or solvate thereof, wherein:

"$\equiv$" at each occurrence is independently a single or a double bond;

X at each occurrence is independently nitrogen (N) or carbon (C or CH);

Y at each occurrence is independently nitrogen (N) or carbon (C or CH);

$L^1$ is

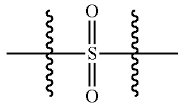

or

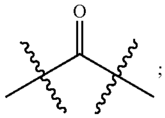

;

$R^1$ is selected from unsubstituted or substituted $C_6$-$C_{10}$ aryls and unsubstituted or substituted 5- to 10-membered heteroaryls;

$R^2$ is

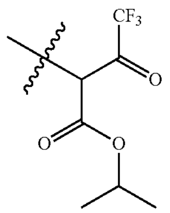 [SMILES: *C(C(=O)OC(C)C)C(=O)C(F)(F)F]

or a bioisosteric group thereof;

$R^3$ is hydrogen, halogen, hydroxyl, $C_1$-$C_6$ alkyl, $C_1$-$C_6$ haloalkyl, $C_1$-$C_6$ alkoxy, $C_1$-$C_6$ haloalkoxy, —$COOR^{11}$, or —$NR^aR^b$;

wherein any said cycloalkyl, or heterocyclyl is optionally substituted by one or more substituents independently selected from halogen, hydroxyl, $C_1$-$C_6$ alkyl, $C_1$-$C_6$ haloalkyl, $C_1$-$C_6$ alkoxy, $C_1$-$C_6$ haloalkoxy, —CN, nitro, oxo, —$COOR^{11}$, and —$NR^aR^b$;

each said aryl or heteroaryl is optionally substituted by one or more substituents independently selected from halogen, hydroxyl, $C_1$-$C_6$ alkyl, $C_1$-$C_6$ haloalkyl, $C_1$-$C_6$ alkoxy, $C_1$-$C_6$ haloalkoxy, —CN, nitro, —$COOR^{11}$, and —$NR^aR^b$;

$R^a$ and $R^b$ are each independently hydrogen or $C_1$-$C_6$ alkyl;

$R^{15}$ at each occurrence is independently hydrogen, halogen, hydroxyl, $C_1$-$C_6$ alkyl, $C_1$-$C_6$ haloalkyl, $C_1$-$C_6$ alkoxy, $C_1$-$C_6$ haloalkoxy, —CN, nitro, —$COOR^{11}$, —$CONR^aR^b$, and —$NR^aR^b$;

n at each occurrence is independently 0 or an integer selected from 1 to 4; and $R^{11}$ at each occurrence is independently hydrogen, $C_1$-$C_6$ alkyl, or benzyl.

In one embodiment of this aspect, the compound of formula (II) is defined as follows:

said bioisosteric group is selected from

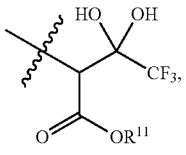

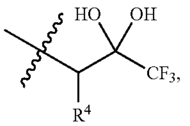

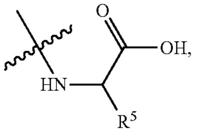

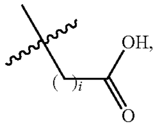

(i=1, 2, or 3),

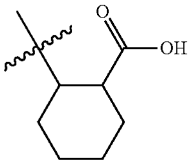

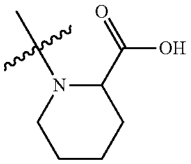

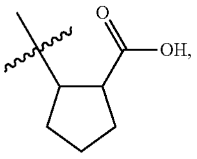

and

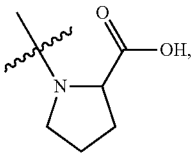

wherein $R^4$ is hydrogen, halogen, hydroxyl, $C_1$-$C_4$ alkyl, $C_1$-$C_4$ haloalkyl, or $C_1$-$C_4$ alkoxy; $R^5$ is hydrogen, $C_1$-$C_4$ alkyl, or $C_1$-$C_4$ haloalkyl; and $R^{11}$ is hydrogen or $C_1$-$C_4$ alkyl.

In another embodiment of this aspect, the $R^1$ group of formula (II) is selected from

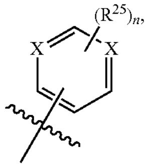

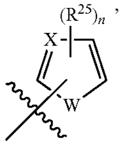

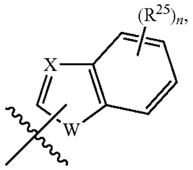

and

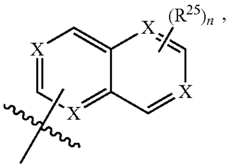

wherein n at each occurrence is independently 0 or an integer selected from 1 to 4; and $R^{25}$ at each occurrence is independently hydrogen, halogen, hydroxyl, $C_1$-$C_6$ alkyl, $C_1$-$C_6$ haloalkyl, $C_1$-$C_6$ alkoxy, $C_1$-$C_6$ haloalkoxy, —CN, nitro, —$COOR^{11}$, —$CONR^aR^b$, substituted or unsubstituted phenyl, and —$NR^aR^b$.

In another embodiment of this aspect, the

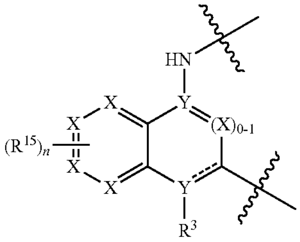

moiety of formula (II) has a formula selected from

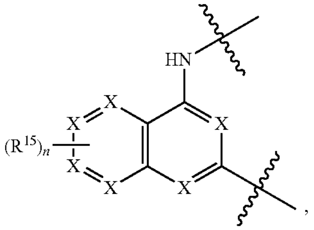

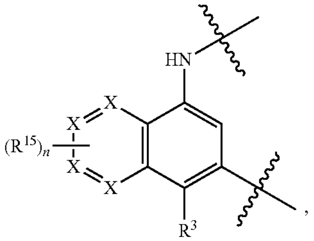

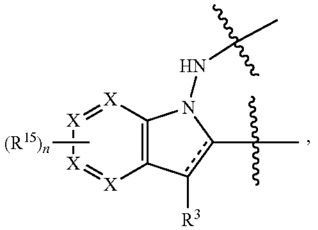

and

-continued

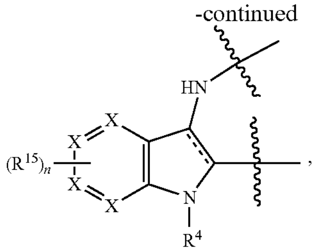

wherein $R^3$ is hydrogen, halogen, hydroxyl, or $NH_2$; and $R^4$ is hydrogen or $NH_2$.

In another embodiment of this aspect, the compound has a formula (IIa)

(IIa)

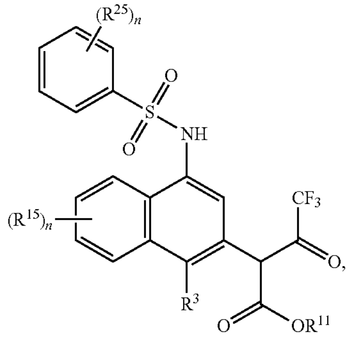

wherein:

$R^3$ is hydrogen, halogen, hydroxyl, $C_1$-$C_6$ alkyl, $C_1$-$C_6$ haloalkyl, $C_1$-$C_6$ alkoxy, $C_1$-$C_6$ haloalkoxy, —$COOR^{11}$, or —$NR^aR^b$;

n at each occurrence is independently 0 or an integer selected from 1 to 4;

$R^{15}$ at each occurrence is independently hydrogen, halogen, hydroxyl, $C_1$-$C_6$ alkyl, $C_1$-$C_6$ haloalkyl, $C_1$-$C_6$ alkoxy, $C_1$-$C_6$ haloalkoxy, —CN, nitro, —$COOR^{11}$, —$CONR^aR^b$, and —$NR^aR^b$;

$R^{25}$ at each occurrence is independently hydrogen, halogen, hydroxyl, $C_1$-$C_6$ alkyl, $C_1$-$C_6$ haloalkyl, $C_1$-$C_6$ alkoxy, $C_1$-$C_6$ haloalkoxy, —CN, nitro, —$COOR^{11}$, —$CONR^aR^b$, substituted or unsubstituted phenyl, and —$NR^aR^b$;

$R^{11}$ at each occurrence is independently hydrogen, $C_1$-$C_6$ alkyl, or benzyl; and $R^a$ and $R^b$ are each independently hydrogen or $C_1$-$C_6$ alkyl.

As a person of ordinary skill in the art would appreciate, any combinations of the embodiments described above with respect to the various moieties of formula (II) are within the scope of the disclosure.

In another embodiment of this aspect, the compound is

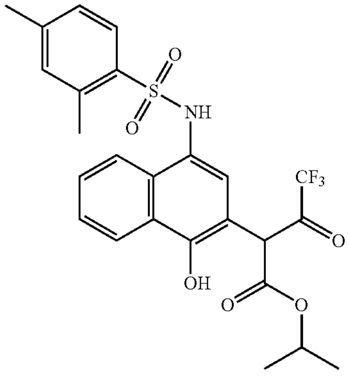 [SMILES: Cc1ccc(S(=O)(=O)Nc2cc(C(C(=O)OC(C)C)C(=O)C(F)(F)F)c(O)c3ccccc23)c(C)c1]

(LH602).

In another embodiment of this aspect, the disease or disorder is selected from cancer, diabetes, Alzheimer's, and Parkinson's, or a disease or disorder caused by oxidative stress and inflammation.

In another aspect, the present invention provides compounds of formula (Ia):

(Ia)

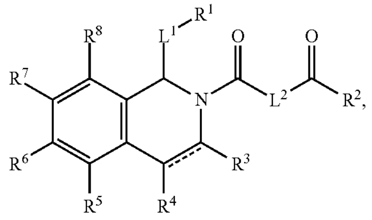

or a stereoisomer, a prodrug, or a pharmaceutically acceptable salt or solvate thereof, wherein:

"$=\!=$" is a single or double bond;

$L^1$ is —$[C(R^{10})_2]_i$—, wherein $R^{10}$ at each occurrence is independently hydrogen, halogen, $C_1$-$C_4$ alkyl, and i is 1, 2, or 3;

$L^2$ is —$[C(R^{20})_2]_j$—, $C_3$-$C_8$ cycloalkylene, $C_6$-$C_{10}$ arylene, 5- to 10-membered heteroarylene, 5- to 10-membered heterocyclylene, wherein $R^{20}$ at each occurrence is independently hydrogen, halogen, or $C_1$-$C_4$ alkyl, and j is an integer selected from 1 through 6;

$R^1$ is selected from

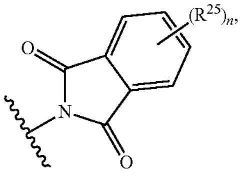

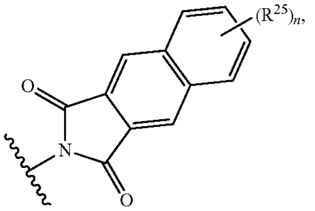

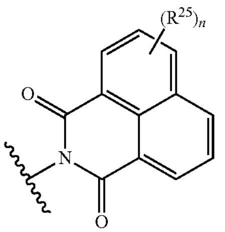

,

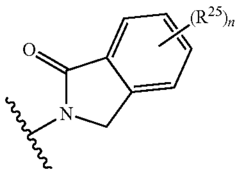

,

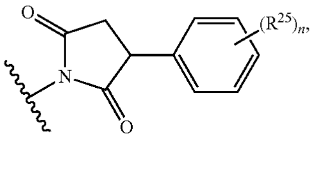

-continued

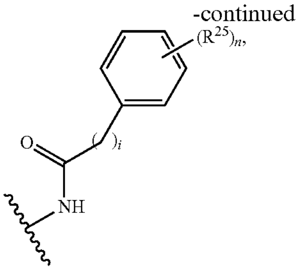

and (i = 1, 2, or 3)

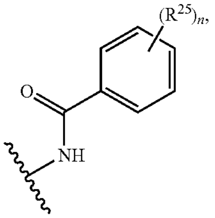

wherein n at each occurrence is independently 0 or an integer from 1 to 4, and $R^{25}$ at each occurrence is independently hydrogen, halogen, hydroxyl, $C_1$-$C_6$ alkyl, $C_1$-$C_6$ haloalkyl, $C_1$-$C_6$ alkoxy, $C_1$-$C_6$ haloalkoxy, —CN, nitro, —$COOR^{11}$, —$CONR^aR^b$, substituted or unsubstituted $C_6$-$C_{10}$ aryl, and —$NR^aR^b$;

$R^2$ is —$OR^9$ or —$NR^aR^b$;

$R^3$ through $R^8$ are each independently hydrogen, halogen, hydroxyl, $C_1$-$C_6$ alkyl, $C_1$-$C_6$ haloalkyl, $C_1$-$C_6$ alkoxy, $C_1$-$C_6$ haloalkoxy, $C_3$-$C_8$ cycloalkyl, $C_6$-$C_{10}$ aryl, 5- to 10-membered heteroaryl, 5- to 10-membered heterocyclyl, —CN, nitro, —$COOR^{11}$, or —$NR^aR^b$;

$R^9$ at each occurrence is independently hydrogen or $C_1$-$C_6$ alkyl;

wherein any said cycloalkyl, or heterocyclyl is optionally substituted by one or more substituents independently selected from halogen, hydroxyl, $C_1$-$C_6$ alkyl, $C_1$-$C_6$ haloalkyl, $C_1$-$C_6$ alkoxy, $C_1$-$C_6$ haloalkoxy, —CN, nitro, oxo, —$COOR^{11}$, and —$NR^aR^b$;

each said aryl or heteroaryl is optionally substituted by one or more substituents independently selected from halogen, hydroxyl, $C_1$-$C_6$ alkyl, $C_1$-$C_6$ haloalkyl, $C_1$-$C_6$ alkoxy, $C_1$-$C_6$ haloalkoxy, —CN, nitro, —$COOR^{11}$, and —$NR^aR^b$;

$R^a$ and $R^b$ are each independently hydrogen or $C_1$-$C_6$ alkyl; and $R^{11}$ at each occurrence is independently hydrogen or $C_1$-$C_6$ alkyl;

provided that the compound of formula (I) is not

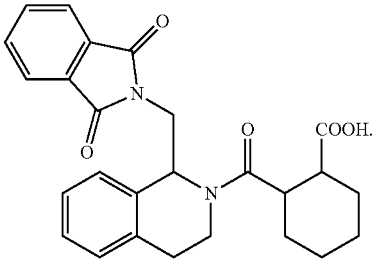 [SMILES: O=C(O)C1CCCCC1C(=O)N1CCc2ccccc2C1CN1C(=O)c2ccccc2C1=O]

In one embodiment of this aspect, in the compound of formula (Ia):

"$==$" is a single bond;

$L^1$ is —$(CH_2)_i$—, wherein i is 1 or 2; and $L^2$ is —$(CH_2)_j$— (j is 1, 2, or 3) or $C_3$-$C_8$ cycloalkylene.

In another embodiment of this aspect, the compound of formula (Ia) is defined as follows:

"$==$" is a single bond;

$L^1$ is —$(CH_2)_i$—, wherein i is 1 or 2;

$L^2$ is —$(CH_2)_j$— (j is 1, 2, or 3) or $C_3$-$C_8$ cycloalkylene;

$R^1$ is selected from

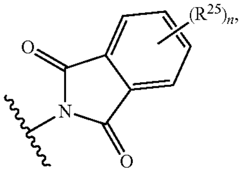

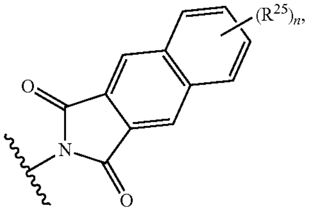

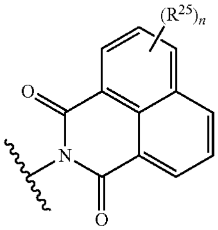

,

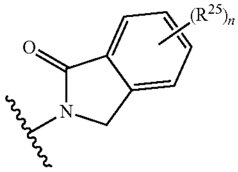

,

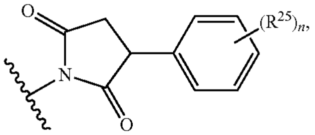

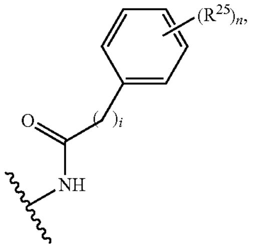

and (i = 1, 2, or 3)

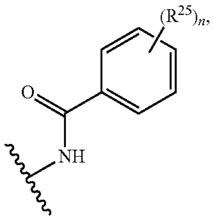

wherein n at each occurrence is independently 0 or an integer from 1 to 4, and $R^{25}$ at each occurrence is independently hydrogen, halogen, hydroxyl, $C_1$-$C_6$ alkyl, $C_1$-$C_6$ haloalkyl, $C_1$-$C_6$ alkoxy, $C_1$-$C_6$ haloalkoxy, —CN, nitro, —$COOR^{11}$, —$CONR^aR^b$, substituted or unsubstituted phenyl, and —$NR^aR^b$;

$R^2$ is —$OR^9$ or —$NH^2$;

$R^3$ through $R^8$ are each independently hydrogen, halogen, hydroxyl, $C_1$-$C_6$ alkyl, $C_1$-$C_6$ haloalkyl, $C_1$-$C_6$ alkoxy, $C_1$-$C_6$ haloalkoxy, $C_6$-$C_{10}$ aryl, nitro, —CN, or —$NR^aR^b$;

$R^9$ at each occurrence is independently hydrogen, $C_1$-$C_6$ alkyl, or benzyl; and $R^a$ and $R^b$ are each independently hydrogen or $C_1$-$C_6$ alkyl.

In another embodiment of this aspect, the compound of formula (Ia) is defined as follows:

"$\equiv$" is a single bond;

$L^1$ is —$CH_2$— or —$(CH_2)_2$—;

$L^2$ is —$(CH_2)_j$— (j=1, 2, or 3), cyclohexylene, or cyclopentylene;

$R^1$ is selected from

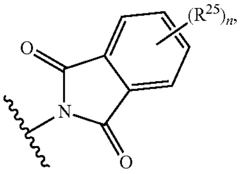

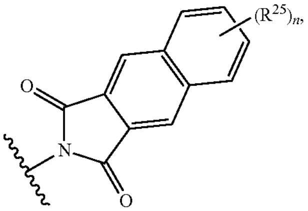

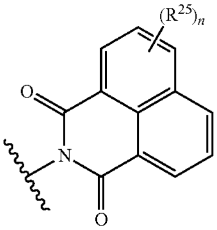

,

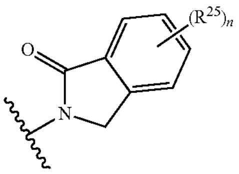

,

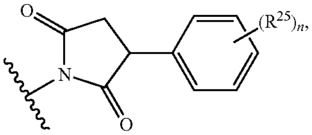

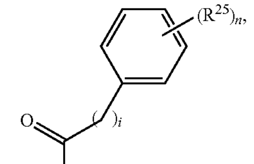

(i = 1, 2, or 3)

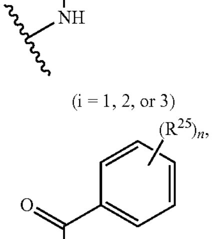

and

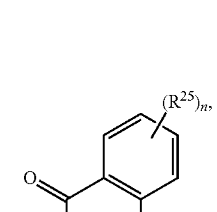

wherein n at each occurrence is independently 0, 1, or 2; and $R^{25}$ at each occurrence is independently halogen, hydroxyl, $C_1$-$C_6$ alkyl, $C_1$-$C_6$ haloalkyl, $C_1$-$C_6$ alkoxy, $C_1$-$C_6$ haloalkoxy, —CN, nitro, —$COOR^{11}$, phenyl, and —$NR^aR^b$;

$R^2$ is —$OR^9$;

$R^3$ and $R^4$ are each hydrogen;

$R^5$ through $R^8$ are each independently hydrogen, halogen, hydroxyl, $C_1$-$C_6$ alkyl, $C_1$-$C_6$ haloalkyl, $C_1$-$C_6$ alkoxy, $C_1$-$C_6$ haloalkoxy, phenyl, or —$NR^aR^b$;

$R^9$ is hydrogen; and $R^a$ and $R^b$ are each independently hydrogen or $C_1$-$C_6$ alkyl.

In another embodiment of this aspect, the compound of formula (Ia) is defined as follows:

"$\equiv$" is a single bond;

$L^1$ is —$CH_2$— or —$(CH_2)_2$—;

$L^2$ is —$(CH_2)_2$—, —$(CH_2)_3$—,

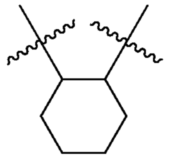

or

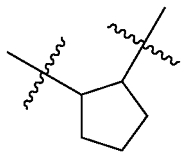

;

$R^1$ is selected from:

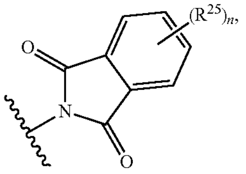

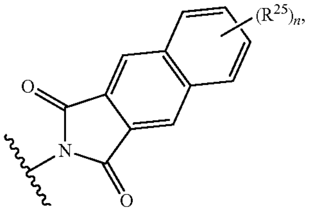

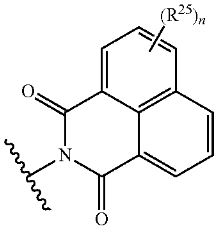

,

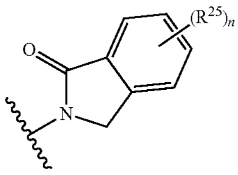

,

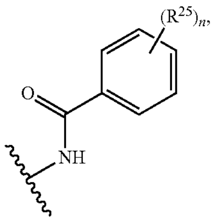

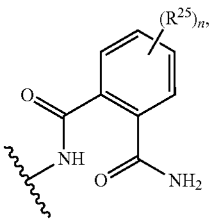

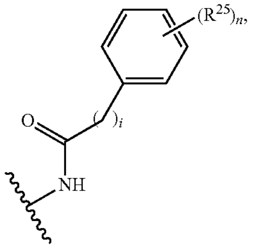

(i = 1, 2, or 3)

-continued

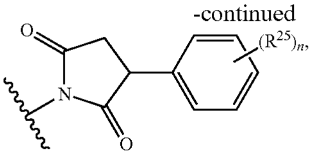

wherein n is 0 or 1; and $R^{25}$ is selected from H, F, Cl, Br, -Ph, —$NO_2$, —$NH_2$, $C_1$-$C_4$ alkyl, and —$CO_2H$;

$R^2$ is —OH, —$OCH_3$, —$OCH_2Ph$, or —$NH_2$;

$R^3$ and $R^4$ are each hydrogen; and $R^5$ through $R^8$ are each independently hydrogen, F, Cl, Br, OMe, —$NO_2$, or —$NH_2$.

In another embodiment of this aspect, the compound of formula (Ia) is defined as follows:

“==” is a single bond;

$L^1$ is —$CH_2$—;

$L^2$ is

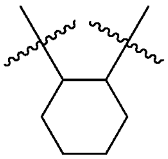

or

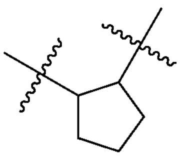

;

$R^1$ is selected from:

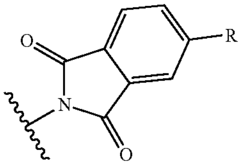

(R=H, F, Br, or -Ph),

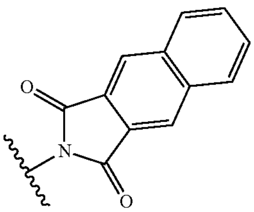

,

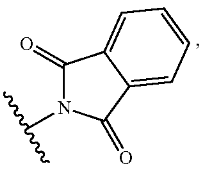

,

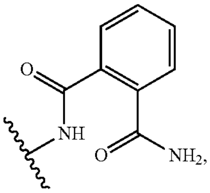

and

-continued

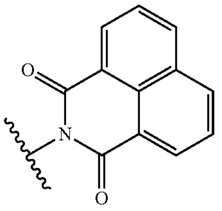

;

$R^2$ is —OH;

$R^3$ and $R^4$ are each hydrogen; and $R^5$ through $R^8$ are each independently hydrogen, F, —OMe, or —$NH_2$.

In another embodiment of this aspect, the compound of formula (Ia) is selected from the group consisting of:

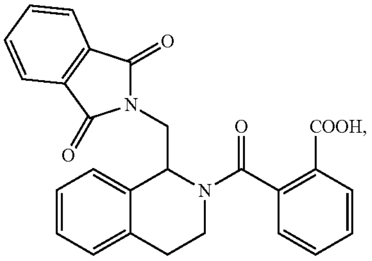

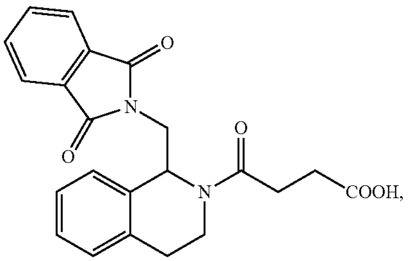

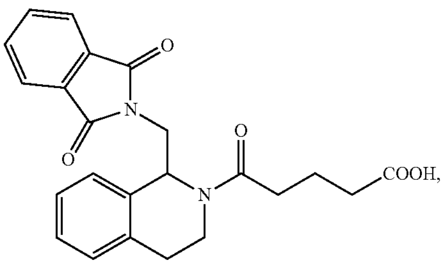

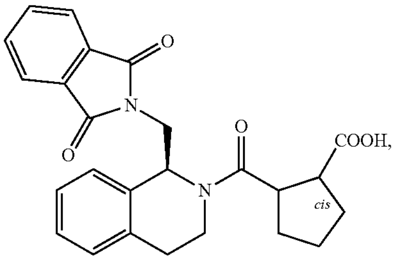

-continued
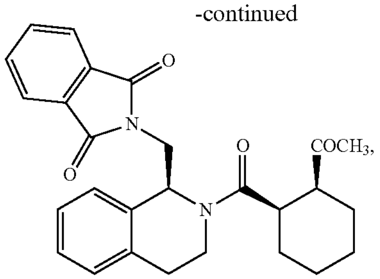
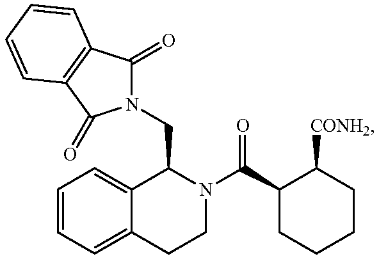
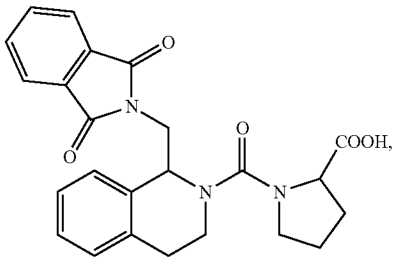
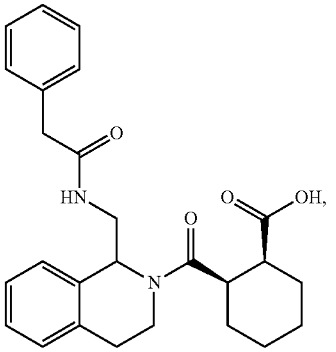
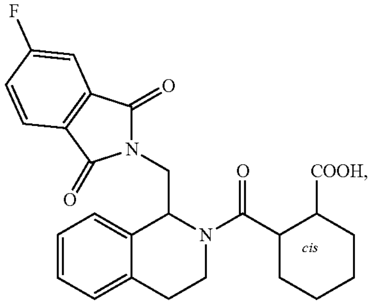
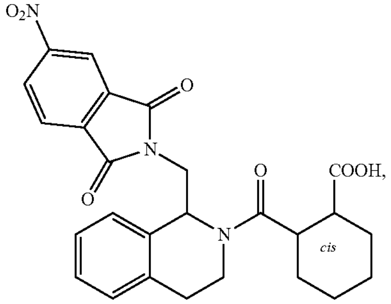
-continued
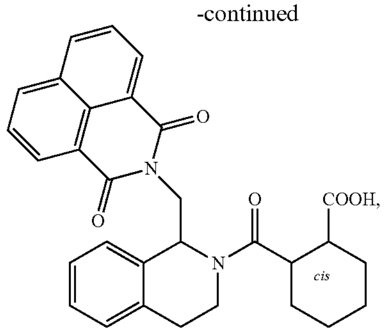
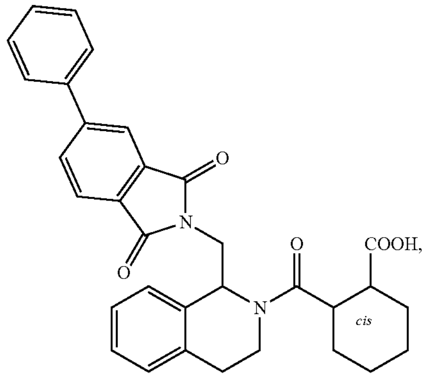
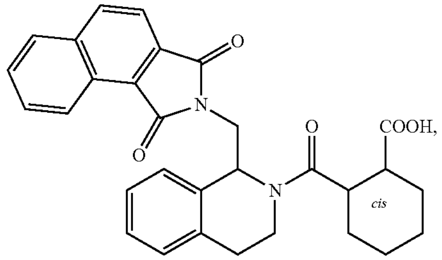
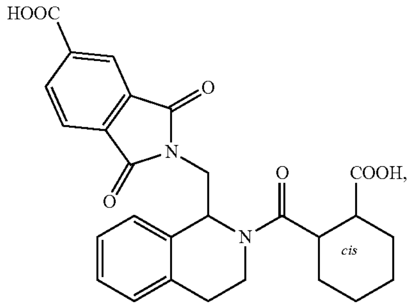
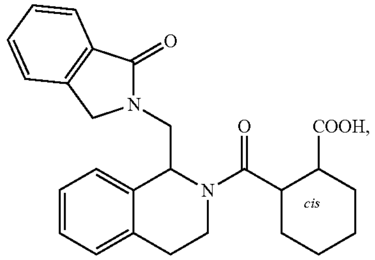

-continued
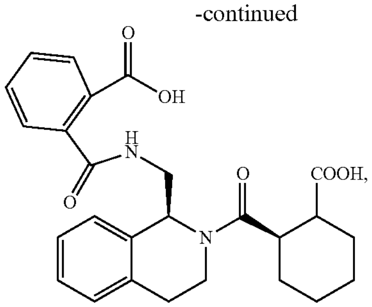
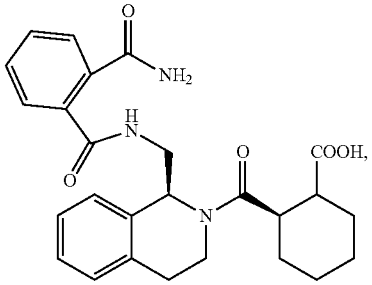
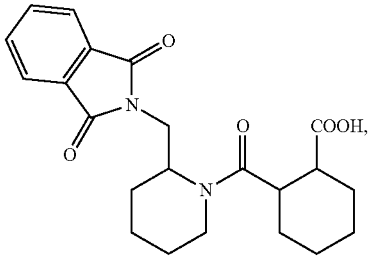
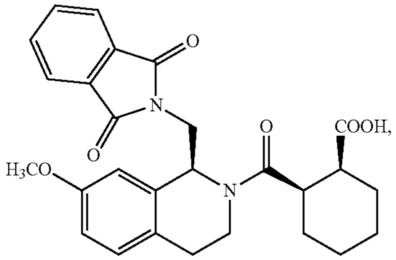
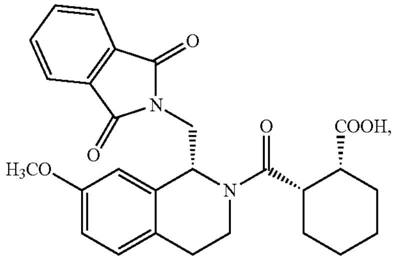
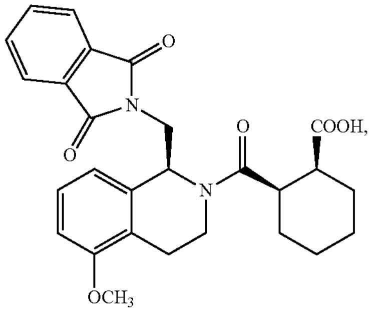
-continued
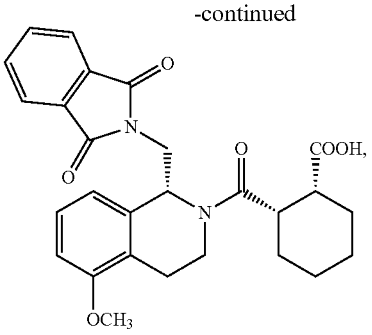
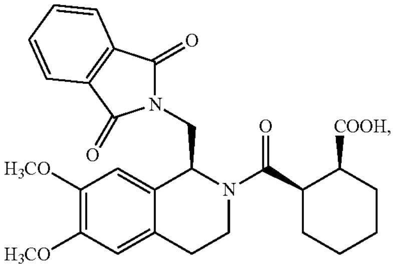
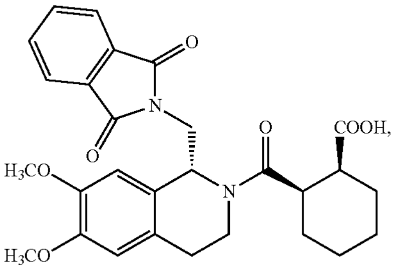
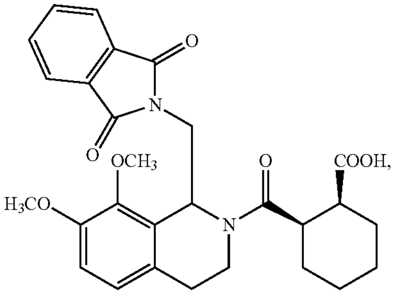
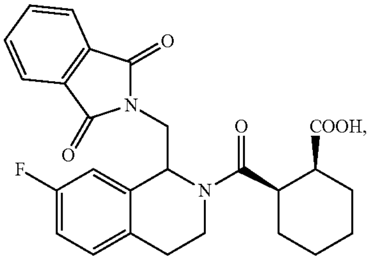
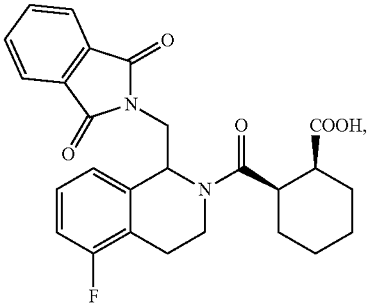

-continued
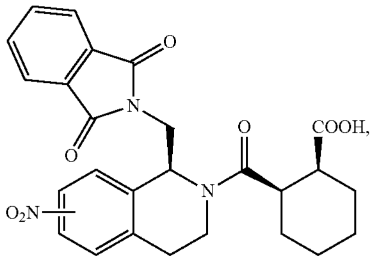
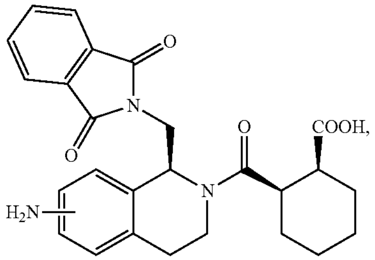
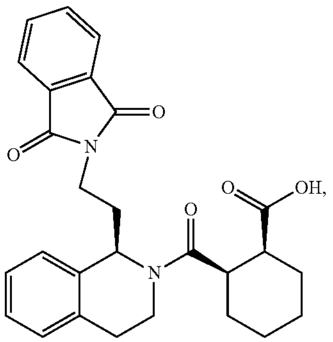
and
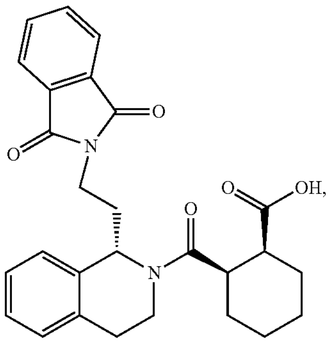
or a stereoisomer, a prodrug, or a pharmaceutically acceptable salt or solvate thereof.
In one embodiment of this aspect, the present invention provides a substantially enantiomerically pure compound selected from the group consisting of:
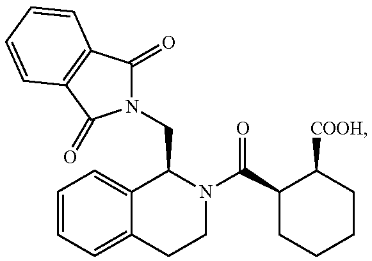
-continued
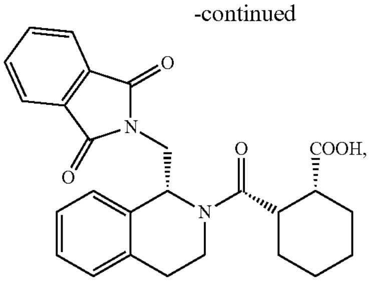
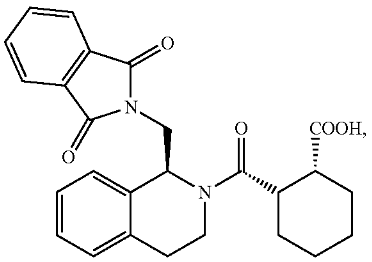
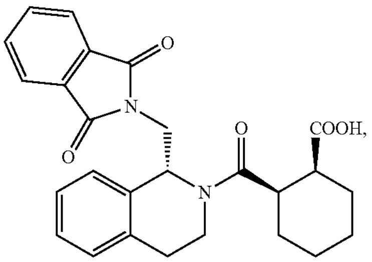
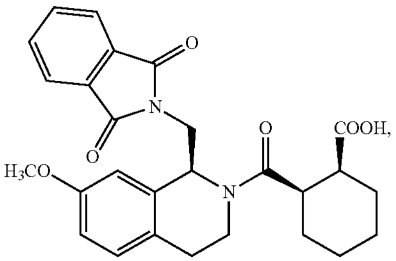
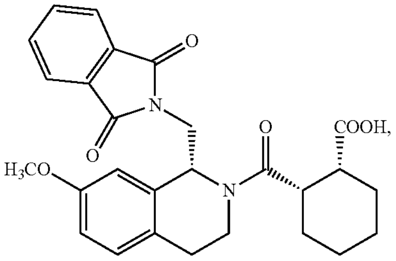
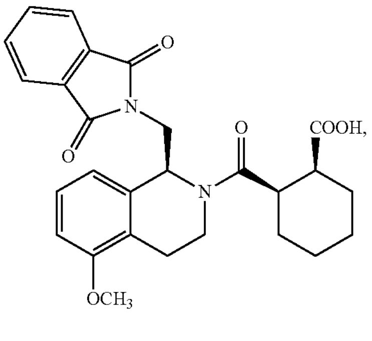

-continued

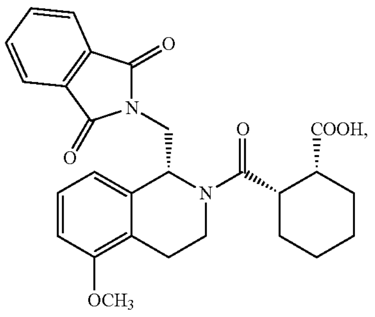

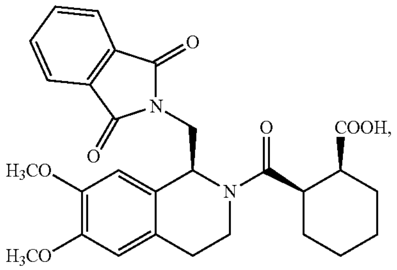

and

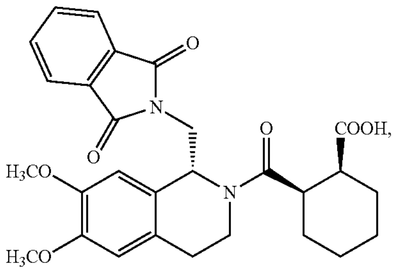

or a prodrug, a pharmaceutically acceptable salt or solvate thereof.

In a preferred embodiment, the substantially enantiomerically pure compound is selected from:

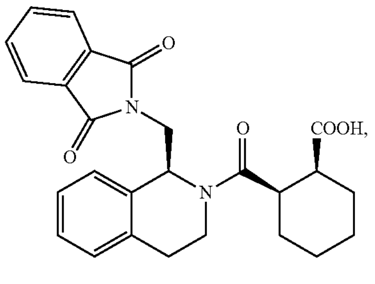

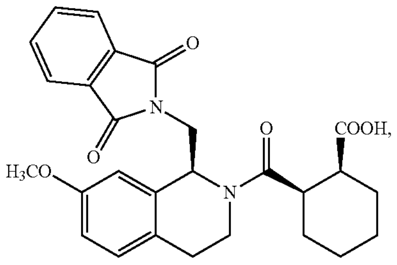

-continued

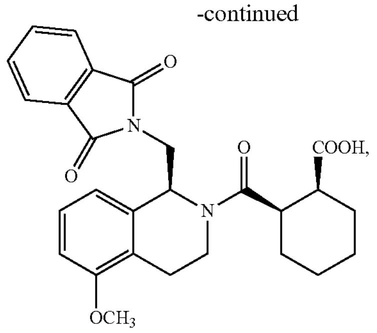

and

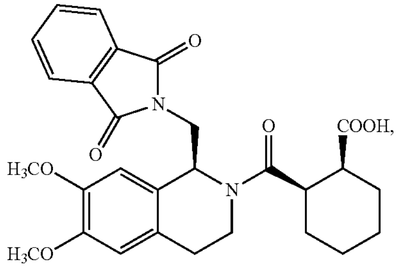

or a stereoisomer, a prodrug, or a pharmaceutically acceptable salt or solvate thereof.

In another aspect, the present invention provides a compound according to any embodiments described above for use in the treatment of an inflammatory disease or disorder associated with Keap1-Nrf2 interaction, including but not limited to cancers, diabetes, Alzheimer's, Parkinson's, or a disease caused by oxidative stress and inflammation In another aspect, the present invention provides a composition comprising a compound according to any of the embodiments described above, and a pharmaceutically acceptable carrier.

In another aspect, the present invention provides a method of treating a disease or disorder associated with Keap1-Nrf2 interaction, comprising administering to a subject in need thereof a therapeutically effective amount of the compound according to any of the embodiments described.

In another aspect, the present invention provides a method of treating a disease or disorder associated with Keap1-Nrf2 interaction, comprising administering to a subject in need thereof a composition comprising a therapeutically effective amount of a compound according to any of the embodiments described above.

In another aspect, the present invention provides use of a compound according to any of the embodiments described above in the manufacture of a medicament for treatment of an inflammatory disease or disorder associated with Keap1-Nrf2 interaction.

In any of the aspects or embodiments described above, the disease or disorder can include any diseases or disorders associated with Keap1-Nrf2 interaction and/or caused by oxidative stress and inflammation, including, but not limited to cancer, diabetes, Alzheimer's, Parkinson's.

In another aspect, the present invention provides a method of identifying a lead or candidate compound useful for developing small-molecule therapeutic agents for treatment of inflammatory diseases or conditions associated with Keap1-Nrf2 protein-protein interaction, comprising screening a plurality of compounds against a Keap1-Nrf2 interaction target using an assay selected from FP, TR-FRET, and SPR-based solution competition assays.

In one embodiment of this aspect, the method of identifying a lead or candidate compound contains the steps of:

(a) incubating a library of compounds with a Keap1 Kelch domain in a culture medium in parallel at a pre-determined concentration of the compounds for a period of time;

(b) measuring concentrations of unbound Keap1 Kelch domain for the compounds screened using SA chip immobilized with biotin-16mer Nrf2 peptide (300 RU);

(c) calculating percent inhibitions of the compounds to the Keap1-Nrf2 interaction based on the concentrations of unbound Keap1 Kelch domain; and (d) selecting compounds having a percent inhibition of at least 20%, at least 30%, at least 40%, or at least 50% at a pre-determined concentration of the compounds in the range of between 1 μM and 50 μM.

In another embodiment of this aspect, the compound is screened at a pre-determined concentration of 5 μM and 50 μM, and the percent inhibition target is at least 50%.

In another embodiment of this aspect, the method further includes steps of:

(e) evaluating selected compounds from step (d) in cell-based ARE β-lactamase reporter assay using CellSensor HepG2 cell line; and (f) selecting compounds from step (e) exhibiting an ARE-inducing activity in the CellSensor® ARE-bla Hep G2 cell line with an $EC_{50}$ of less than 20 μM using 150 μM tBHQ as 100%.

In another aspect, the present invention provides eight hit compounds that can be used as leads for optimization to obtain drug candidates for developing into therapeutic agents.

In one embodiment of this aspect, the present invention provides a compound selected from the group consisting of:

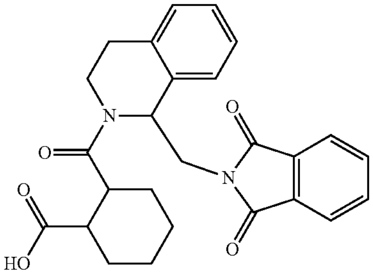
,

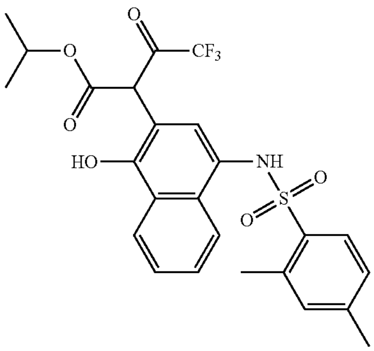
,

-continued

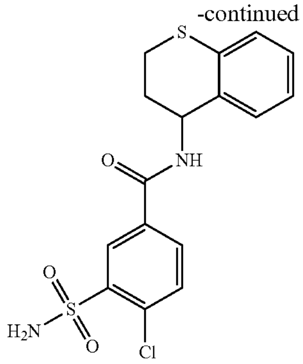
,

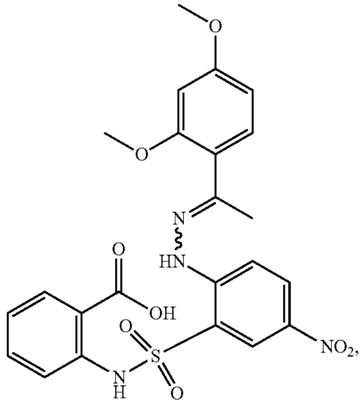

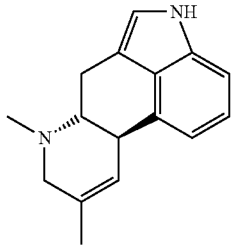
,

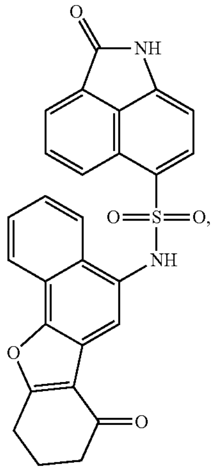

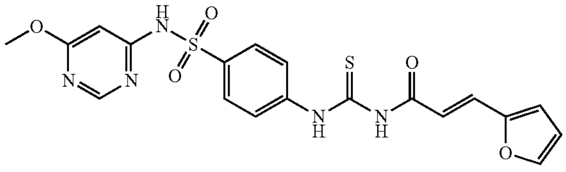
,

-continued

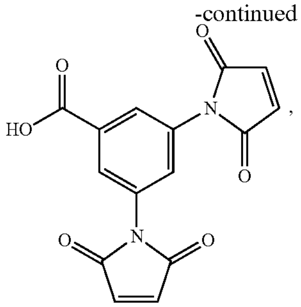

, or an analog, a stereoisomer, a prodrug, or a pharmaceutically acceptable salt or solvate thereof, (a) for use in the treatment of an inflammatory disease or disorder associated with Keap1-Nrf2 interaction, (b) for use as a direct inhibitor to Keap1-Nrf2 protein-protein interaction, or (c) for use as lead for optimization to obtain useful therapeutic agents for Keap1-Nrf2 related diseases or disorders, including but not limited to cancer, diabetes, Alzheimer's, Parkinson's, or a disease or disorder caused by oxidative stress and inflammation.

The compounds of the present invention may be optically active and may be isolated in either their optically active, i.e., enantiomerically enriched, or racemic forms. Cis and trans geometric isomers of the compounds of the present invention may be isolated as a mixture of isomers or as separated isomeric forms and are intended as a disclosed variation. In the present application, all chiral, diastereomeric, racemic forms and all geometric isomeric forms of a structure are intended to be disclosed.

As used herein, "alkyl" is intended to include both branched and straight-chain saturated aliphatic hydrocarbon groups containing 1 to 10 carbons, more preferably 1 to 6 carbons, in the main (longest) chain. The term encompasses, but is not limited to, methyl, ethyl, propyl, isopropyl, butyl, t-butyl, isobutyl, pentyl, hexyl, or the like.

Unless otherwise indicated, the term "cycloalkyl", as used herein alone or as a part of another group, includes saturated cyclic hydrocarbon radical having 3 to 8 carbons forming the ring.

Unless otherwise indicated, the term "aryl", as used herein alone or as part of another group, refers to monocyclic or bicyclic aromatic radical containing 6 to 10 carbons in the ring portion (such as phenyl, benzyl, or naphthyl, including 1-naphthyl and 2-naphthyl).

"Halo" or "halogen" as used herein, refers to fluoro, chloro, bromo, and iodo; and "haloalkyl" is intended to include both branched and straight-chain saturated aliphatic hydrocarbon radicals containing one or more halogen substituents, such as for example $CF_3$ or the like.

Unless otherwise indicated, the term "alkoxyl", as used herein alone or as a part of another group, includes an alkyl group linked to a molecular moiety through an oxygen atom, for example, RO—, where R is alkyl.

Unless otherwise specified, as used herein, the term "heteroaryl" is intended to mean a stable 5- to 10-membered monocyclic or bicyclic, heterocyclic aromatic group which consists of carbon atoms and from 1 to 4 heteroatoms independently selected from the group consisting of N, O and S, and is aromatic in nature, including but not limited to pyridinyl, furyl, pyrimidyl, indolyl, etc.

Unless otherwise specified, as used herein, the term "heterocyclyl" is intended to mean a 5- to 10-membered monocyclic or bicyclic, heterocyclic non-aromatic group which consists of carbon atoms and from 1 to 4 heteroatoms independently selected from the group consisting of N, O and S, including but not limited to piperidinyl, piperazinyl, pyrrolidinyl, tetrhydrofuranyl, etc.

Unless otherwise indicated, substituted "cycloalkyl," "aryl," "heterocyclyl," or "heteroaryl" includes the corresponding groups substituted with from one to five substituents independently selected from halogen, $C_1$-$C_6$ alkyl, $C_1$-$C_6$ alkoxy, $C_1$-$C_6$ haloalkyl, hydroxy, hydroxy-alkyl, $C_1$-$C_6$ acyl, cyano, nitro, and amino group;

The terms "cycloalkylene," "arylene", "heteroarylene", and "heterocyclylene", as used herein, represent the corresponding divalent "cycloalkyl," "aryl", "heteroaryl", and "heterocyclyl" groups, respectively, connected to two other molecular moieties, and may be used exchangeably with the corresponding "cycloalkyl," "aryl", "heteroaryl", and "heterocyclyl" groups, respectively.

The term "cyano" as used herein refers to a —CN group and the two terms are used interchangeably.

The term "nitro" as used herein refers to an $—NO_2$ group and the two terms are used interchangeably.

The term "hydroxy" or "hydroxyl", as used herein, refers to an —OH group and the two terms are used interchangeably.

The term "molecular moiety" or "moieties", as used herein, refers to a portion or portions of a molecule.

The term "bioisosteric groups" or "bioisosteres", or the like, as used herein, refers to substituents or functional groups with similar physical or chemical properties which produce broadly similar biological properties to a chemical compound, as generally understood in medicinal chemistry or pharmaceutical sciences.

The phrase "substantially enantiomerically pure", as used herein, refers to a chiral compound having an enantiomeric excess (ee) of at least 95%, preferably at least 97%, and more preferably at least 99%, and most preferably at least 99.5%.

The phrase "pharmaceutically acceptable" is employed herein to refer to those compounds, materials, compositions, and/or dosage forms which are, within the scope of sound medical judgment, suitable for use in human beings and animals commensurate with a reasonable therapeutic benefit/risk ratio.

As used herein, "pharmaceutically acceptable salts" refer to derivatives of the disclosed compounds wherein the parent compound is modified by making counterpart acid or base salts thereof. Examples of pharmaceutically acceptable salts include, but are not limited to, mineral or organic acid salts of basic residues such as amines; alkali or organic salts of acidic residues such as carboxylic acids; and the like. Pharmaceutically acceptable salts include the conventional non-toxic salts or the quaternary ammonium salts of the parent compound formed, for example, from non-toxic inorganic or organic acids. Moreover the term may refer to counter ions of any moiety that is designated in this disclosure in an ionic form.

In particular, for the compounds having a free carboxylic acid group in the present invention, basic addition salts can be prepared during the final isolation and purification of the compounds by reacting a carboxylic acid group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, ethylenediamine, ethanolamine, diethanolamine, triethanolamine, piperidine, piperazine, 1H-imidazole, choline, lysine, arginine, benethamine, benzathine, betaine, or the like.

The term "prodrug," as used herein, refers to compounds that are transformed in vivo to yield the parent compound of the above formulae, for example, by hydrolysis in blood. Common examples include, but are not limited to, ester and amide forms of a compound having an active form bearing a carboxylic acid moiety.

The term "solvate," as used herein, means a physical association of a compound of this invention with one or more, preferably one to three, solvent molecules, whether organic or inorganic. Exemplary solvates include, but are not limited to, hydrates, ethanolates, methanolates, and isopropanolates. Methods of solvation are generally known in the art.

The term "therapeutically effective amount," as used herein, refers to the total amount of each active component that is sufficient to show a meaningful patient benefit, e.g., a sustained reduction of symptoms.

The compounds of this invention can be administered for any of the uses described herein by any suitable means, for example, orally, such as tablets, capsules (each of which includes sustained release or timed release formulations), pills, powders, granules, elixirs, tinctures, suspensions, syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms.

The dosage regimen for the compounds of the present invention will vary depending upon known factors, such as the pharmacodynamic characteristics of the particular agent and its mode and route of administration; the species, age, sex, health, medical condition, and weight of the recipient; the nature and extent of the symptoms; etc.

By way of general guidance, the daily oral dosage of each active ingredient, when used for the indicated effects, will range between about 0.01 to about 5000 mg per day, preferably between about 0.1 to about 1000 mg per day, and most preferably between about 0.1 to about 250 mg per day.

All terms not specifically defined will take their ordinary meanings known to a person of ordinary skill in the relevant art.

Screening and Assay Methods

This section describes, among others, the approaches to (a) advance two of the eight hits to leads for optimization through chemical synthesis of the hit compounds and activity confirmation in biochemical and cell-based assays, (b) investigate the stereochemical requirement of binding to Keap1 Kelch domain and assign the stereochemistry of active stereoisomers using spectroscopic and crystallographic methods and chemical synthesis, (c) achieve the stereoselective synthesis of the active stereoisomer, and (d) biochemical, in vitro, and in vivo assays.

Figure 2:
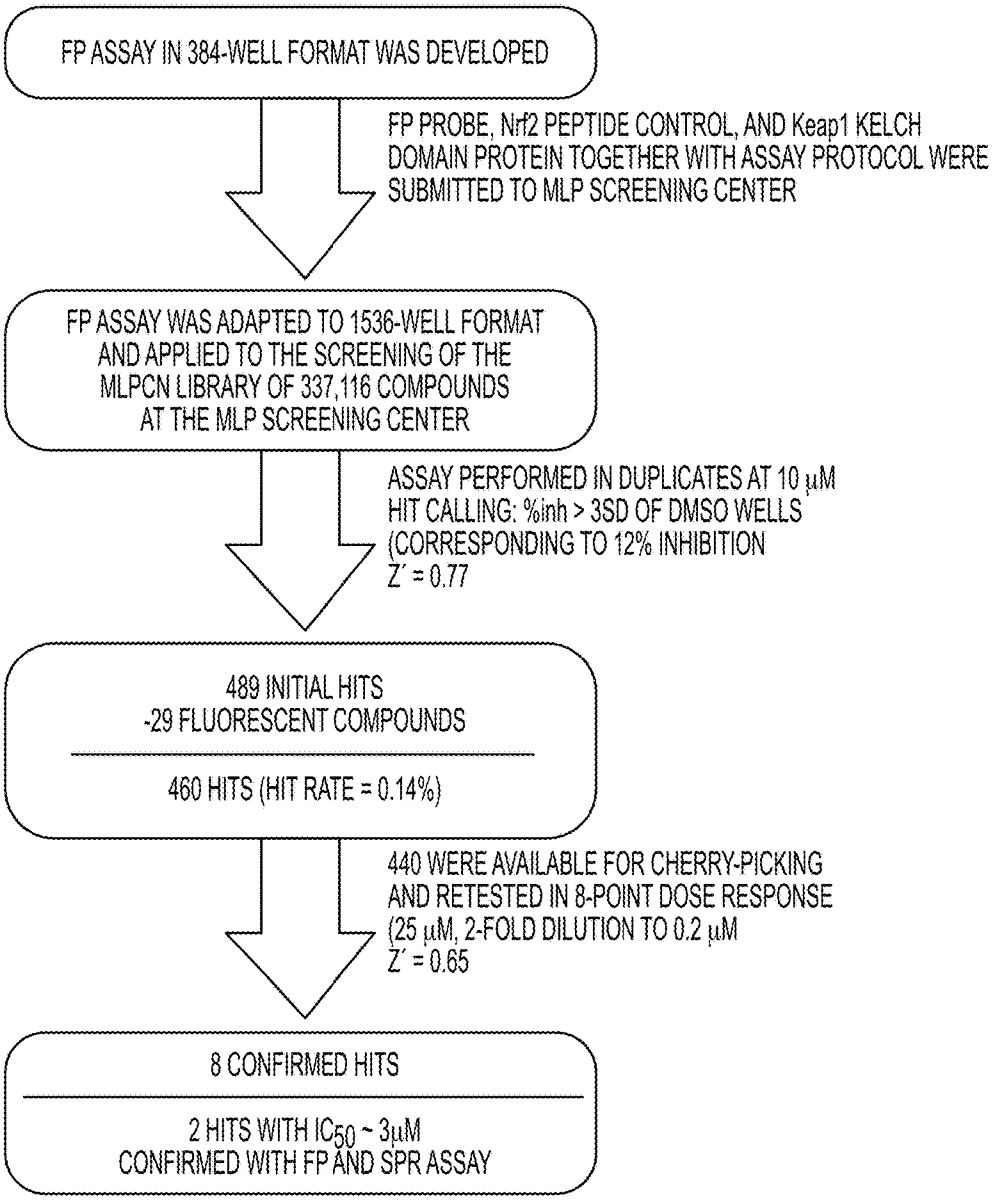
FIG. 2 illustrates HTS screening flowchart of MLPCN (the Molecular Libraries Probe Centers Network) compounds.

Since prior to the present invention, no known small molecule inhibitors of Keap1-Nrf2 interaction could be used as leads, high throughput screening (HTS) assays were used for lead discovery, and fluorescence-based assays using fluorescence polarization (FP) were developed and submitted to the NIH MLP screening center at Broad Institute. The FP assay was applied successfully to the screening of 337,116 compounds. As shown in FIG. 2, using inhibition >3× standard deviation of DMSO wells (corresponding to 12% inhibition) for hit calling, the primary screen at 10 μM generated a list of 489 hits. After excluding fluorescent compounds, 440 of the initial hits were cherry-picked and retested in the FP assay for 8-point dose-response curves. In the retest, eight were confirmed hits and two were shown to have 3 μM IC50 in the FP assay and 1.6-1.9 μM Kd in the SPR assay. All 8 hits can serve as leads for further optimization. The two potent hits were used as leads for optimization through chemical resynthesis and activity confirmation of the hit compounds and analogs. The stereochemical requirements of binding to Keap1 Kelch domain were investigated, and the stereochemistry of active stereoisomer was assigned using X-ray crystallography and stereoselective synthesis. Simple amide bond coupling between the optically active (S)-4 and (R,S)-10 produces the benzyl protected (SRS)-11, which upon hydrogenolysis gives the desired enantiomer (SRS)-5 (LH601A).

Hit Identification and Confirmation

Figure 3A:
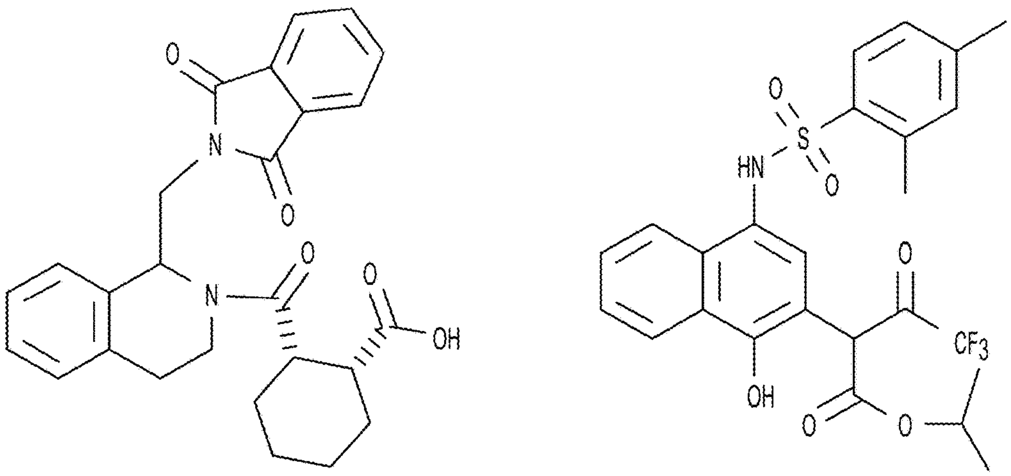
FIG. 3A illustrates the structures of two hits (LH601 and LH602) identified through HTS.
Figure 3B:
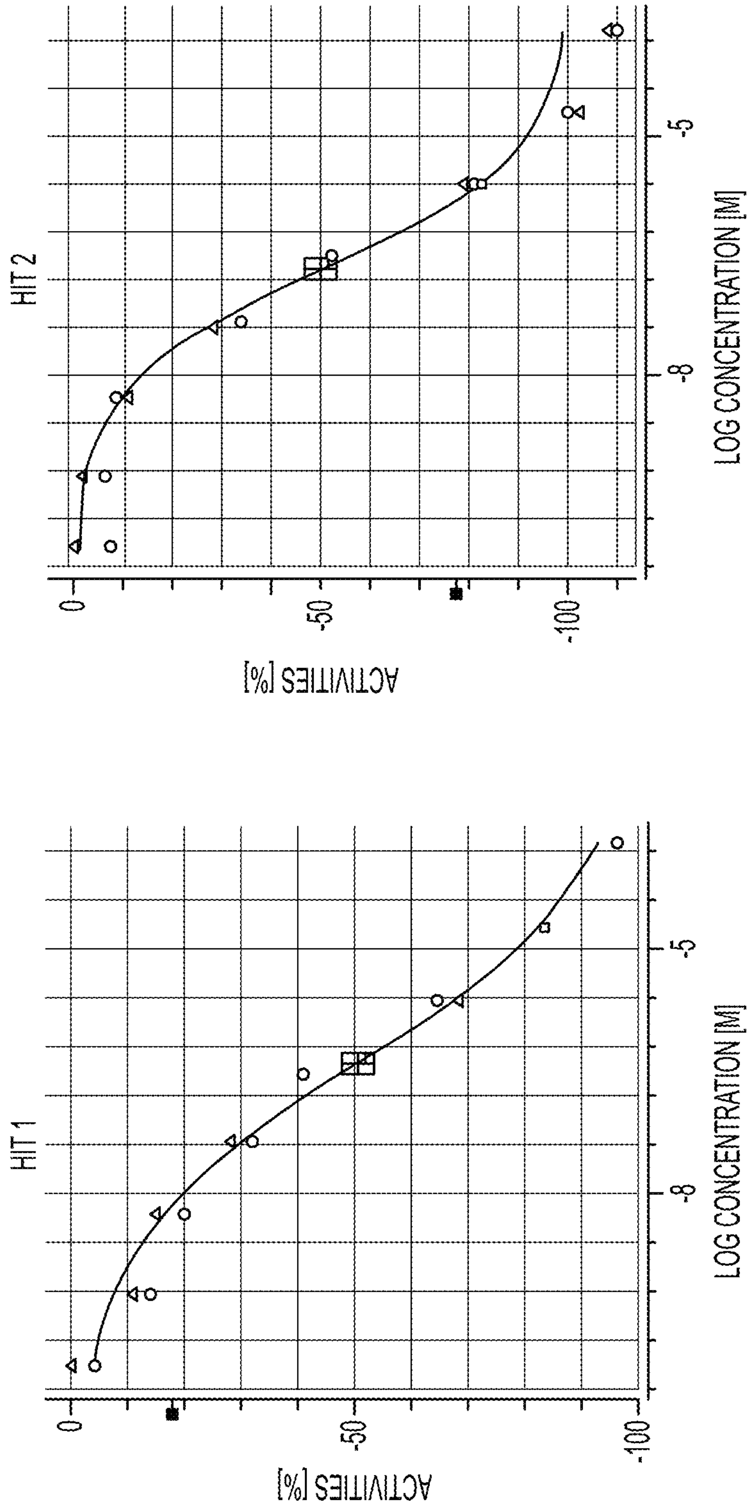
FIG. 3B illustrates dose-response curves of the two hits in the confirmative FP assay.
Figure 3C:
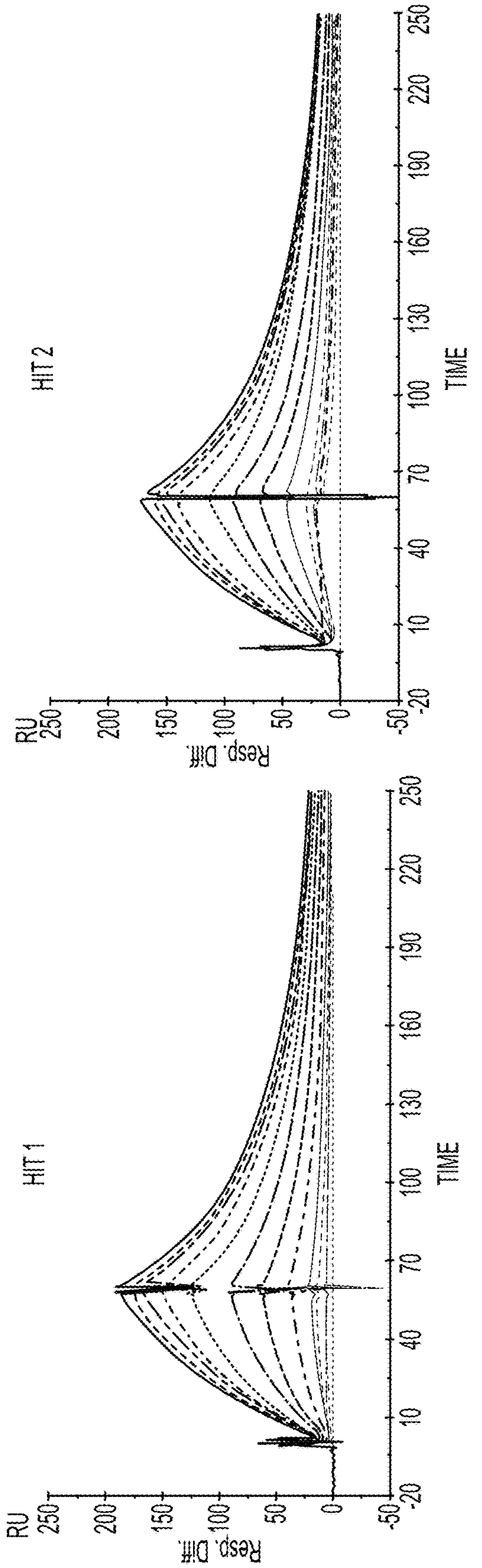
FIG. 3C illustrates sensorgrams of two hits in the SPR assay.
Figure 3D:
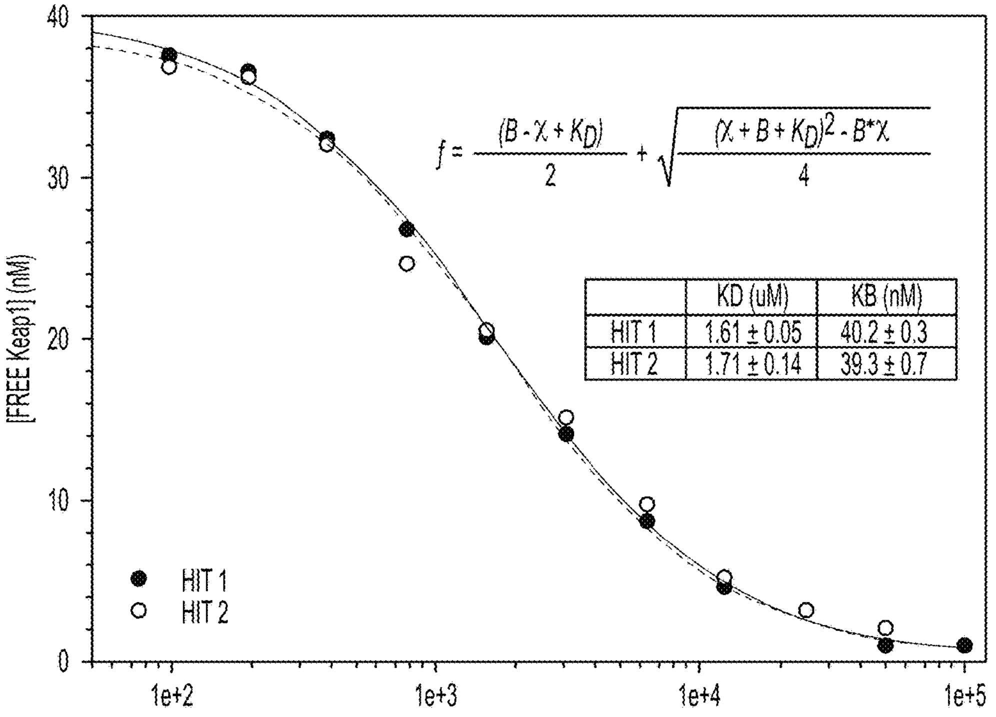
FIG. 3D illustrates the curve-fitting of the sensorgram data shown in C to derive the $K_d$ for the two hits.

We developed three biochemical assays including two fluorescence-based assays (FP and TR-FRET) and a SPR-based solution competition assay to discover and confirm hits from chemical libraries. Our FP assay was used to screen the MLPCN library of 337,116 compounds (PubChem Assay ID: 504523, 504540). Two of the eight hits confirmed have 3 μM $IC_{50}$. FIG. 3A shows the structures of the two potent hits and FIG. 3B shows the FP assay dose-response curves demonstrating their 3 μM $IC_{50}$. The Keap1-binding activity of the two potent hits was confirmed in our SPR assay with $K_d$ between 1.6 and 1.9 μM as shown in FIGS. 3C and 3D.

FP Assay Protocol for HTS:

Human Keap1 Kelch domain protein was cloned into expression vector pET15b and transformed into *E. coli* BL21 (DE3) strain. The protein was purified through Ni-NTA affinity column. Purified protein was stored in the buffer containing 20 mM HEPES (pH7.4), 5 mM DTT at −80° C.

Solution Preparation (for a Run of 135 Plates):

1) 1100 mL of 20 nM FITC-9mer-Nrf2-$NH_2$ was prepared by taking 2.689 mL of 8.18 μM FITC-9mer-Nrf2-NH2 in 100% DMSO in 1100 ml FP buffer (10 mM HEPES, pH 7.4, 3.4 mM EDTA, 150 mM NaCl, 0.005% Tween-20). 2) 60 mL of 8 μM Ac-9mer-Nrf2 was prepared by taking 0.48 mL of 1 mM Ac-9mer-Nrf2 in 100% DMSO in 60 mL FP buffer 3) 500 mL of 400 nM Keap1 Kelch domain was prepared by taking 9 mL of 0.75 mg/mL Keap1 Kelch domain in 500 mL FP buffer.

Final Concentration for FP Assay:

10 nM FITC-9mer-Nrf2-NH2, 100 nM Kelch Kelch domain.

Final Concentration for Positive Control:

2 uM Ac-9mer-Nrf2-$NH_2$

Setup Reagents on Automation Instrument:

1) the solutions of Ac-9mer-Nrf2-$NH_2$, Keap1 Kelch domain, and FP buffer were added to the bottles of BioRaptr (Beckman) based on the dispense table; 2) FITC-9mer-Nrf2-NH2 solution was added to the bottle of combi NL (Thermo Scientific)

Run Automation Protocol:

1) 4 uL/well of the solutions from BioRaptr was dispensed based on the dispense table to 1536-well ARPs (Aurora, Cat#: 00019180BX) (Positive control wells receive 2 uL/well of Ac-9mer-Nrf2 and 2 uL/well of Keap1 Kelch solution; all the other wells received 2 uL/well of FP buffer and 2 uL/well of Keap1 Kelch solution); 2) the plates were incubated for 10 min at 25° C.; 3) 4 ul/well of 20 nM FITC-9mer-Nrf2-NH2 solution was dispensed to the plates by Combi NL; 4) the plates were incubated for 60 min at 25° C.; and 5) the plates were read on ViewLux (PerkinElmer) with excitation wavelength of 480 nm and emission wavelength of 535 nm with dichroic mirror of D505fp/D535.

FP assay dose-response retest was performed using the same FP assay protocol above for HTS with the exception that the compound concentration started at 25 μM with 2-fold dilution for 8 points (25-0.2 μM) in duplicate.

Thermal Shift Assay Protocol:

The fluorescence-based thermal shift assay was developed using the standard protocol to confirm the ligand-binding affinity of hit compounds by assessing the shift of the unfolding temperature (DT) obtained in the presence of varying concentrations of the inhibitor.

SPR Assay Protocol:

Streptavidin (200 μg/mL) was immobilized on Fc1 and Fc2 following the general procedure to obtain surface immobilization level of ~7000 RU. Biotinylated 16mer Nrf2 peptide was diluted into the running buffer to obtain 10 nM solution, which was injected through Fc2 at a flow rate of 10 μL/min to saturate the sensor chip surface. An immobilization level of 300 RU for 16mer Nrf2 peptide was achieved in Fc2 and the free streptavidin at Fc1 of the chip was used as the blank.

To construct a standard curve for the measurement of the unbound Keap1 Kelch domain protein concentration, a stock of Keap1 Kelch domain was diluted serially 2-fold in the running buffer to obtain as standards 6 concentrations of Keap1 Kelch domain ranging from 125 nM to 4 nM. Each solution of Keap1 Kelch domain was injected through Fc1 and Fc2 with a 1-min association time and a 3-min dissociation time at 25° C. and a flow rate of 50 μL/min. The sensor chip surface was regenerated with NaCl (1 M) at a flow rate of 100 μL/min for 1 min followed by two consecutive 1-min washes with the running buffer at a flow rate of 100 μL/min. To generate the standard curve, double subtractions from the reference surface (Fc1) and the blank were performed to the sensorgrams obtained at varying concentrations of Keap1 Kelch domain. The slopes of the initial association phase from the corrected SPR sensorgrams were calculated by fitting to the linear model in BIAevaluation software 4.1 and plotted against the concentration of Keap1 Kelch domain protein.

Solution competition assays were performed under the same conditions at 40 nM Keap1 Kelch domain concentration in the presence of varying concentrations of Nrf2 protein or a Nrf2 peptide ranging between 1 nM and 1 μM in 2-fold increments. The initial slopes from sensorgrams obtained at a given total concentration of Keap1 Kelch domain in the presence of varying concentrations of Nrf2 protein or a Nrf2 peptide were used to calculate the concentration of unbound Keap1 Kelch domain protein. The fraction of bound Keap1 Kelch domain protein (fb) at a given total concentration of Keap1 Kelch domain was then plotted against the concentrations of the Nrf2 protein or Nrf2 peptide and used to derive its corresponding KD using the following quadratic equation:

$$f_b = \frac{(Lt + x + K_D) - \sqrt{(Lt + x + K_D)2 - 4xLt}}{2Lt}$$

where Lt is the total concentration of Keap1 Kelch domain and fb is the fraction of the Keap1 Kelch domain protein bound at a given concentration (x) of Nrf2 protein or Nrf2 peptide.

Activity Evaluation

Figure 4A:
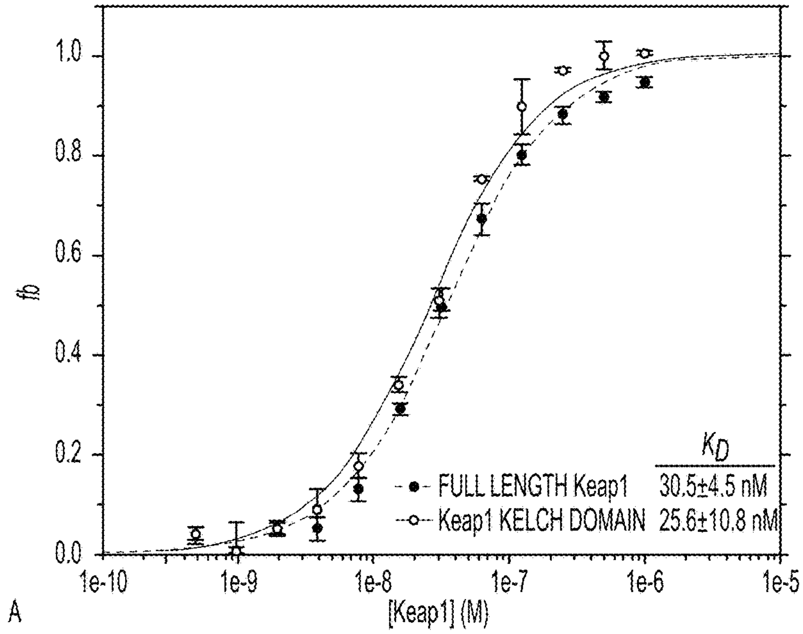
FIG. 4A illustrates a comparison of binding of FITC-9mer-Nrf2-$NH_2$ to the Keap1 Kelch domain and to the full length Keap1 protein.
Figure 4B:
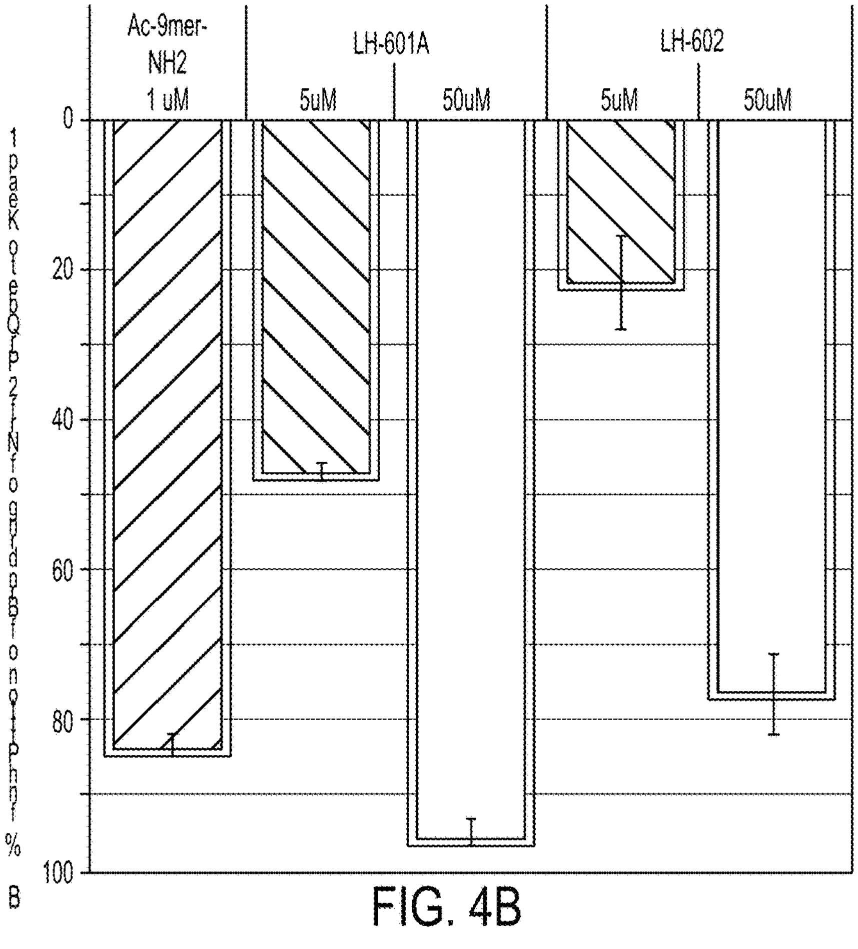
FIG. 4B illustrates similar % inhibition of binding of FITC-9mer-Nrf2-$NH_2$ to the full length Keap1 protein for the two leads LH601A and LH602 as compared to their inhibition of binding of FITC-9mer-Nrf2-$NH_2$ to the Keap1 Kelch domain.

It should be noted that the direct inhibitors identified using Keap1 Kelch domain also bind to the full length Keap1 protein with similar affinity and are capable of disrupting the protein-protein interaction between full length Keap1 and Nrf2 as shown in FIG. 4. Thus, the activity observed with Keap1 Kelch domain represents the activity for the full length Keap1. Besides fluorescence-based and SPR-based biochemical assays for measuring direct inhibition of Keap1-Nrf2 protein-protein interaction, we have used cell-based assays, including the ARE-luciferase reporter assays in HepG2 and SW480 cell lines, in the evaluation of various isothiocyanates and curcumin analogs. The activity of LH601A, LH602, and their simple analogs in cell-based assays has also helped guide our lead optimization efforts.

Considering the presence of three chiral centers and structure flexibility within LH601 stereoisomers, we have used stereoselective synthesis and single-crystal X-ray crystallography to confirm the stereochemistry of LH601A.

TABLE 1

Comparison of the two leads[a]

| | Lead 1 (LH601A) | Lead 2 (LH602) |
|---|---|---|
| Structure | 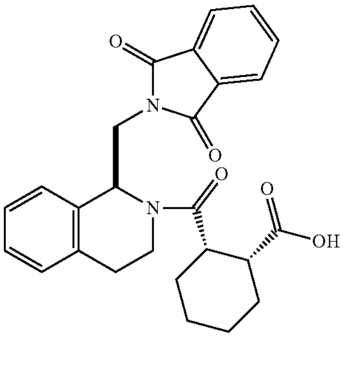 [SMILES: O=C(O)[C@@H]1CCCC[C@@H]1C(=O)N1CCc2ccccc2[C@H]1CN1C(=O)c2ccccc2C1=O] | 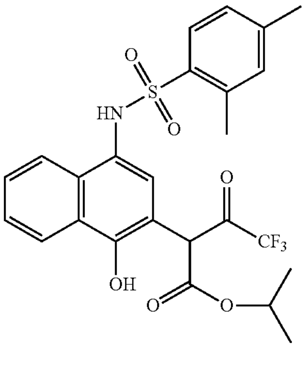 [SMILES: Cc1ccc(S(=O)(=O)Nc2cc(C(C(=O)OC(C)C)C(=O)C(F)(F)F)c(O)c3ccccc23)c(C)c1] |
| $K_d$ (μM) (Keap1 binding affinity) | 1.0 (most active isomer) | 1.7 (racemic mixture) |

TABLE 1-continued

| Comparison of the two leads[a] | | |
|---|---|---|
| | Lead 1 (LH601A) | Lead 2 (LH602) |
| Molecular Weight | 446.50 | 523.52 |
| # of chiral centers | 3 | 1 |
| pKa | | |
| most acidic | 4.7 ± 0.4 | 6.2 ± 0.4 |
| most basic | −1.4 ± 0.4 | −1.7 ± 0.7 |
| Freely rotatable bonds | 4 | 8 |
| H acceptors | 7 | 7 |
| H donors | 1 | 2 |
| H donor/acceptor sum | 8 | 9 |
| cLogP | 1.8 ± 0.5 | 6.9 ± 0.9 |
| logD at pH 7 | −0.66 | 5.8 |
| Predicted aqueous solubility at pH 7 | 2.6 g/L (5.8 mM) | 0.18 mg/L (0.34 μM) |
| PSA (Å$^2$) | 95 | 118 |
| Structure alerts[b] | None | 4-hydroxyaniline |

[a]Red highlights the Lipinski rule of 5 violations.
[b]Structure alerts refer to groups that potentially form reactive metabolites.

As shown in Table 1, the two leads have relatively large molecular weights, which are not unexpected considering that we are targeting protein-protein interactions that often require effective inhibitors to be larger in molecular size. We should be more lenient when applying the empirical rules used in selecting leads and drugs for further optimization and evaluation. Lead 2 also has a large c Log P as well as a 4-hydroxyaniline structure alert for potential reactive metabolite formation. While working on both leads have focused on improving their target binding affinity, ARE-inducing activity, physicochemical, pharmaceutical, and ADME properties, work on lead 2 will also deal with the structure alert of 4-hydroxyaniline Several potential scaffolds containing heterocyclic ring systems are being explored as bioisosteric replacements for LH602 analogs without the 4-amino-1-naphthol to identify more desired alternative scaffolds.

X-Ray Crystal Structural Studies of the Keap1 Kelch Domain Protein with the Small Molecule Inhibitors This section illustrates crystallization and structure characterization of the Keap1 Kelch domain bound to small molecule compounds identified through the high throughput screening.

Cocrystallization and Structure Determination:

The structure of the isolated human Keap1 Kelch domain has previously determined to 1.35 Å resolution and the complex of the human Keap1 Kelch domain bound to the 16mer Nrf2 peptide to 1.5 Å resolution. This protein is highly purified and suitable for cocrystallization efforts. For cocrystal formation, the Keap1 Kelch domain (~10 mg/mL) and various inhibitors are mixed in solution prior to crystallization attempts at varying stoichiometries, typically with five to ten-fold molar excess of an inhibitor, as solubility permits. Protein-inhibitor complexes are screened for crystallization using a sparse matrix screen, such as those in commercially available kits (Hampton Research). Crystallization screens are performed using a Gryphon robot (Art Robbins), which allows 96 conditions to be screened with 70 μL of sample, at three different ratios of protein to well buffer. Hits from crystallization screens are optimized to improve crystal morphology and increase crystal size.

The structure solution proceeds via molecular replacement using the previously determined structure of the human Keap1 Kelch domain. Presence of bound inhibitor is confirmed via difference Fourier maps. Successful crystallization in novel space groups (different from the isolated domain) is also be indicative of successful complex formation, as the crystal lattice of the Keap1 Kelch domain occludes the expected binding site of the inhibitor. The refinement of the structure proceeds using standard methods. The resulting structure(s) is compared and contrasted with the structures of the isolated (uncomplexed) Keap1 Kelch domain and with the Keap1 Kelch domain-Nrf2 peptide complex to assess structural changes and key binding determinants of the inhibitors.

The suitability of inhibitors and various additives is assessed in, e.g., DMSO, β-octyl glucoside, and PEG 400. These compounds are used to solubilize the inhibitors in concentrated stocks that are then diluted (typically 10-fold) by mixing with the protein. The appropriate additive, concentrations of stock solutions and various dilutions are assessed on a case-by-case basis for each inhibitor.

In Vivo Assay

This section illustrates the approach to evaluate selected compounds in vivo for their oral bioavailability, pharmacokinetic profiles, and effects on the expression of ARE-mediated genes and carcinogenesis in TRAMP mouse model of prostate cancer to establish feasibility of using direct inhibitors of Keap1-Nrf2 interaction as antioxidant inflammation modulators. Potent inhibitors are subjected to in vivo studies in mice to investigate their oral bioavailability, preliminary pharmacokinetic profiles, and effects on prostate carcinogenesis and ARE-mediated gene expression. The latter will be performed using qPCR and Western blotting of tissues taken from mice treated with potent inhibitors of Keap1-Nrf2 interaction.

Since the long-term objective of this research is to discover and develop selective and potent inhibitors of Keap1-Nrf2 interaction as antioxidant inflammation modulators to be used as pharmacological probes and potential chemopreventive and therapeutic agents of oxidative stress-related diseases, feasibility of using as such needs to be established by evaluating selected inhibitors in animals for their effects on the expression of ARE-mediated genes and the disease process. We selected the TRAMP mouse model of prostate cancer for this purpose because it is a well-recognized model of prostate carcinogenesis used to follow the progression and multi-stage development of the disease within a short time period of 10-20 weeks. The mouse model has been used to demonstrate the induction of Nrf2-mediated expression of oxidative stress and inflammation markers by the chemopreventive and anti-inflammatory indirect Keap1-Nrf2 inhibitors. Before they are tested in vivo in the TRAMP mouse model, it needs to be established that the test compounds are orally bioavailable, can reach their biologically active concentration, and have sufficiently long half-lives (sufficient exposure) to reach their site of action. Since these are standard parameters required of candidate compounds advanced to in vivo studies, a person skilled in the art would be able to use them to assess the maximum tolerated doses, oral bioavailability, pharmacokinetic profile of test compounds before evaluating their effects on carcinogenesis and relevant gene expression in TRAMP mouse model of prostate cancer. The in vivo studies can be expanded in the future to include other animal models of oxidative stress like unilateral ureteral obstruction model of chronic kidney disease.

Induction of Nrf2-Mediated Phase II Drug Metabolizing and Antioxidant Genes and Prevention of Prostate Carcinogenesis in TRAMP Mouse Model.

TRAMP mouse is an autochthonous transgenic animal model of prostate cancer that recapitulates the whole spectrum of human prostate tumorigenesis from the earliest PIN lesions to androgen-independent disease. It represents an excellent model of prostate carcinogenesis of which the prostate tissue progresses into the different stages of tumors and exhibiting histological and molecular features to human PCa. This transgenic mouse model has been used to investigate the chemopreventive properties of many natural product and synthetic indirect inhibitors of Keap1-Nrf2 interaction. The effects of the direct inhibitors of Keap1-Nrf2 interaction are being tested on both the carcinogenesis process and the expression of Nrf2-mediated antioxidant gene expression. We will use the same design and approaches to investigate the effects of our compounds on prostate carcinogenesis and to measure the changes elicited by our compounds in the mRNA and protein expression levels of Nrf2-mediated genes including Nrf2, GSTm2, NQO1, UGT1A1, HO-1, SOD1 in tissues and organs taken from drug-treated TRAMP mice.

Thus, this invention represents an interdisciplinary approach towards discovery of potential drug candidates for a variety of oxidative stress-related diseases. It involves hit discovery through HTS, hit to lead, lead optimization, and (preclinical) pharmacological evaluation. The structures of human Keap1 Kelch domain and its complex with the 16-mer Nrf2 peptide have been solved through crystallization, and cocrystallization conditions for Keap1 Kelch domain. The two small molecule leads are under investigation and are used for cocrystal structure analysis and characterization of the human Keap1 Kelch domain complex with the small molecule inhibitors.

The human hepatoma HepG2 cells stably transfected with the pARE-TI-luciferase construct (HepG2-ARE-C8) have been used to evaluate the activity of many naturally occurring chemopreventive chemicals in inducing ARE genes, and the TRAMP mouse model of prostate cancer has been used to test the chemopreventive properties of natural product indirect inhibitors of Keap1-Nrf2 interaction.

Thus, it would be feasible to a person skilled in the art to use the potent small molecule direct inhibitors developed in this invention to demonstrate that direct inhibition of Keap1-Nrf2 interaction could induce the expression of ARE-controlled oxidative stress-related cytoprotective genes, similarly to many of the natural and synthetic indirect inhibitors of Keap1-Nrf2 interactions, but without the cytotoxicity concerns.

Assay of Activities and Determination of Structure-Activity Relationship

This section illustrates the approach to determine the activity of synthesized analogs in a series of biochemical assays and cell-based assays to obtain structure-activity relationship and to elucidate the role of Keap1-Nrf2-ARE pathway in oxidative stress and inflammation.

The approach includes studying mechanism of action of the lead compounds and their analogs by measuring their biological activity as direct inhibitors of Keap1-Nrf2 interaction in a series of direct binding and cell-based assays, including fluorescence-based binding assays, SPR-based solution competition assay, and ARE-luciferase reporter assay; determining the specificity of the direct inhibitors of Keap1-Nrf2 interaction by measuring the lack of inhibition of the ubiquitous NF-κB signaling pathway, including NF-κB-luciferase reporter assay and inhibition of nitric oxide production in LPS-stimulated RAW 264.7 cells; and directing the lead optimization efforts through structure-activity relationship analysis to obtain compounds with enhanced binding affinity, improved physicochemical and pharmaceutical properties, and decreased development liabilities.

A series of biochemical and cell-based assays are used to confirm that the compounds synthesized are direct specific inhibitors of Keap1-Nrf2 protein-protein interaction. In addition, several routine ADME/Tox assays are used to evaluate the inhibitors for their potential ADME/Tox liabilities. Major assays include:

Fluorescence-Based Direct Binding Assays.

Two fluorescence-based binding assays have been developed for the discovery of direct inhibitors of Keap1-Nrf2 interaction. The first of these assays is an FP assay that uses a fluorescently labeled Nrf2 peptide amide as the probe and directly measures the displacement of fluorescent probe from the Nrf2-binding site of Keap1 Kelch domain by inhibitors via changes in fluorescence anisotropy. This was the assay used to screen the MLPCN library and discover the two potent hits used as leads in this project and dose-response curves of the two hits are shown in FIG. 3B. The second of the fluorescence-based assays is a time-resolved fluorescence energy transfer (TR-FRET) assay which uses an in situ labeling method we recently developed to attach a lanthanide chelate to Keap1 Kelch domain as the FRET donor and fluorescein-labeled Nrf2 peptide as the acceptor. One advantage of the TR-FRET assay is that it is less susceptible to compound interference than an FP assay.

Surface Plasmon Resonance (SPR)-Based Direct Binding Assay.

We have developed a SPR-based solution competition assay to measure the solution binding affinity of inhibitors of Keap1-Nrf2 interaction. We use a SA chip immobilized with a long 16mer Nrf2 peptide on the chip surface to measure the solution binding constants between Keap1 Kelch domain and any inhibitor through a solution competition assay. As shown in FIGS. 3C/3D/3E, we have been able to measure the solution binding affinity of the two leads and the stereoisomers of LH601A.

ARE Gene Reporter Assays in HepG2 Cells.

Compounds synthesized were evaluated for their ability to induce ARE gene expression in HepG2 cells. We have been using the ARE-luciferase or ARE β-lactamase reporter assay to study the effect of isothiocyanates and the compounds already synthesized on the expression of ARE genes. The HepG2-C8 cells used in this assay were selected after stable transfection of HepG2 cells with pARE-TI-luciferase construct using a FuGENE™ 6 method and the CellSensor® ARE-bla HepG2 cell line is commercially available from Invitrogen.

PathHunter® U2OS Keap1-Nrf2 Functional Assay.

We recently obtained the PathHunter® nuclear translocation assay kit from DiscoveRx and this assay is been used to demonstrate nuclear translocation of Nrf2 upon inhibition of Keap1-Nrf2 interaction by our direct inhibitors. The PathHunter® assay uses Enzyme Fragment Complementation (EFC) technology with U2OS cells expressing two complementing fragments of β-Gal in different cellular compartments and quantitate using chemiluminescence the activity of β-Gal, which corresponds to the amount of Nrf2 translocating into the nucleus upon disruption of Keap1-Nrf2 interaction.

Induction of Nrf2-Mediated Phase II Drug Metabolizing and Antioxidant Genes In Vitro.

Quantitative real-time polymerase chain reaction (qPCR) is used to measure the mRNA expression levels of Nrf2-mediated genes including endogenous Nrf2, GSTm2, UGT1A1, NQO1, HO-1, and SOD1 while Western blotting is used to investigate the protein expressions of these biomarkers; these are routinely performed on cells and tissues from culture and animals. After treatment of the HepG2, RAW 264.7, and SW-480 cells with our compounds for a given amount of time (e.g, 6 h), the total RNA is reverse-transcribed to cDNA by TaqMan Reverse Transcription Reagents. SYBR Green fluorescence is used to measure the product of qPCR. Glyceraldehyde 3-phosphate dehydrogenase (GAPDH) is used as the housekeeping gene, and the Applied Biosystems 7900HT Fast Real-Time PCR System is used to detect quantitatively the induction of mRNA of Nrf2, GSTm2, NQO1, UGT1A1, HO-1, SOD1 as we reported previously. For Western blotting to determine protein expression, cells is treated similarly with test compounds but for a longer duration (e.g., 24 h) before they are collected, lysed, and analyzed for protein expression. The proteins are separated by SDS-PAGE and transferred onto nitrocellulose membranes. Membranes are probed using the different mono- or polyclonal antibodies (targeting the various proteins) and the respective secondary antibodies. The bands are visualized and quantified by BioRad ChemiDoc XRS System as done previously.

Inhibition of the Ubiquitous NF-κB Signaling Pathway and Nitric Oxide Production or Lack Thereof as Indications of Selectivity.

Indirect inhibitors of Keap1-Nrf2 interaction such as curcumin and isothiocyanates have been shown to have inhibitory effect on the activity of NF-κB in cells induced by cytokines like TNFα and the nitric oxide production in RAW 264.7 cells stimulated by LPS through attenuation of the ubiquitous NF-κB signaling pathway. Since we are developing direct and specific inhibitors of Keap1-Nrf2 interaction, they are not expected to interfere with the NF-κB signaling pathway, thus would unlikely have any effect on NF-κB activity and nitric oxide production in cells. Therefore, lack of inhibitory activity on the NF-κB-luciferase reporter activity in HCT116 cells in the presence of TNFα and on nitric oxide production in LPS-stimulated RAW 264.7 cells can be used as indications of target selectivity. We will perform the in vitro NF-κB activity assay in NF-κB-luciferase-expressing HCT116 cells (recently established using a literature protocol) and in LPS-stimulated RAW 264.7 cells (a well established assay) on novel compounds found to have superior ARE-inducing activities using curcumin and isothiocyanates as the controls.

Membrane Permeability.

In addition to optimize their intrinsic activity and metabolic stability, the compounds synthesized also need to possess good membrane permeability in order to reach their site of action within cells. We will determine the membrane permeability of all our compounds synthesized using the established parallel artificial membrane permeability assay (PAMPA) following the published protocol from pION. This assay is carried out in pH 7.4 buffer containing 0.1% DMSO, reflecting the conditions of the cell-based assays. All liquid-handling steps for the PAMPA assay are performed on our MultiProbe II HT liquid handling robot. The concentration of the compounds in the donor and acceptor buffers (100 μL aliquot) is determined by UV to calculate the permeability coefficient (Pe). We will use verapamil, carbamazepine, and ranitidine as the high, medium, and low permeability standards, respectively.

Other tests also include measuring the compounds' aqueous solubility (preferably >100 μg/mL) and metabolic stability in the presence of human liver microsomes. Properties like hERG binding liability, CYP inhibition and induction are evaluated through preclinical profiling companies like Cerep and BioFocus. The cell-based ARE- and NF-κB-luciferase reporter assays and nitric oxide production assay are preceded by antiproliferative assays to assess their cytotoxicities in these cell lines. In addition, novel compounds have been submitted to NCI Developmental Therapeutics Program for screening in NCI 60 cell lines.

Synthetic Methods

Synthesis of Analogs of Lead Compounds

To synthesize various analogs of lead compounds designed to explore the chemical space in various parts of the lead structures for improved inhibitory activity of Keap1-Nrf2 interaction and pharmaceutical properties, selection of analogs to be synthesized is facilitated by computer-assisted drug design approaches based on the cocrystal structures obtained of Keap1 Kelch domain with a small molecule inhibitor bound and guided by their activity in biochemical assays and cell-based in vitro assays.

This approach is to optimize the chemical structure of two lead compounds and to obtain potent Keap1-Nrf2 inhibitors with mid-to-low nanomolar binding affinity to Keap1 Kelch domain and good physicochemical and pharmaceutical properties including solubility, membrane permeability and without obvious developmental issues.

Molecular Dissection of Leads.

Figure 8:
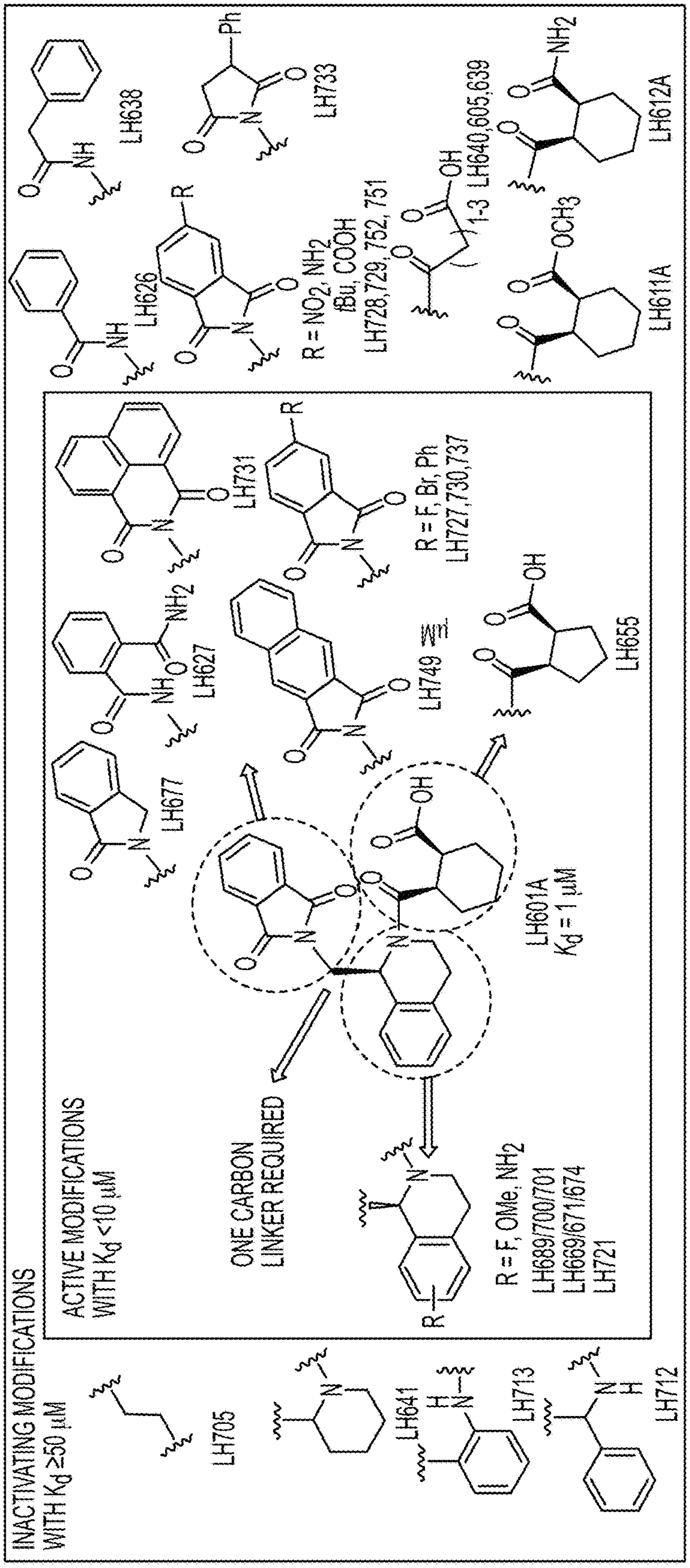
FIG. 8 illustrates a preliminary SAR of LH601. Some structure modifications made on the three highlighted regions and a linker. Active modifications inside the blue rectangular box refer to those structural changes that retain most, if not enhance, binding affinity ($K_d$<10 μM) while inactivating modifications outside the blue rectangular box result in dramatic loss of binding affinity ($K_d$>50 μM).

In addition to synthesis of the two hits for activity confirmation, stereochemistry assignment, and measurement of physicochemical and ADME properties, we have identified the importance of the carboxylic acid functional group in LH601A. We made and tested the corresponding amide and methyl ester of LH601A synthesized from the pure enantiomer prepared via chiral HPLC separation. The methyl ester (LH611) was completely inactive and the amide (LH612) was about 20-fold less active than LH601A (Note:

5% DMSO was used to ensure complete solubility during assay), suggesting that the free carboxylic acid group in LH601A is required for binding to Keap1 Kelch domain. We have also attempted to reduce the leads' molecular size and to improve their other lead-like properties. Example of such molecular dissection include the removal of the benzene ring or ethylene in THIQ (tetrahydroisoquinoline) as in LH641 or LH712; both resulted in complete loss of binding. From the LH601 analogs synthesized (some of which are shown in FIG. 8), we summarize the preliminary SAR as the following: 1) The importance of stereochemistry for activity. LH601A has SRS; many of THIQ analogs have similar requirement (activity resides in one diastereomer); 2) substitutions are tolerated on THIQ especially F, OMe and $NH_2$; 3) Substitutions tolerated on phthalimido group but no COOH or $NO_2$, $NH_2$ or tBu; 4) One carbon linker preferred between THIQ and phthalimido group; and 5) Acidic functionality preferred on cycloalkane ring. Efforts are being made to systemically explore the chemical spaces around the various points of the scaffold to improve binding affinity, membrane permeability, and other physicochemical and pharmaceutical properties. The process of molecular dissection and lead optimization are facilitated by computer-assisted drug design approaches based on the cocyrstal structures of Keap1 Kelch domain with an Nrf2 peptide and small molecule leads as briefly discussed below.

Figure 5:
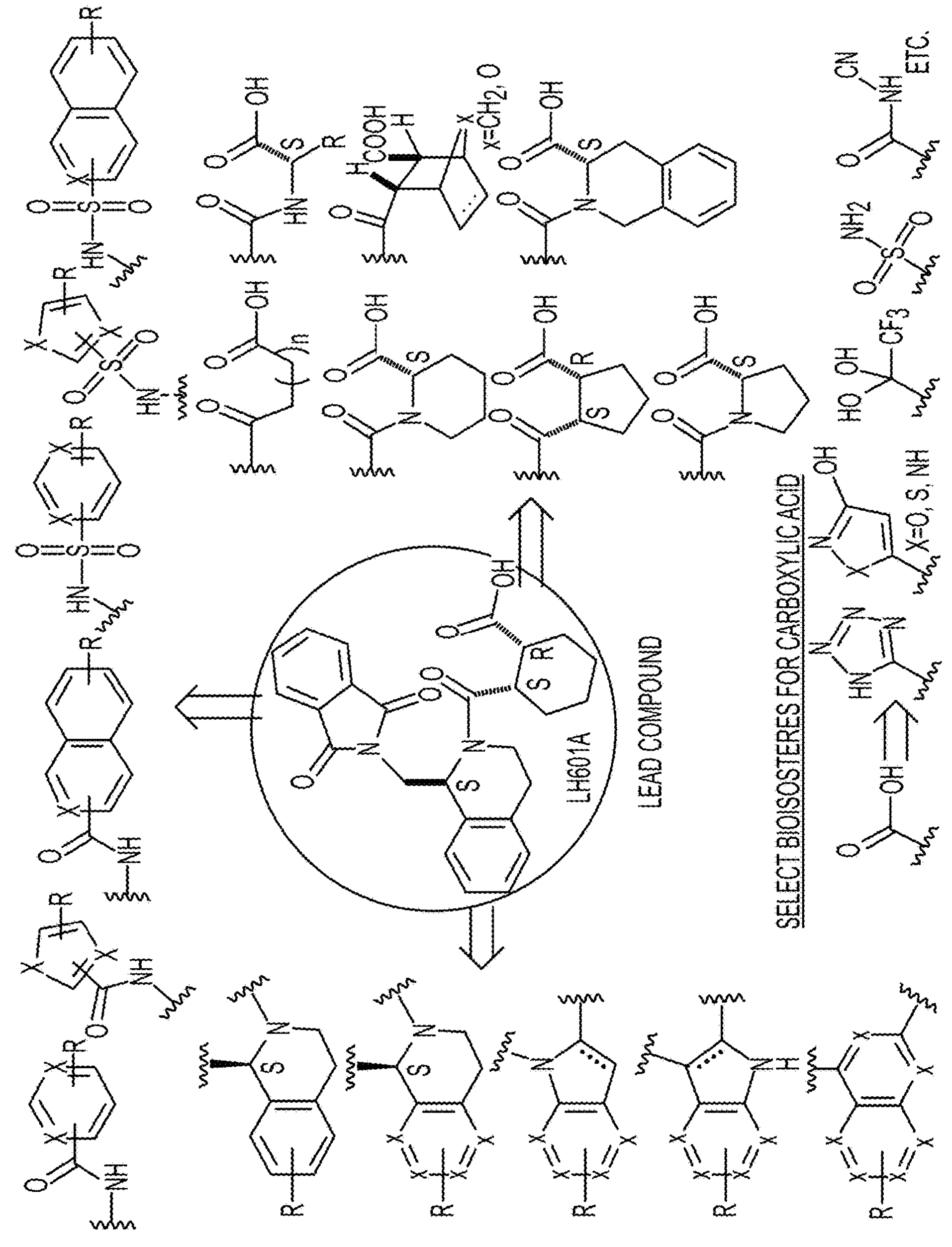
FIG. 5 illustrates representative replacements that could be made for each of the three parts in LH601A during the lead optimization phase for inhibitors of Keap1-Nrf2 interaction with improved potency, better cellular permeability, and good pharmaceutical properties.

We have docked both LH601A and LH602 to the Nrf2 peptide binding site in the Keap1 Kech domain as existed in the complex of Keap1 Kelch domain with Nrf2 peptide (PDB code: 2FLU); both LH601A and LH602 were shown to have similar binding poses to the binding site. Thus, similar lead optimization approaches could be used for LH601A and LH602. The lead molecules are divided into three parts for structure optimization. To illustrate the various chemical spaces we have explored during the lead optimization step, various replacement groups that can be used for each of the three parts are illustrated in FIGS. 4 and 5. The analogs are synthesized according to the order of their binding to Keap1 Kelch domain as ranked by the GOLD protein-ligand docking program. Although docking is being done starting from the structure of Keap1 Kelch domain as complexed to Nrf2 peptide, it will give us more confidence when we use the cocrystal structure of Keap1 Kelch domain in complex with our small molecule leads (obtained in Example 2).

Optimization of Lead LH601A

Based on the comparison of structure features and properties of the two leads in Table 1, we first chose LH601A as a lead for optimization. Based on our docking studies, the carboxylate of LH601A is directly interacting with the Arg415 residue in the Nrf2 peptide binding site of Keap1 Kelch domain Thus, most replacements selected for cis-2-carbonyl cyclohexane-1-carboxylic acid contain a carboxylate as shown in FIG. 5. The carboxylate can also be replaced with carboxylate bioisosteres such as tetrazole, 3-hydroxyisoxazole, hydrated trifluoromethyl ketone, sulfonamide, and hydroxamic acid. In addition, the aryl group can also be varied between 5 and 6-membered rings and fused ring systems, and the saturated ring in tetrahydroisoquinoline can be replaced with other 5- or 6-membered rings shown in FIG. 5.

Optimization of Lead LH602

Figure 6:
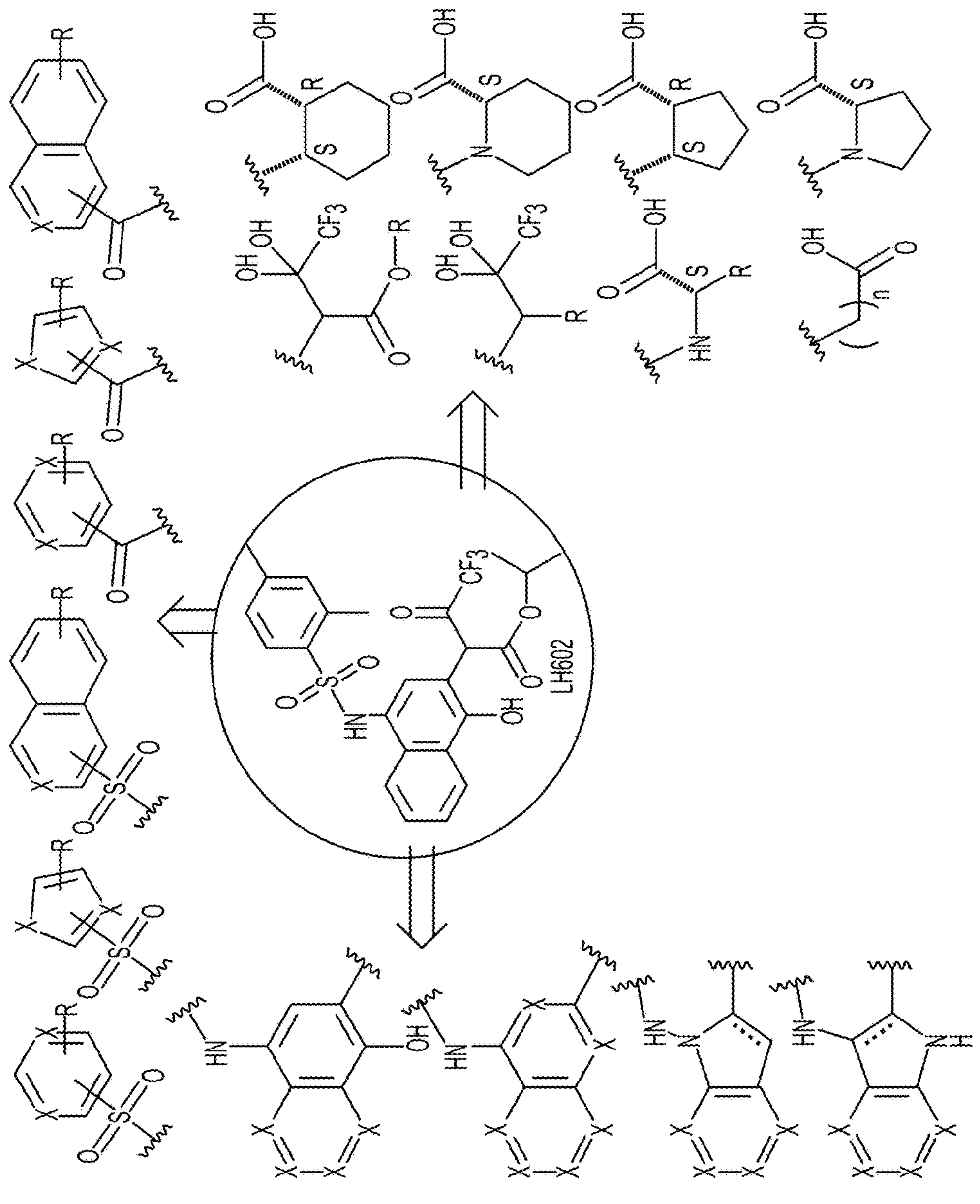
FIG. 6 illustrates representative replacements that could be made for each of the three parts in Hit 2 (LH602) during the lead optimization phase for inhibitors of Keap1-Nrf2 interaction with improved potency, better cellular permeability, and good pharmaceutical properties.
Figure 7A:
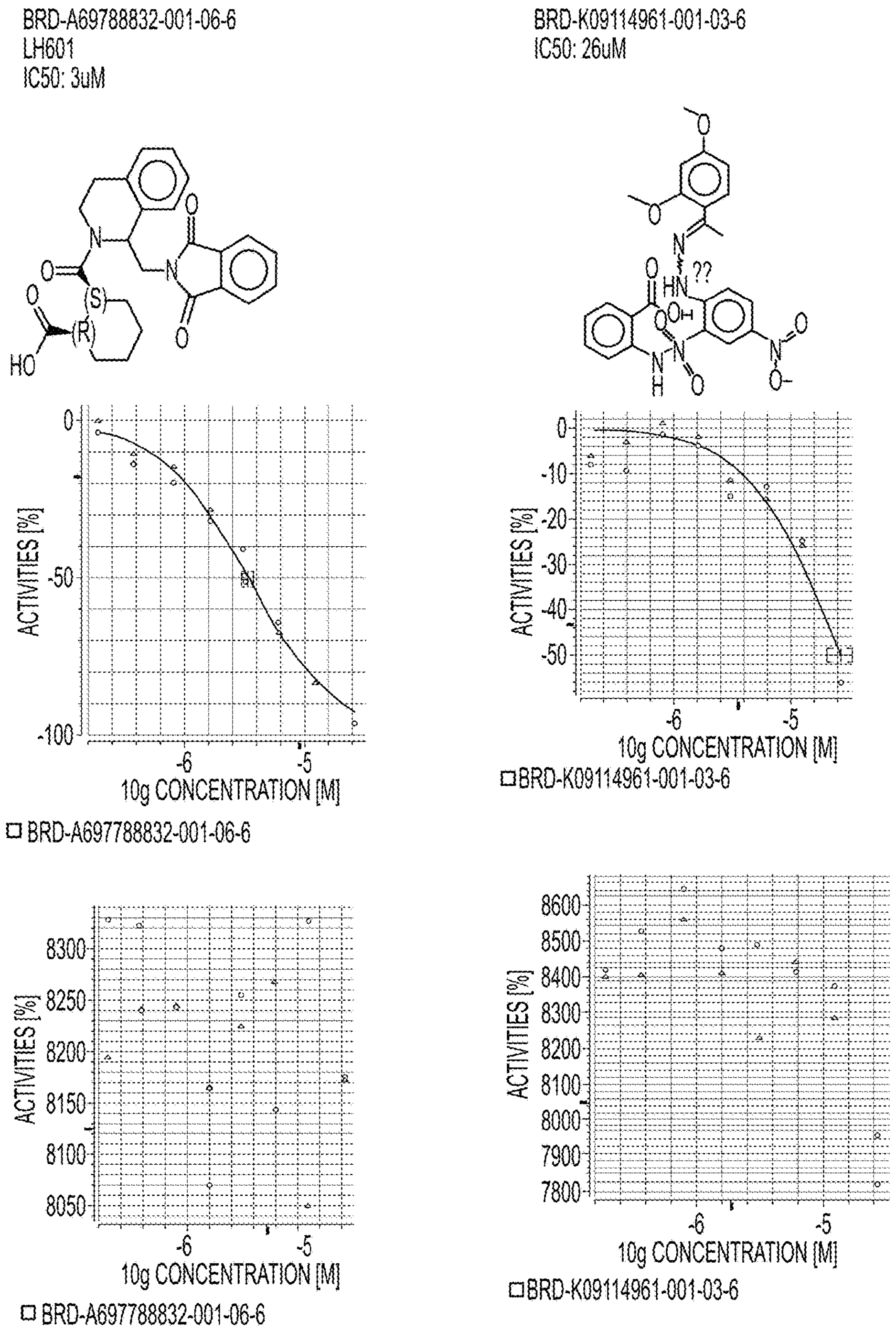
FIGS. 7A, 7B, 7C and 7D illustrate a hit list in Keap1-retest in dose.
Figure 7B:
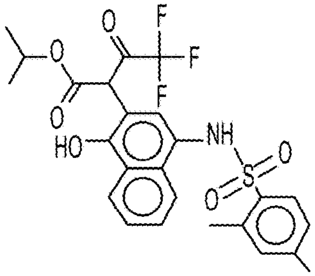
Figure 7B:
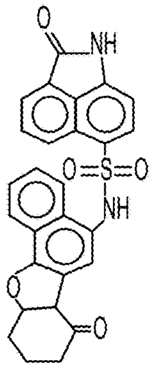
Figure 7B:
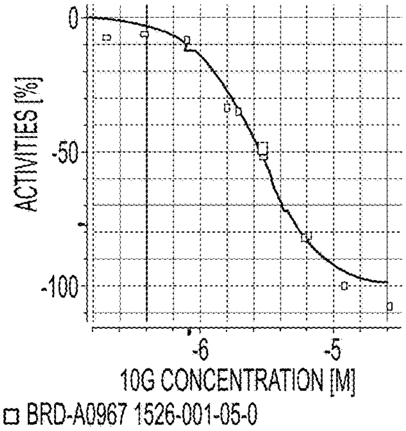
Figure 7B:
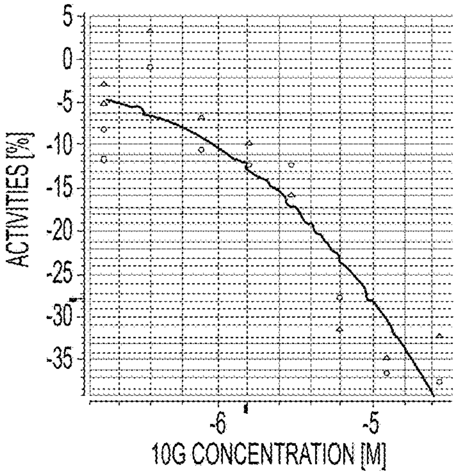
Figure 7B:
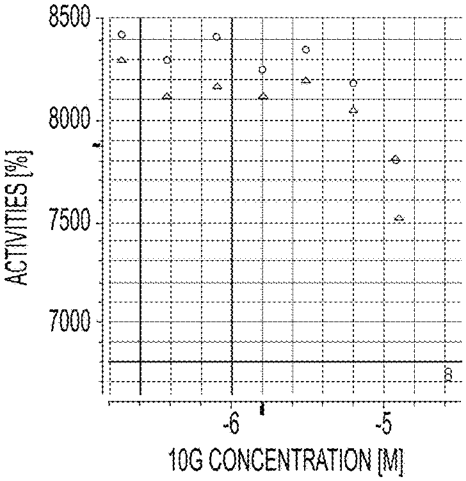
Figure 7B:
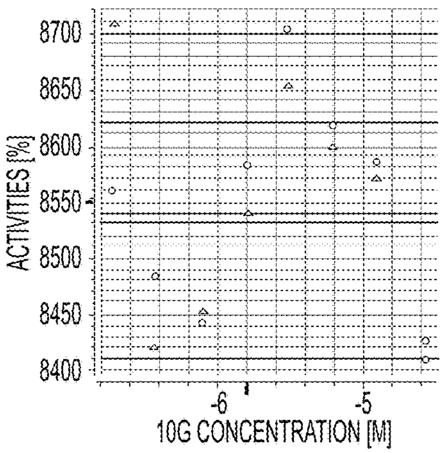
Figure 7C:
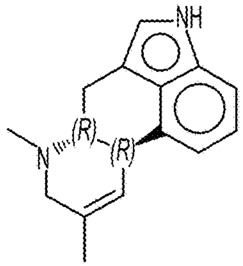
Figure 7C:
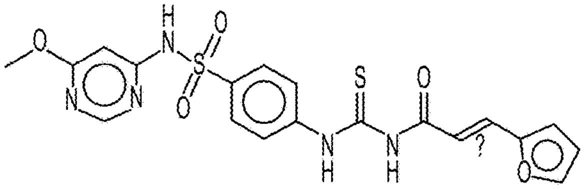
Figure 7C:
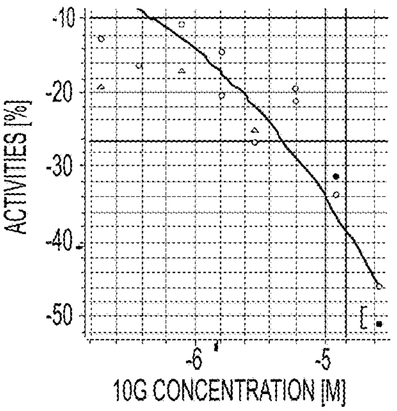
Figure 7C:
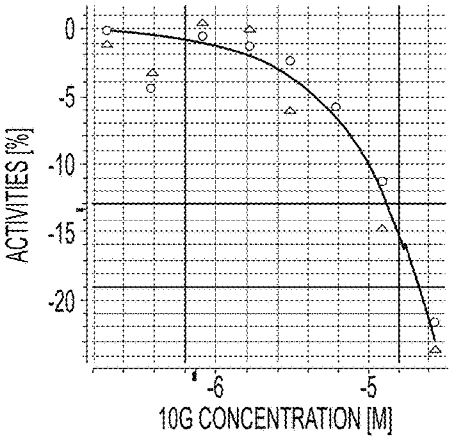
Figure 7C:
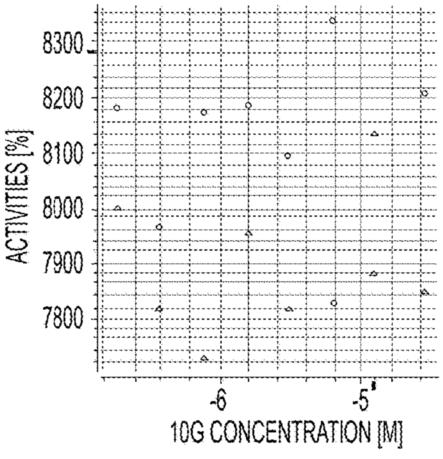
Figure 7C:
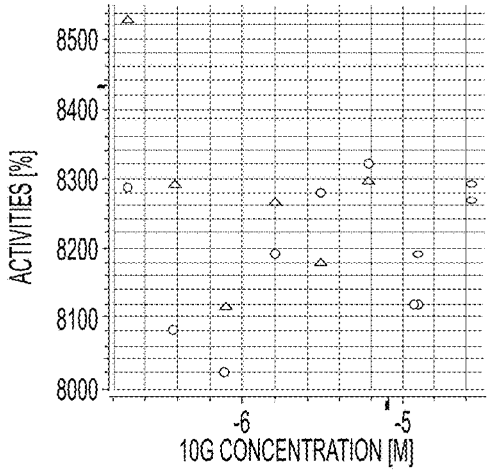
Figure 7D:
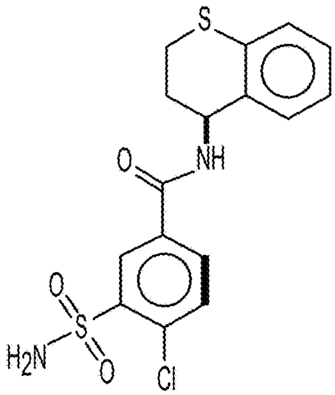
Figure 7D:
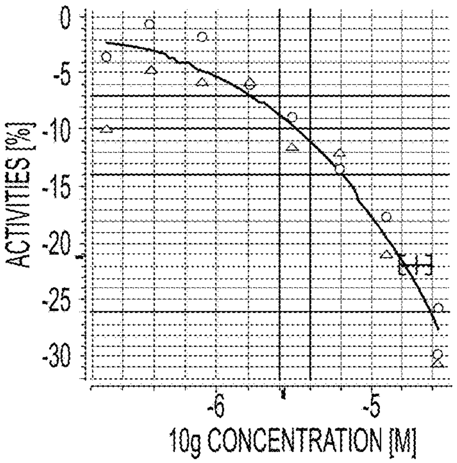
Figure 7D:
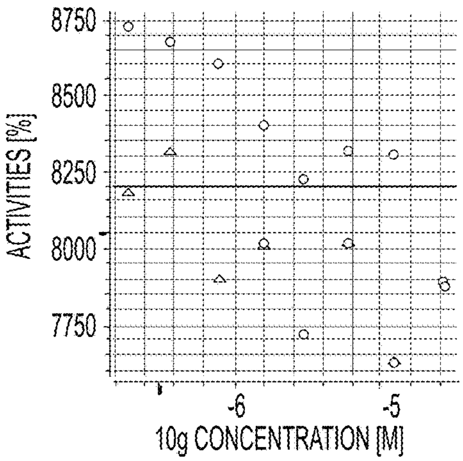
Figure 7D:
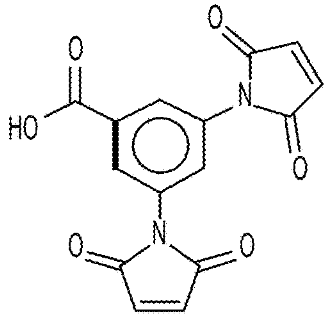
Figure 7D:
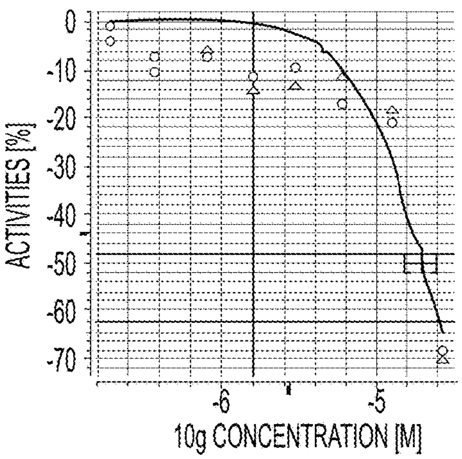
Figure 7D:
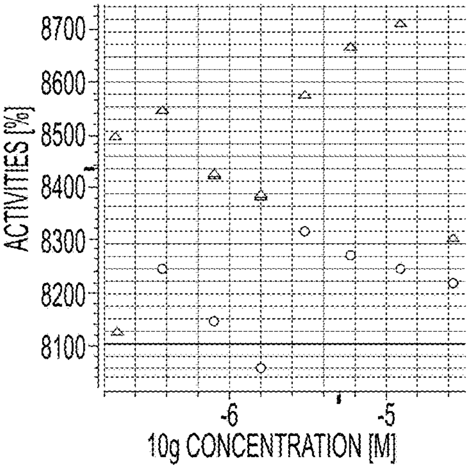

As shown in FIG. 6, similar approaches/replacements are used for LH602, which provides a second scaffold—the bicyclic naphthalene. LH602 was resynthesized and has been confirmed to have an $IC_{50}$ of 3 μM and a Kd of 1.7 μM to Keap1 Kelch domain. For many of the replacements outlined, similar reactions to those shown in Schemes 1-3 can be used. New routes are also explored to obtain compounds with unique replacements.

Figure 3E:
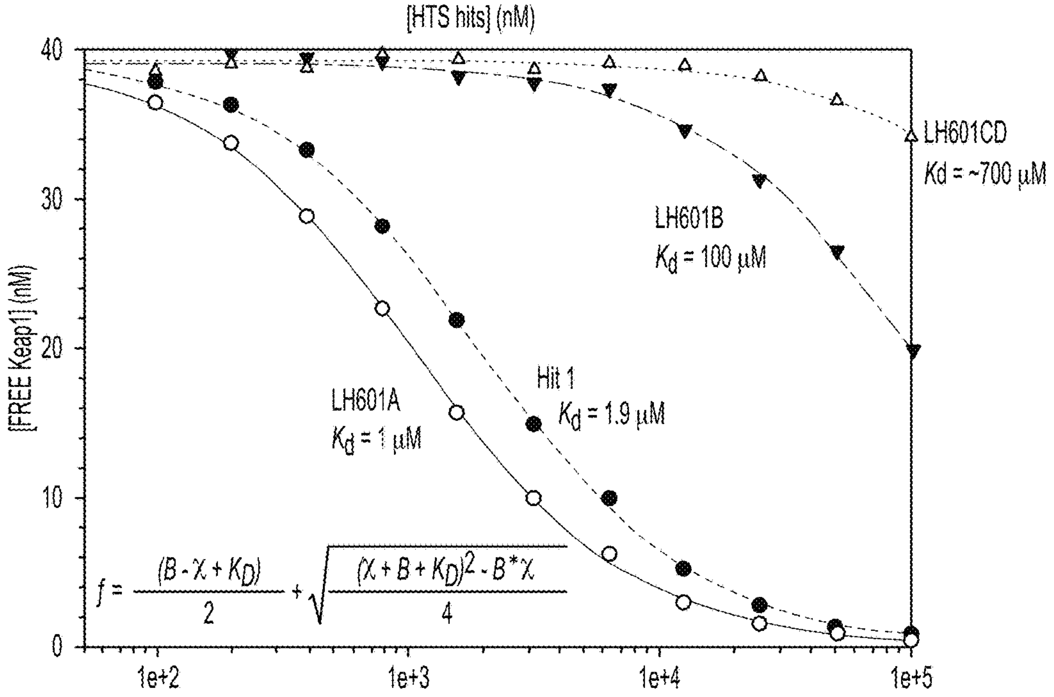
FIG. 3E illustrates comparison of $K_d$ of different stereoisomers of LH601.
Figure 3F:
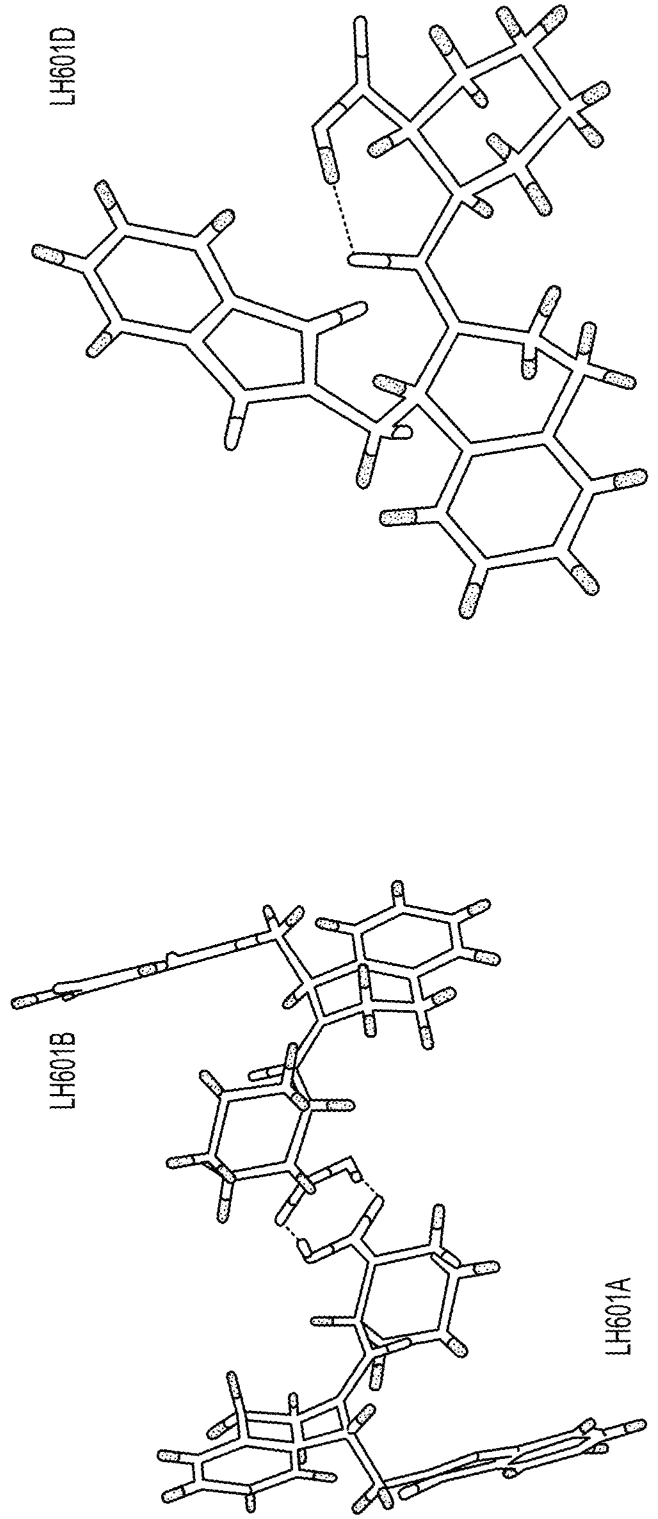
FIG. 3F illustrates X-ray crystal structures of LH601A/B as a pair and LH601D as a single enantiomer.

Resynthesis of Hit Compounds and Analogs for Activity Confirmation and Lead Identification As shown in FIG. 3A, there are three chiral centers in Hit 1. When we synthesized Hit 1 according to Scheme 1 by reacting 1-phthalimidomethyl tetrahydroisoquinoline ((±)-4) with cis-cyclohexanedicarboxylic anhydride, we obtained an expected mixture of four stereoisomers (5, LH601) based on our chiral HPLC analyses on a Chiralcel OD-R column while the Hit 1 sample from the NIH MLPCN library contains ~90% of one major diastereomer (probably due to repeated recrystallization in the commercial process). LH601 mixture was shown to be two fold less active than the Hit 1 sample obtained from the NIH MLPCN library. We then separated LH601 into diastereomers (LH601A/B and LH601C/D) using flash silica gel chromatography. LH601A/B was shown to contain the active isomer in Hit 1 and was further separated into the two enantiomers LH601A and LH601B by preparative normal phase chiral separation on a Chrialcel OD column. The activities of LH601A, LH601B and LH601C/D were then compared to that of Hit 1 in our FP and SPR assay. As shown in the SPR dose-response curves in FIG. 3E, we have identified the most active stereoisomer in Hit 1 being LH601A with a Kd of 1 μM while its enantiomer LH601B has a Kd of only 100 μM and the other diastereomer LH601CD is inactive. For the assignment of stereochemistry, we initially used vibrational circular dichroism (VCD), using the same preparative chiral HPLC to prepare sufficient amount of each of the four stereoisomers for stereochemistry assignment by VCD. We obtained the VCD spectra of all four stereoisomers (A-D) of LH601. Calculations of VCD spectra based on the DFT theory of low energy conformations using Gaussian 09 and comparison of the experimental and calculated VCD spectra using the novel SimIR/VCD computational method suggest that the active stereoisomer LH601A is most likely of SSR configuration (Scheme 1). The stereoselective synthesis and X-ray crystallography were used to unequivocally assign the stereochemistry of the LH601A as SRS, as shown in FIG. 3F. Interestingly, LH601A could only be crystallized as a pair with its enantiomer LH601B even in the presence of 90% e.e. of LH601A, while LH601D readily crystallized as single crystals of the pure LH601D, which was used to assign the absolute stereochemistry of all four LH601 isomers. In addition, the stereochemistry assignment was confirmed by stereoselective synthesis of LH601A as depicted in Scheme 3. The different binding activities among the stereoisomers of LH601 as shown in FIG. 3E demonstrate the structurally specific ligand-target interaction between LH601A and Keap1. The strong binding affinity of LH601A over its stereoisomers provides further evidence of its true direct binding to Keap1 and supports its use as a lead for structure optimization.

Scheme 1. Synthesis and resolution of Hit 1 isomers.

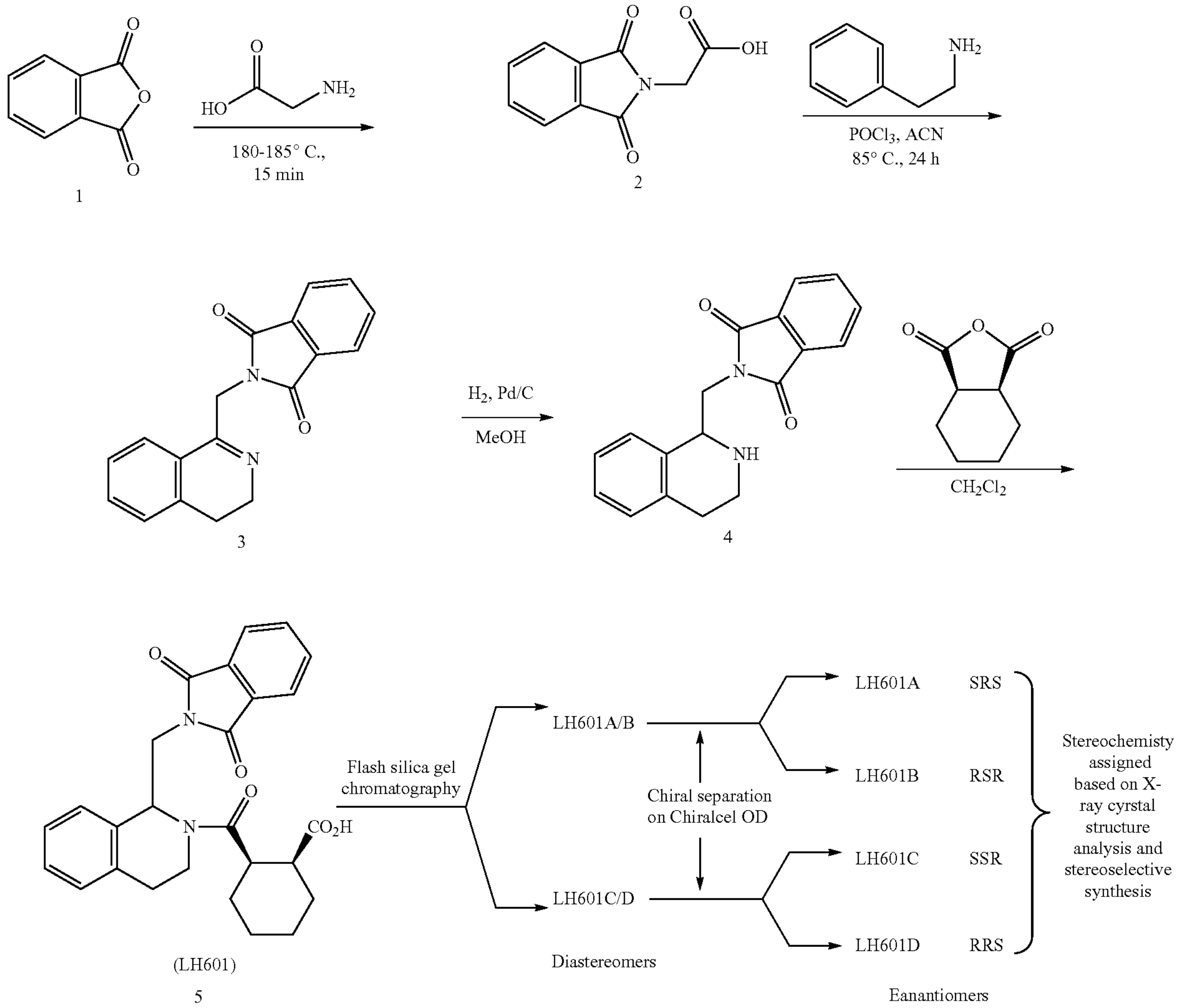

Stereoselective Synthesis of Lead LH601A.

Synthesis of a mixture of four stereoisomers, and resolution by chromatography into pure isomers are shown in Scheme 1, which shows that LH601A has the most potent inhibitory activity against the target Keap1-Nrf2 interaction (FIG. 3E). As shown in Scheme 2, the Noyori asymmetric transfer hydrogenation and an alkaloid-mediated desymmetrization procedure of meso-anhydrides were used to control the chiral centers during the steroselective synthesis. Using the chiral Noyori (S,S)-Ruthenium complex as catalyst of transfer hydrogenation, the imine intermediate 3 was converted to the (S)-teterhydroisoquinoline 4 (see, e.g., Roszkowski, P., et al., *Tetrahedron: Asymmetry,* 2006, 17, 1415-1419). The (S)-4 has alternatively been resolved from the (R)-4 using (—)-dibenzoyl L-tartaric acid ((−)DBTA). The meso anhydride cis-cyclohexane-dicarboxylic anhydride was converted to (1S,2R)-2-(benzyloxycarbonyl)cyclohexane carboxylic acid ((R,S)-10) with benzyl alcohol in the presence of quinine. Simple amide bond coupling between the optically active (S)-4 and ((R,S)-10 produced the benzyl protected (SRS)-11, which upon hydrogenolysis gave the desired enantiomer (SRS)-5 (LH601A).

Scheme 2. Stereo-selective synthesis of LH601A with the SRS configuration.

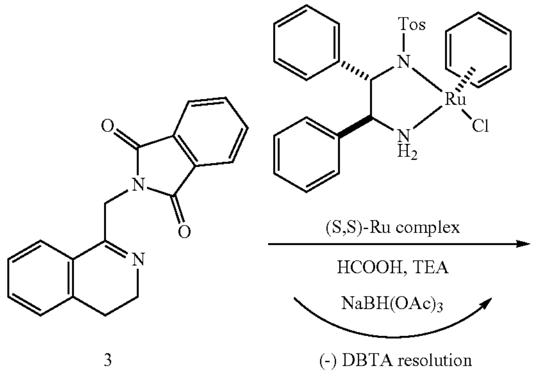

-continued

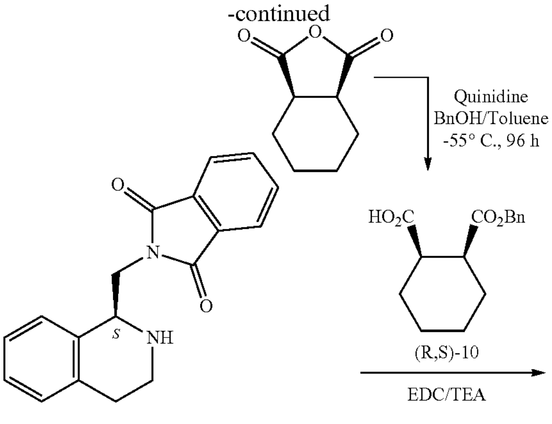

(S)-4

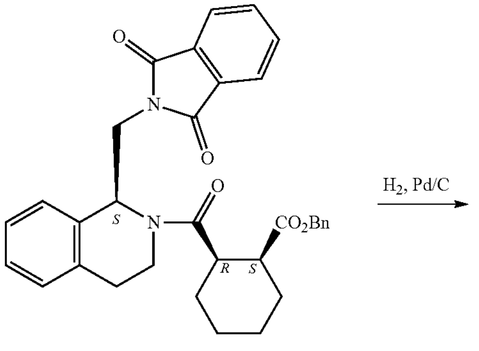

(SRS)-11

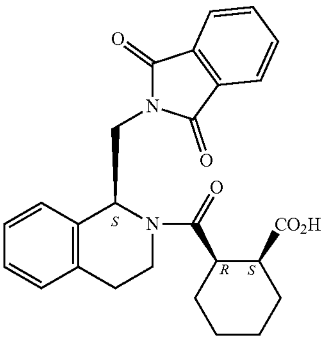

(SRS)-5 (LH601A)

Synthesis of Lead Hit 2 and Analogs

Hit 2 provides a second chemotype with a different scaffold for our lead optimization efforts, especially if we can eliminate or replace 4-hydroxyaniline moiety—the source of concern for reactive metabolite formation. One advantage of Hit 2 is its simpler stereochemistry with only one chiral center. Because of the two adjacent carbonyl groups, the only chiral center could not be easily controlled unless at least one of the carbonyl groups is bioisosterically replaced. We accomplished the resynthesis of Hit 2 (ID LH602) using the series of reactions outlined in Scheme 3. In addition, we have already synthesized two analogs based on the 4-amino-1-naphthol scaffold, which exhibited interesting preliminary SAR, e.g., decreased binding affinity without the two methyl groups on the phenyl ring.

Scheme 3. Synthetic route used in the synthesis of Hit 2 (LH602).

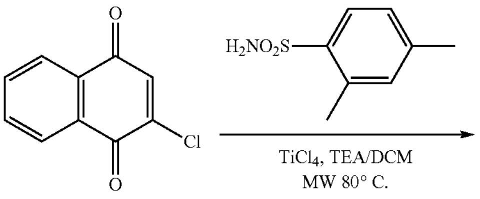

6

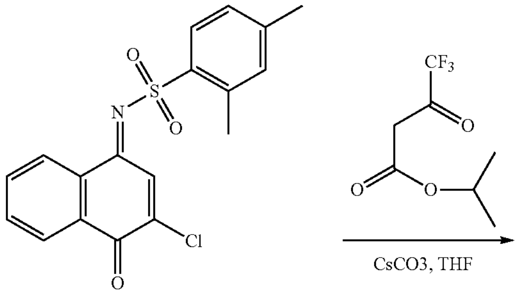

7

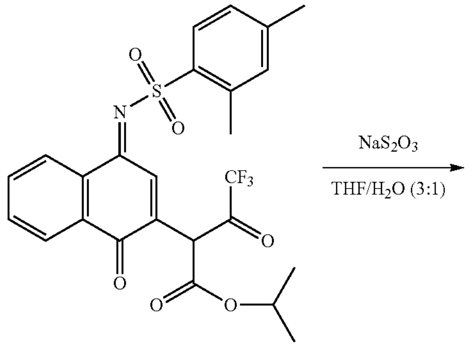

8

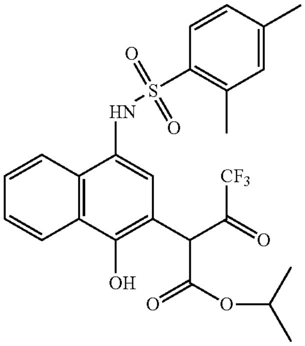

(LH602)

9

EXAMPLES

Synthesis of Analogs Containing Replacements for cis-2-carbonyl cyclohexane-1-carboxylic Acid Scheme 4

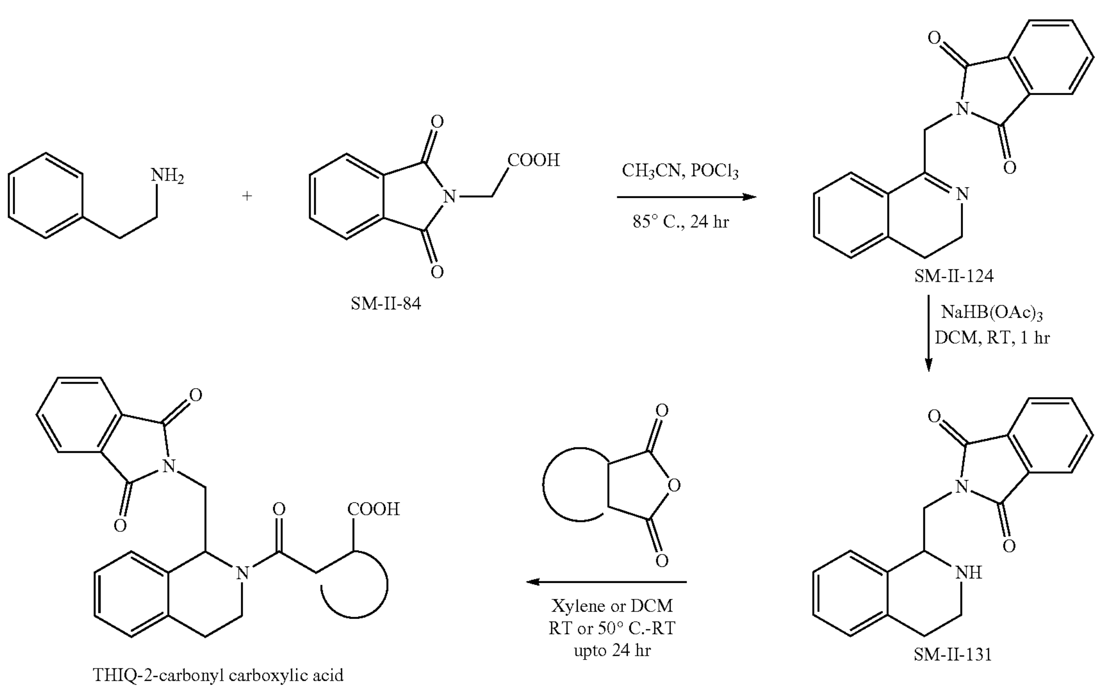

Synthesis of 3,4-Dihydro-1-phthalimidomethylisoquinoline (SM-II-124): N-Phthaloyl Glycine (4 g, 19.5 mmol) and Phenethylamine (2.65 mL, 21.5 mmol) were taken together and $CH_3CN$ (100 mL) was added. $POCl_3$ (7.25 mL, 78 mmol) was added drop wise and the resulting solution was heated at 85° C. for 24 hrs, then cooled to RT and concentrated under reduced pressure. The obtained dark residue was diluted with DCM (100 mL) and washed with aq. NaHCO3 (100 mL) and water (100 mL), then followed by brine (100 mL). The organic layer was concentrated and the crude was precipitated with ethyl acetate (Q.S), washed with ethyl acetate and dried to get 5.2 g of light yellow solid (73%). $^1H$ NMR (DMSO-d6, 400 MHz): δ 7.90 (m, 4H), 7.78 (d, 1H), 7.48 (td, 1H), 7.41 (dd, 1H), 7.32 (d, 1H), 4.90 (t, 2H), 3.47 (t, 2H), 2.62 (t, 2H). MS (ESI+) m/z 291.3 (M+H).

Synthesis of 1-phthalimidomethyl-1,2,3,4-tetrahydroisoquinoline (SM-II-131): 3,4-Dihydro-1-phthalimidomethylisoquinoline (580 mg, 2 mmol) was dissolved in DCM (10 mL) and AcOH (120 μL) was added to solution and then $NaBH(OAc)_3$ (636 mg, 3 mmol) was added in portions. The obtained suspension was stirred at RT for 1 hr and reaction mixture was diluted with DCM (50 mL) and washed with water (2×25 mL) and brine (25 mL). The organic layer was concentrated and the crude was purified via column chromatography (ISCO) using Acetone (0 to 40%) in Hexane as eluent and fractions were concentrated to give 420 mg of light colored product (72%). $^1H$ NMR ($CDCl_3$, 400 MHz): δ 7.81 (m, 4H), 7.22 (m, 4H), 4.36 (dd, 1H), 4.08 (td, 1H), 3.89 (dd, 1H), 3.27 (m, 1H), 2.96 (m, 1H), 2.77 (m, 2H), 1.72 (s, 1H). MS (ESI+) m/z 293.2 (M+H).

General procedure for the synthesis of 1-Phthalimidomethyl THIQ-2-carbonyl carboxylic acids: 1-phthalimidomethyl-1,2,3,4-tetrahydroisoquinoline (0.1-0.3 mmol) was dissolved in 1-3 mL of solvent (DCM or Xylene in case of alicyclic anhydrides) and anhydride (1.1 eq) was added slowly and stirred at RT (50° C. in case of Xylene) up to 3-24 hrs. The obtained precipitate was filtered and washed with diethyl ether and dried. Impure final products were purified via column chromatography (ISCO) using Ethyl acetate (0 to 100% with 1% AcOH) in Hexane as eluent. Some diastereomeric pairs were separated during column chromatography (ISCO) using Ethyl acetate (0 to 100% with 1% AcOH) in Hexane or using $CH_3CN$ (0 to 20% with 1% AcOH) in DCM. A few of enantiomeric pairs were separated by using chiral HPLC using Isopropanol/Hexane mixture.

Example 1

LH603

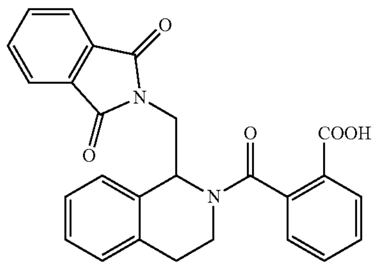

LH603: [2-(1-((1,3-dioxoisoindolin-2-yl)methyl)-1,2,3,4-tetrahydroisoquinoline-2-carbonyl) benzoic acid] (SM-II-93). White powder (Yield=72%). $^1$H NMR (DMSO-d6, 400 MHz): δ 12.9 (s, 1H), 7.9 (d, 1H), 7.83 (m, 3H), 7.70 (m, 2H), 7.49 (td, 1H), 7.39 (td, 1H), 7.10 (m, 4H), 6.0 (dd, 1H), 4.1 (dd, 1H), 3.91 (dd, 1H), 3.59 (m, 1H), 3.31 (m, 1H), 2.83 (m, 1H), 2.68 (m, 2H). MS (ESI+) m/z 441.3 (M+H).

Example 2

LH605

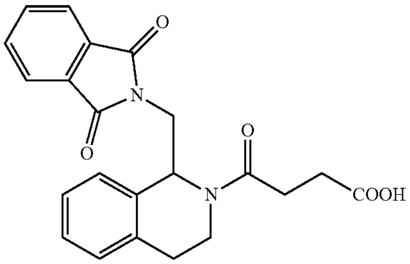

LH605: [4-(1-((1,3-dioxoisoindolin-2-yl)methyl)-3,4-dihydroisoquinolin-2(1H)-yl)-4-oxobutanoic acid] (SM-II-99). White powder (Yield=55%), $^1$H NMR ($CDCl_3$, 400 MHz): δ 12.8 (s, 1H), 7.77 (m, 2H), 7.65 (m, 2H), 7.34 (dd, 1H), 7.18 (m, 3H), 5.93 (dd, 1H), 3.99 (dd, 1H), 3.88 (dd, 1H), 3.77 (m, 2H), 2.91 (m, 2H), 2.53 (m, 2H), 2.31 (m, 2H). MS (ESI+) m/z 394.2 (M+H).

Example 3

LH639

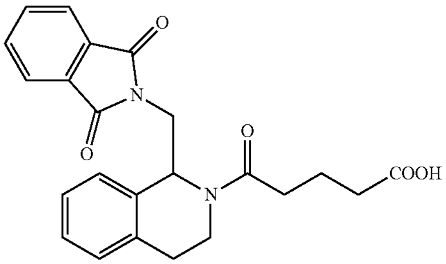

LH639: [5-(1-((1,3-dioxoisoindolin-2-yl)methyl)-3,4-dihydroisoquinolin-2(1H)-yl)-5-oxopentanoic acid] (SM-II-101). White powder (Yield=77%). $^1$H NMR ($CDCl_3$, 400 MHz): δ 12.8 (s, 1H), 7.79 (m, 2H), 7.68 (m, 2H), 7.35 (dd, 1H), 7.15 (m, 3H), 5.95 (dd, 1H), 5.95 (dd, 1H), 4.00 (dd, 1H), 3.89 (dd, 1H), 3.76 (m, 2H), 2.87 (m, 2H), 2.25 (m, 2H), 2.02 (m, 2H), 1.63 (m, 2H). MS (ESI+) m/z: 407.2 (M+H).

Example 4

LH601A-D

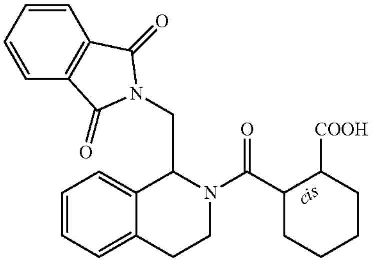

LH601 (A-D): [cis-2-(1-((1,3-dioxoisoindolin-2-yl (methyl)-1,2,3,4-tetrahydroisoquinoline-2-carbonyl)cyclo hexanecarboxylic acid] (SM-II-120). Cis-1,2-Cyclohexanedicarboxylic anhydride used. An equal mixture of all four isomers. White powder (Yield=74%). Diastereomeric and obtained enantiomeric pairs separated by ISCO and Chiral HPLC respectively. LH601A (SRS) and LH601B (RSR): $^1$H NMR ($CDCl_3$, 400 MHz): δ 12.9 (s, 1H), 7.72 (m, 4H), 7.32 (d, 1H), 7.17 (m, 3H), 6.0 (d, 1H), 4.02 (t, 1H), 3.86 (dd, 1H), 3.74 (d, 1H), 2.91 (m, 3H), 2.48 (bs, 1H), 2.10 (m, 2H), 1.30 (m, 7H). MS (ESI+) m/z 447.3 (M+H). LH601C (SSR) and LH601D (RRS): $^1$H NMR ($CDCl_3$, 400 MHz): δ 12.9 (s, 1H), 7.73 (m, 4H), 7.32 (d, 1H), 7.17 (m, 3H), 5.95 (d, 1H), 4.03 (t, 1H), 3.86 (m, 2H), 2.91 (m, 3H), 2.20 (m, 2H), 1.36 (m, 8H). MS (ESI+) m/z 447.3 (M+H).

Example 5

LH608

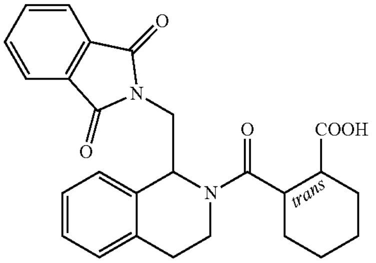

LH608: [trans-2-(1-((1,3-dioxoisoindolin-2-yl)methyl)-1,2,3,4-tetrahydroisoquinoline-2-carbonyl)cyclo hexanecarboxylic acid] (SM-II-153). trans-1,2-Cyclohexanedicarboxylic anhydride used. White powder (Yield=85%). An equal mixture of all four isomers. $^1$H NMR ($CDCl_3$, 400 MHz): δ 12.9 (s, 1H), 7.69 (m, 4H), 7.31 (m, 1H), 7.12 (m, 3H), 5.96 (d, 1H), 4.02 (m, 2H), 3.86 (dd, 1H), 3.74 (m, 2H), 2.63 (m, 6H), 1.51 (m, 2H), 1.30 (m, 6H). MS (ESI+) m/z 447.3 (M+H).

Example 6

LH655A and C

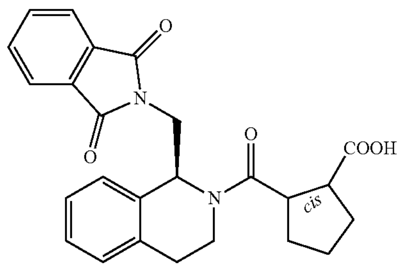

LH655 (A&D): [cis-2-(1-((1,3-dioxoisoindolin-2-yl) methyl)-1,2,3,4-tetrahydroisoquinoline-2-carbonyl) cyclohexanecarboxylic acid] (SM-III-6). Cis-1,2-Cyclohexanedicarboxylic anhydride and chiral S-amine (resolved using 2,3 Dibenzoyl-L-tartaric acid) were used. White powder (Yield=62%). Diastereomeric and obtained enantiomeric pairs separated by ISCO and Chiral HPLC respectively. $^1$H NMR ($CDCl_3$, 400 MHz): δ 12.9 (s, 1H), 7.71 (m, 4H), 7.30 (d, 1H), 7.16 (m, 3H), 5.96 (d, 1H), 4.03 (t, 1H), 3.88 (dd, 1H), 3.76 (d, 1H), 2.90 (m, 3H), 2.48 (bs, 1H), 2.12 (m, 2H), 1.32 (m, 511). MS (ESI+) m/z 432.2 (M+H).

Example 7

Scheme 5

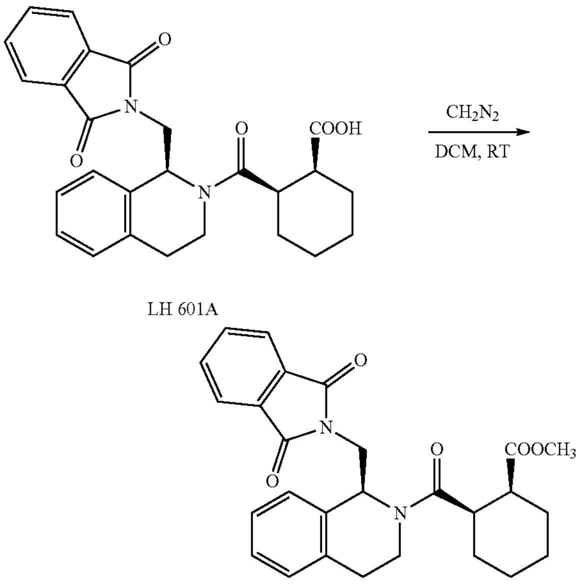

LH 601A

LH 611A

Synthesis of LH611A [Methyl (1S,2R)-2-((S)-1-((1,3-dioxoisoindolin-2-yl)methyl)-1,2,3,4-tetrahydroisoquinoline-2-carbonyl)cyclohexanecarboxylate]: Methylation reaction started from LH601A with diazomethanea at room temperature. After methylation, the solvent was removed under vacuum. MS (ESI+) m/z 447.3 (M+H).

Example 8

Scheme 6

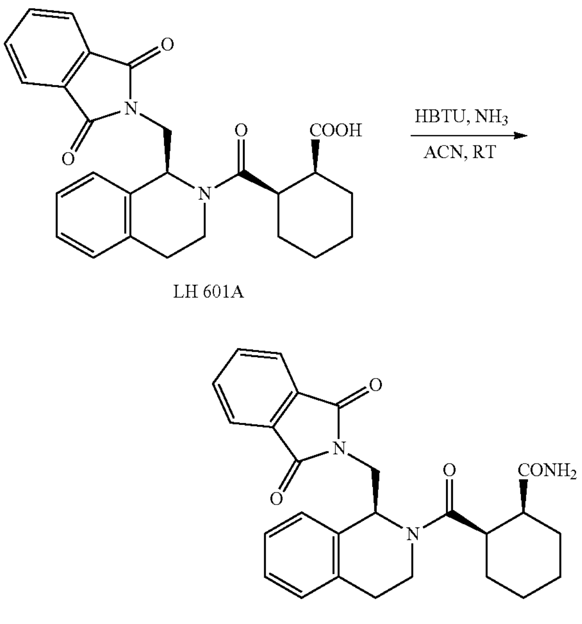

LH 601A

LH 612A

Synthesis of LH612A [(1S,2R)-2-((S)-1-((1,3-dioxoisoindolin-2-yl)methyl)-1,2,3,4-tetrahydroisoquinoline-2-carbonyl)cyclohexanecarboxamide]: HBTU was added to a solution of LH601A in acetonitrile and stirred for 30 min at room temperature. Then anhydrous ammonium was bubble into the reaction mixture for 1 min. The reaction mixture was concentrated and the residure was purified by column chromatography using acetonitrile (0 to 20%) in DCM as eluent to give the designed product. $^1$H-NMR (400 MHz, $CD_3OD$-$d_4$): δ 7.89-7.81 (m, 4H), 7.51-7.22 (m, 4H), 5.99 (dd, J=4, 8 Hz, 1H), 4.12 (dd, J=8, 12 Hz, 1H), 4.12-3.98 (m, 1H), 3.86 (dd, J=4, 16 Hz, 1H), 3.81-3.73 (m, 2H), 3.23-3.12 (m, 1H), 2.91-2.86 (m, 1H), 2.35-2.29 (m, 1H), 2.21-1.97 (m, 1H), 1.82-1.67 (m, 2H), 1.55-1.41 (m, 2H), 1.32-0.98 (m, 2H), 1.01-0.58 (m, 1H). MS (ESI+) m/z 446.2 (M+H).

Example 9

Scheme 7

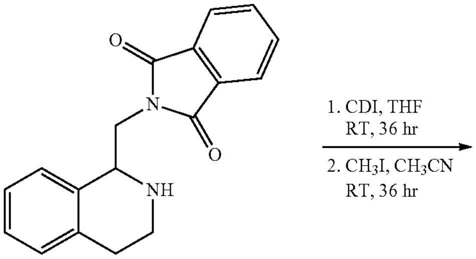

-continued

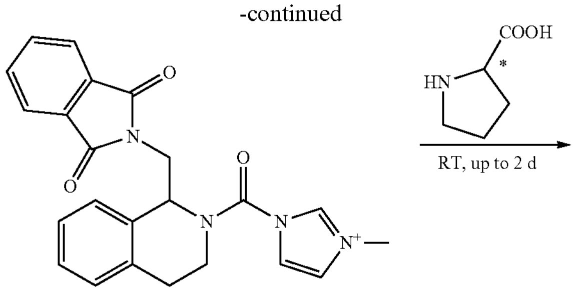

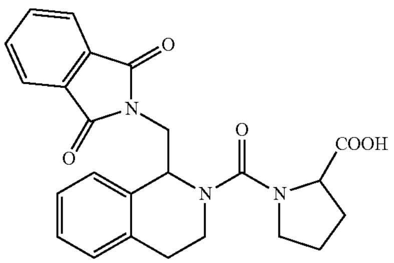

LH743

Synthesis of LH743 [1-(1-((3-dioxoisoindolin-2-yl) methyl)-1,2,3,4-tetrahydroisoquinoline-2-carbonyl) pyrrolidine-2-carboxylic acid] (SM-III-186): 3,4-Dihydro-1-phthalimidomethyl-isoquinoline (145 mg, 0.5 mmol) was dissolved in THF (2 mL) and CDI (243 mg, 1.5 mmol) was added to the solution and stirred at RT for 36 hrs. The reaction mixture was diluted with DCM (10 mL) and washed with water (2×10 mL), then dried and concentrated. The crude was dissolved in $CH_3CN$ (2 mL) and $CH_3I$ (125 μL, 2 mmol) was added and stirred at RT for 36 hrs, then concentrated in vacuo. The obtained crude was dissolved in DCM (2 mL) and DL-proline (230 mg, 2 mmol) was added to the solution and stirred at RT for 24 hrs. The obtained crude was purified via column chromatography (ISCO) using $CH_3OH$ (0 to 5% with) in DCM as eluent and fractions were concentrated to give 24 mg of product (24%). Diastereomeric pairs could be separated during column chromatography (ISCO). $^1H$ NMR (DMSO-d6, 400 MHz): δ 10.88 (s, 1H), 7.62 (m, 4H), 6.85 (m, 4H), 5.52 (dd, 1H), 3.35 (m, 8H), 1.65 (m, 5H). MS (ESI+) m/z 434.3 (M+H).

Example 10

Scheme 8

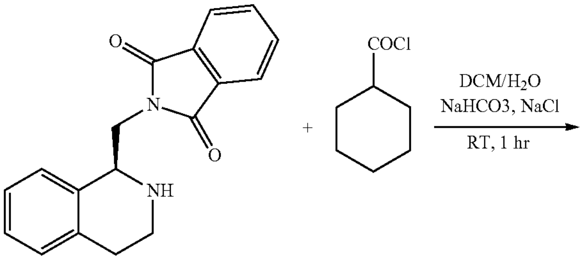

-continued

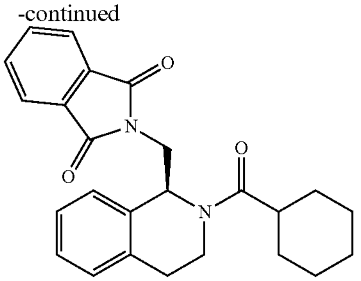

LH653

Synthesis of LH653 [(S)-2-((2-(cyclohexanecarbonyl)-1,2,3,4-tetrahydroisoquinolin-1-yl)methyl) isoindoline-1,3-dione] (SM-II-180): The chiral S-amine (resolved using 2,3 Dibenzoyl-L-tartaric acid) (13.5 mg, 0.046 mmol) was dissolved in 1 mL of DCM and 1 mL of water was added. $NaHCO_3$ and NaCl (50 mg each) were added to the biphasic mixture and cyclohexanecarbonyl chloride (18 μL, 0.138 mmol) was added slowly ands stirred at RT vigorously for 1 hr. The organic layer separated and washed with waster and brine (2 mL each), dried and concentrated. The obtained precipitate was filtered and washed with hexane and dried to get 9 mg (50%) of product. $^1H$ NMR ($CDCl_3$, 400 MHz): δ 7.79 (m, 4H), 7.21 (m, 4H), 5.54 (dd, 1H), 4.35 (td, 1H), 3.89 (m, 2H), 3.34 (m, 2H), 2.53 (m, 3H), 1.86 (m, 2H), 1.42 (m, 8H). MS (ESI+) m/z 403.2 (M+H).

Synthesis of Analogs Containing Replacements for or Substitutions on the Phthalimido Group

Example 11

Scheme 9

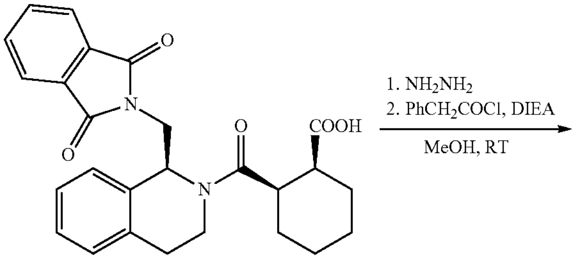

LH601

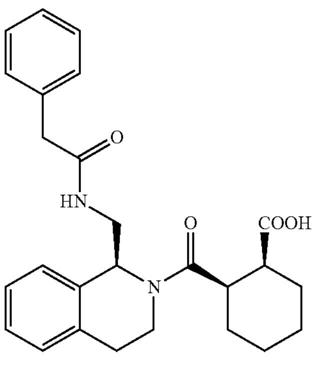

LH638

Synthesis of LH638 [(1S,2R)-2-((S)-1-((2-phenylacetamido)methyl)-1,2,3,4-tetrahydroisoquinoline-2-carbonyl) cyclohexanecarboxylic acid]: Hydrazine was added to a solution of LH601 in methanol and stirred for 1 h at room temperature. The precipitate was filtered off and the filtrate was concentrated and dried over vacuum. Then phenylacetyl chloride and DIPEA were added to a solution of the dried residue in acetonitrile and stirred for 2 h at room temperature. The reaction mixture was concentrate and the residue was purified by column chromatography using acetonitrile (0 to 20%) in DCM as eluent to give the designed product (mixture of diastereomers). $^1$H-NMR (400 MHz, $CD_3OD$-$d_4$): δ 7.57-7.50 (m, 4H), 7.35-7.19 (m, 5H), 5.90 (dd, J=4, 8 Hz, 1H), 4.72 (s, 2H), 4.00-3.81 (m, 2H), 3.72-3.68 (m, 1H), 3.61 (dd, J=4, 16 Hz, 1H), 3.03-2.66 (m, 4H), 2.23-2.12 (m, 1H), 2.11-2.02 (m, 2H), 1.90-1.73 (m, 2H), 1.68-1.48 (m, 2H), 1.33-1.05 (m, 1H). MS (ESI+) in/z 435.2 (M+H).

mL) and water (25 mL) and organic layer was washed again with water and brine, and then concentrated. The crude oil was purified via column chromatography (ISCO) using Ethyl acetate (0 to 100%) in Hexane as eluent and fractions were concentrated to give 1.23 g of clear oil (66%). $^1$H NMR ($CDCl_3$, 400 MHz): δ 7.12 (m, 4H), 4.80 (dd, 1H), 4.59 (t, 1H), 3.98 (t, 1H), 3.88 (td, 1H), 3.03 (td, 1H), 2.86 (m, 1H), 2.62 (dd, 1H), 1.12 (s, 9H). MS (ESI+) m/z 263.2 (M+H).

General procedure for the synthesis of substituted phthalimidomethyl —N-Boc protected THIQ derivatives: N-Boc protected methylamino-1,2,3,4-tetrahydroisoquinoline (0.1-

Scheme 10

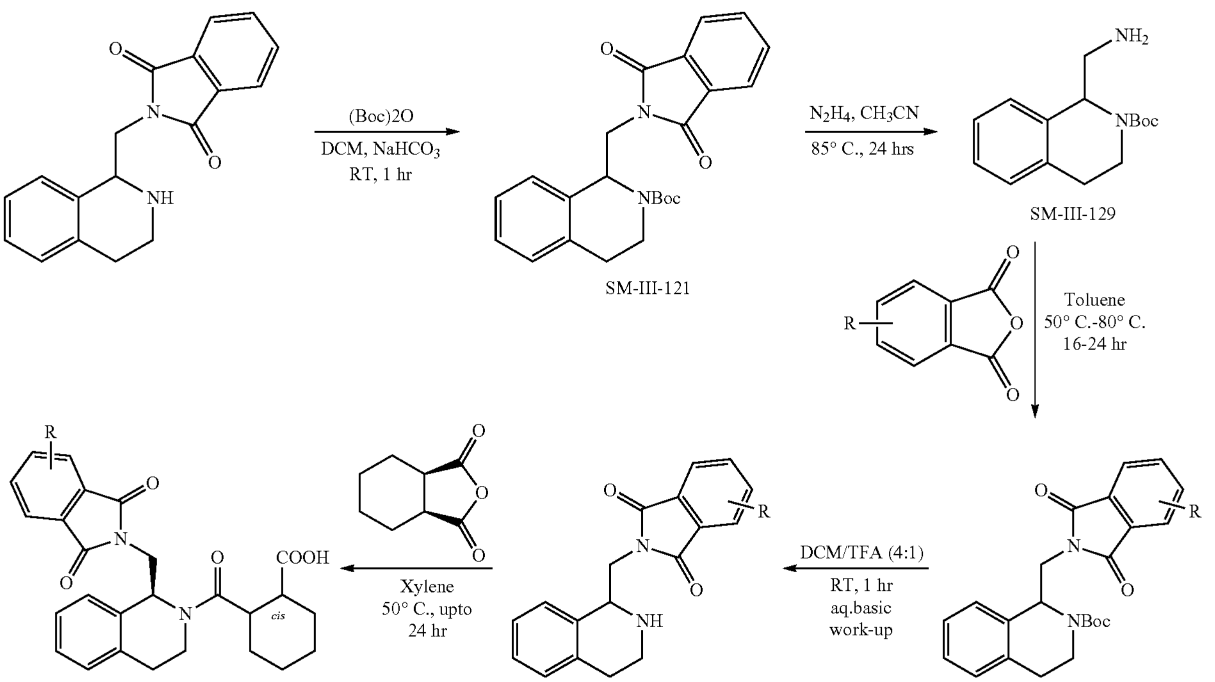

Synthesis of tert-butyl 1-(phthalimidomethyl)-3,4-dihydroisoquinoline-2(1H)-carboxylate (SM-III-121): 1-phthalimidomethyl-1,2,3,4-tetrahydroisoquinoline (1.2 g, 3.4 mmol) was dissolved in DCM (25 mL) and $(Boc)_2O$ (17 mmol, 4 mL) was added slowly. Then solid NaHCO3 (1.6 g, 20 mmol) was added in portions to the reaction mixture and stirred vigorously at RT for 1 hr. Reaction mixture was diluted with DCM (25 mL) and washed with water (2×25 mL) and brine (25 mL), then dried and concentrated. The crude oil was subjected to column chromatography (ISCO) using ethyl acetate (0 to 25%) in Hexane as eluent and fractions were concentrated to give 980 mg of colorless oil (61%). $^1$H NMR ($CDCl_3$, 400 MHz): Doubling of spectrum due to rotomers (3:2). δ 7.91 (m, 2H), 7.74 (m, 2H), 7.32 (m, 4H), 5.61 and 5.46 (dd, 1H), 4.26 (m, 3H), 3.49 (m, 1H), 2.96 (m, 2H), 1.15 and 1.06 (s, 9H). MS (ESI+) m/z 393.1 (M+H).

Synthesis of tert-butyl 1-(methyl amino)-3,4-dihydroisoquinoline-2(1H)-carboxylate (SM-III-129): N-Boc protected-phthalimidomethyl-1,2,3,4-tetrahydroisoquinoline (2.5 g, 6.3 mmol) was dissolved in $CH_3CN$ (25 mL) and anhydrous $NH_2.NH_2$ (63 mmol, 3.2 mL) was added slowly. The reaction mixture was heated at 85° C. for 24 hrs and solvent was evaporated under reduced pressure. The obtained purple color solid was partitioned with DCM (25

0.35 mmol) was dissolved in 1-3 mL of Toluene and anhydride (1.5 eq) was added and stirred at 50° C. for 1-3 hrs, then heated at 80° C. up to 24 hrs. The solvent was evaporated and crude was purified via column chromatography (ISCO) using Ethyl acetate (0 to 30%) in Hexane as eluent.

Intermediates

SM-III-164

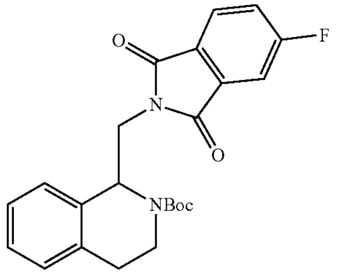

tert-butyl 1-((5-fluoro-1,3-dioxoisoindolin-2-yl)methyl)-3,4-dihydroisoquinoline-2(1H)-carboxylate (SM-III-164):

(Yield=64%). $^1$H NMR ($CDCl_3$, 400 MHz): Doubling of spectrum due to rotomers (1:1). δ 7.58 (m, 3H), 7.29 (m, 4H), 5.44 and 5.32 (dd, 1H), 3.9 (m, 3H), 3.32 (m, 1H), 2.75 (m, 2H), 1.08 and 0.99 (s, 9H). MS (ESI++) M/Z 411.2 (M+H).

SM-III-156

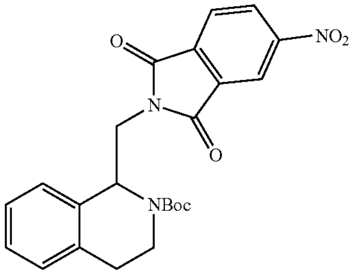

tert-butyl 1-((5-nitro-1,3-dioxoisoindolin-2-yl)methyl)-3,4-dihydroisoquinoline-2(1H)-carboxylate (SM-III-156): (Yield=47%). $^1$H NMR ($CDCl_3$, 400 MHz): Doubling of spectrum due to rotomers (3:2). δ 8.59 and 8.49 (s, 1H), 8.56 and 8.38 (d, 1H), 7.94 and 8.38 (d, 1H), 7.15 (m, 4H), 5.55 and 5.49 (dd, 1H), 3.88 (m, 3H), 3.29 (m, 1H), 2.74 (m, 2H), 0.99 and 0.87 (s, 9H). MS (ESI+) M/Z 438.3 (M±H).

SM-III-143

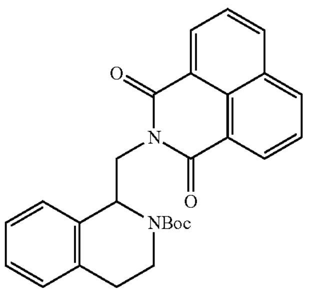

(SM-III-143): (Yield=50%). $^1$H NMR ($CDCl_3$, 400 MHz): Doubling of spectrum due to rotomers (3:2). δ 8.72 (dd, 1H), 8.26 and 8.21 (d, 1H), 7.79 (m, 1H), 7.19 (m, 4H), 5.88 and 5.68 (dd, 1H), 4.85 (m, 2H), 4.29 (m, 2H), 3.53 (m, 1H), 2.93 (m, 1H), 0.95 and 0.80 (s, 9H). MS (ESI+) M/Z 443.2 (M+H).

TK-I-13

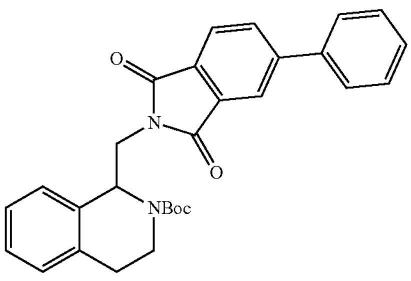

tert-butyl-1-((1,3-dioxo-5-phenylisoindolin-2-yl)methyl)-3,4-dihydroisoquinoline-2(1H)-carboxylate (TK-I-13): $^1$H NMR ($CDCl_3$, 400 MHz): Doubling of spectrum due to rotomers (3:2). δ 8.46 (m, 8H), 7.19 (m, 4H), 5.22 and 5.12 (dd, 1H), 3.87 (m, 3H), 3.26 (m, 1H), 2.72 (m, 2H), 0.97 and 0.85 (s, 9H). MS (ESI+) m/z 438.3 (M+H).

SM-IV-4

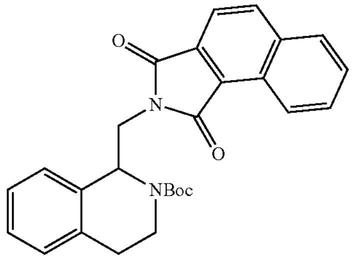

tert-butyl 1-((1,3-dioxo-1H-benzo[e]isoindol-2(3H)-yl)methyl)-3,4-dihydroisoquinoline-2(1H)-carboxylate (SM-IV-4): (Yield=61%). $^1$H NMR ($CDCl_3$, 400 MHz): Doubling of spectrum due to rotomers (3:2). δ 8.91 (d, 1H), 8.12 (d, 1H), 7.86 (m, 2H), 7.61 (m, 1H), 7.33 (td, 1H), 7.15 (m, 4H), 5.43 and 5.40 (dd, 1H), 4.02 (m, 3H), 3.36 (m, 1H), 2.83 (m, 2H), 0.95 and 0.87 (s, 9H). MS (ESI+) m/z 443.3 (M+H).

SM-IV-7

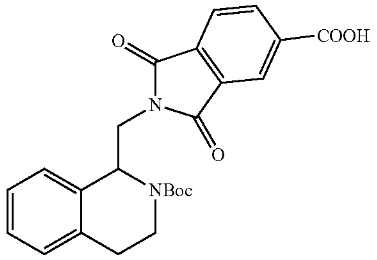

2-((2-(tert-butoxycarbonyl)-1,2,3,4-tetrahydroisoquinolin-1-yl)methyl)-1,3-dioxoisoindoline-5-carboxylic acid (SM-IV-7): (Yield=37%). $^1$H NMR ($CDCl_3$, 400 MHz): Doubling of spectrum due to rotomers (3:2). δ 12.7 (s, 1H), 8.23 (m, 3H), 7.13 (m, 4H), 5.55 and 5.49 (dd, 1H), 3.88 (m, 3H), 3.29 (m, 1H), 2.74 (m, 2H), 0.99 and 0.87 (s, 9H). MS (ESI+) m/z 437.2 (M+H).

General procedure for the synthesis of substituted phthalimidomethyl THIQ-2-carbonyl carboxylic acids: substituted phthalimidomethyl —N-Boc protected THIQ (0.05-0.1 mmol) was dissolved DCM (1-2 ml) and TFA (250 μL to 500 μL) was added. The solution was stirred at RT for 1 hr and evaporated to dryness and diluted with DCM (2-5 mL) and washed with aq. $NaHCO_3$ and brine. The organic layer was dried and concentrated under reduced pressure to the residue which was dissolved in 1-2 mL of Xylene. Then Cis-1,2-Cyclohexanedicarboxylic anhydride (1.1 eq) was added slowly at 50° C. for 16-24 hrs. The obtained precipitate was filtered and washed with diethyl ether and dried. Impure final products were purified via column chromatography (ISCO) using Ethyl acetate (0 to 100% with 1% AcOH) in Hexane as eluent. Some diastereomeric pairs were separated during column chromatography (ISCO) using $CH_3CN$ (0 to 20% with 1% AcOH) in DCM.

Example 12

LH-727

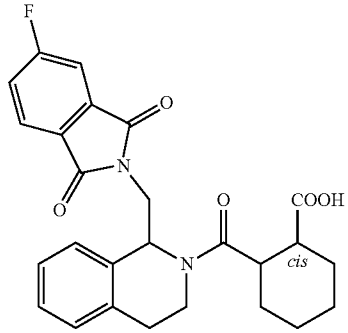

LH727: [cis-2-(1-((5-fluoro-1,3-dioxoisoindolin-2-yl) methyl)-1,2,3,4-tetrahydroisoquinoline-2-carbonyl) cyclohexanecarboxylic acid] (SM-III-177). Cis-1,2-Cyclohexanedicarboxylic anhydride used. An equal mixture of all four isomers. White powder (Yield=74%). Diastereomeric pairs could be separated by ISCO column chromatography. $^{1}H$ NMR ($CDCl_3$, 400 MHz): δ 12.89 (s, 1H), 7.85 (dd, 1H), 7.57 (dd, 1H), 7.41 (td, 1H), 7.24 (m, 4H), 6.06 (dd, 1H), 3.99 (m, 3H), 3.40 (td, 1H), 2.85 (m, 2H), 2.91 (m, 2H), 2.22, (m, 2H), 1.540 (m, 6H). MS (ESI+) m/z 465.2 (M+H).

Example 13

LH728

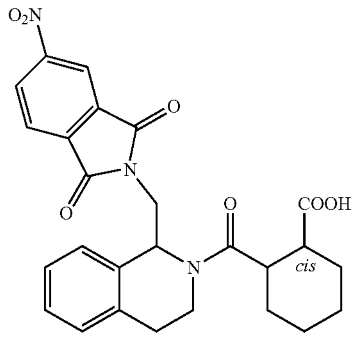

LH728: [cis-2-(1-((5-nitro-1,3-dioxoisoindolin-2-yl) methyl)-1,2,3,4-tetrahydroisoquinoline-2-carbonyl) cyclohexanecarboxylic acid] (SM-III-175). Cis-1,2-Cyclohexanedicarboxylic anhydride used. An equal mixture of all four isomers. White powder (Yield=52%). $^{1}H$ NMR ($CDCl_3$, 400 MHz): δ 12.90 (s, 1H), 8.22 (d, 1H), 7.85 (dd, 1H), 7.62 (dd, 1H), 7.23 (m, 4H), 6.01 (dd, 1H), 3.88 (m, 3H), 2.89 (m, 3H), 1.53 (m, 10H). MS (ESI+) m/z 492.2 (M+H).

Example 14

LH731

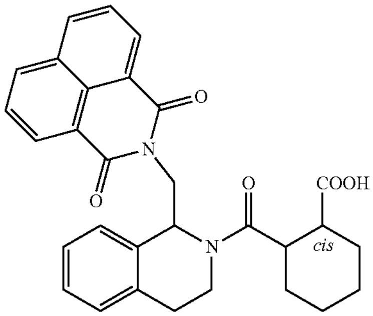

LH731 (SM-III-148): Cis-1,2-Cyclohexanedicarboxylic anhydride used. An equal mixture of all four isomers. White powder (Yield=77%). $^{1}H$ NMR ($CDCl_3$, 400 MHz): δ 12.90 (s, 1H), 7.83 (dd, 1H), 7.57 (d, 1H), 7.40 (m, 4H), 7.18 (m, 4H), 6.03 (td, 1H), 4.02 (t, 1H), 3.89 (m, 3H), 2.89 (m, 3H), 2.24 (m, 214), 1.32 (m, 8H). MS (ESI+) m/z 497.3 (M+H).

Example 15

LH737

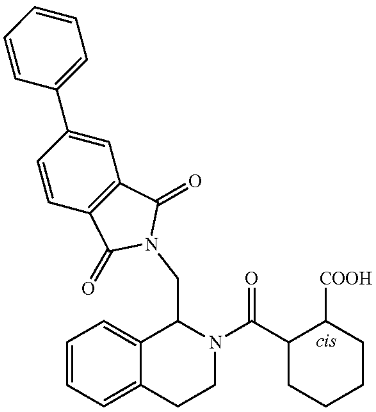

LH737 [cis-2-(1-((1,3-dioxo-5-phenylisoindolin-2-yl) methyl)-1,2,3,4-tetrahydroisoquinoline-2-carbonyl) cyclohexanecarboxylic acid] (TK-I-15): Cis-1,2-Cyclohexanedicarboxylic anhydride used. An equal mixture of all four isomers. White powder (Yield=86%). $^{1}H$ NMR ($CDCl_3$, 400 MHz): δ 12.91 (s, 1H), 7.72 (m, 8H), 7.24 (m, 4H), 5.22 (d, 1H), 4.18 (dd, 1H). 3.71 (m, 3H), 2.66 (m, 2H), 1.41 (m, 10H). MS (ESI+) in/z 523.3 (M+H).

Example 16

LH748

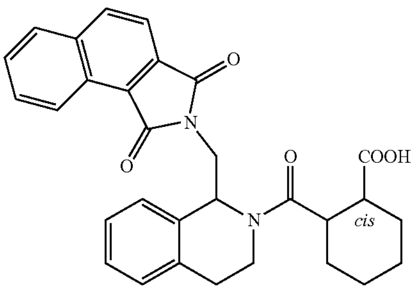

LH748 [cis-2-(1-((1,3-dioxo-1H-benzo[e]isoindol-2(3H)-yl)methyl)-1,2,3,4-tetrahydroisoquinoline-2-carbonyl) cyclohexanecarboxylic acid] (SM-IV-12): Cis-1,2-Cyclohexanedicarboxylic anhydride used. An equal mixture of all four isomers. White powder (Yield=79%). $^{1}H$ NMR ($CDCl_3$, 400 MHz): δ 12.90 (s, 1H), δ 8.91 (d, 1H), 8.06 (d, 1H), 8.12 (dd, 1H), 7.86 (dd, 1H), 7.59 (m, 2H), 7.22 (m, 4H), 6.01 (td, 1H), 4.03 (m, 4H), 2.81 (m, 2H) 1.52 (m, 8H). MS (ESI+) m/z 497.3 (M+H).

Example 17

LH751

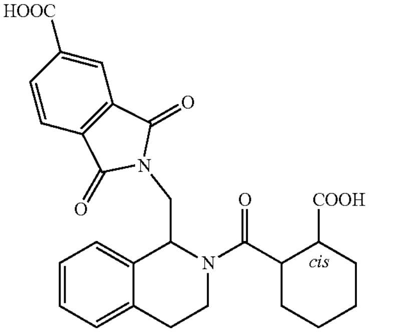

LH751 [cis-2-((2-(2-carboxycyclohexanecarbonyl)-1,2,3,4-tetrahydroisoquinolin-1-yl)methyl)-1,3-dioxoiso indoline-5-carboxylic acid] (SM-IV-15): Cis-1,2-Cyclohexanedicarboxylic anhydride used. White powder (Yield=49%). $^{1}H$ NMR ($CDCl_3$, 400 MHz): δ 12.89 (s, 1H), 12.7 (s, 1H), 8.31 (m, 3H), 7.22 (m, 4H), 6.01 (td, 1H), 3.88 (m, 3H), 2.89 (m, 3H), 1.55 (m, 10H). MS (ESI+) m/z 491.2 (M+H).

Example 18

Scheme 11

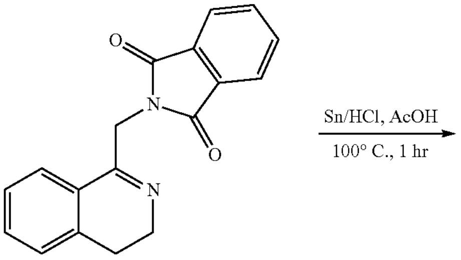

-continued

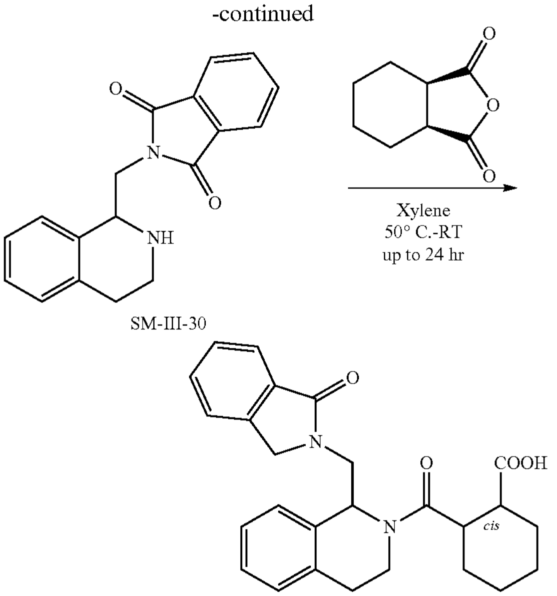

SM-III-30

LH677

Synthesis of 2-((1,2,3,4-tetrahydroisoquinoline-1-yl)methyl)isoindolin-1-one (SM-III-30): 3,4-Dihydro-1-phthalimidomethyl-isoquinoline (145 mg, 0.5 mmol) was dissolved in AcOH (4 mL) and Conc. HCl (2 mL) was added to the solution slowly. Tin metal powder was added and the obtained suspension was heated at 100° C. for 1 hr and reaction mixture was concentrated and diluted with DCM (20 mL) and basified with 0.1N aq. NaOH (8 mL) and filtered through a short bed of Celite and washed with excess of MeOH. The filtrate and washings were combined and concentrated in vacuo. The obtained crude was purified via column chromatography (ISCO) using Ethyl acetate (25 to 100% with 1% $Et_3N$) in Hexane as eluent and fractions were concentrated to give 81 mg of light yellow colored product (52%). $^{1}H$ NMR ($CDCl_3$, 400 MHz): δ 7.74 (d, 1H), δ 7.52 (td, 1H), 7.41 (m, 2H), 7.15 (m, 4H), 4.81 (d, 1H), 4.47 (dd, 1H), 4.40 (dd, 1H), 4.34 (d, 1H), 4.00 (m, 1H), 3.83 (dd, 1H), 3.24 (m, 1H), 2.96 (m, 1H), 2.71 (m, 2H). 1.71 (m, 1H). MS (ESI+) m/z 279.3 (M+H).

Synthesis of LH677 [cis-2-(1-((1-oxoisoindolin-2-yl)methyl)-1,2,3,4-tetrahydroisoquinoline-2-carbonyl) cyclohexanecarboxylic acid] (SM-III-39): The amine (SM-III-30, 56 mg, 0.2 mmol) was dissolved in 2 mL of Xylene and Cis-1,2-Cyclohexanedicarboxylic anhydride (1.1 eq) was added slowly at 50° C. for 1 hr, then stirred at RT for 24 hrs. The obtained precipitate was filtered and washed with hexane (with 20% ethyl acetate) and dried to get 64 mg (74%) of white powder. Diastereomeric pairs could be separated during column chromatography (ISCO) using $CH_3CN$ (0 to 20% with 1% AcOH) in DCM. $^{1}H$ NMR ($CDCl_3$, 400 MHz): δ 7.68 (d, 1H), 7.49 (td, 1H), 7.38 (m, 2H), 7.15 (m, 4H), 5.88 (dd, 1H), 4.82 (d, 1H), 4.41 (dd, 1H), 4.26 (d, 1H), 4.01 (m, 1H), 3.75 (m, 1H), 3.37 (dd, 1H), 2.92 (m, 2H), 2.92 (m, 3H), 1.55 (m, 8H). MS (ESI+) m/z 433.3 (M+H).

Example 19

Scheme 12

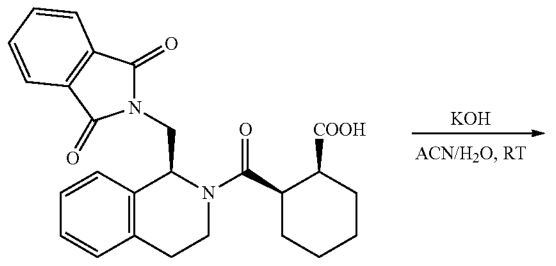

LH 601A

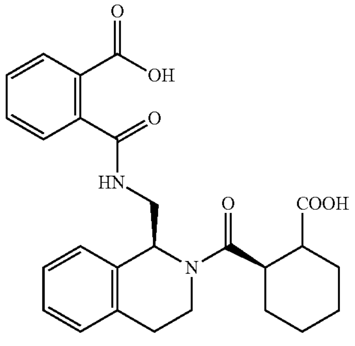

LH 613

LH613 [2-((((S)-2-((1R,2S)-2-carboxycyclohexanecarbonyl)-1,2,3,4-tetrahydroisoquinolin-1-yl)methyl)carbamoyl) benzoic acid]: KOH (1.5 eq) was added to a solution of LH601A in 50% ACN/$H_2O$ and stirred for 1 h at room temperature. The acetonitrile was removed and pH was adjusted to acidic and then ether was added. The resulted precipitate was collected by filtration and dried over vacuum to give the product (mixture of diastereomers). $^1$H-NMR (400 MHz, $CD_3OD$-$d_4$): δ 7.73-7.60 (m, 4H), 7.31-7.09 (m, 4H), 5.96 (dd, J=4, 8 Hz, 1H), 4.01 (dd, J=8, 12 Hz, 1H), 3.81-3.52 (m, 2H), 3.46-3.41 (m, 1H), 3.22-3.09 (m, 1H), 3.05-2.87 (m, 1H), 2.69-2.43 (m, 2H), 2.38-2.26 (m, 2H), 2.17-2.06 (m, 2H), 2.03-1.50 (m, 2H), 1.49-0.86 (m, 2H). MS (ESI+) m/z 477.2 (M+H).

Example 20

Scheme 13

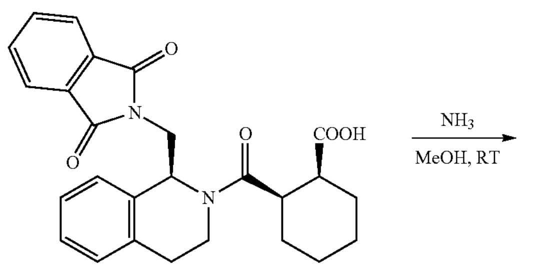

LH 601A

-continued

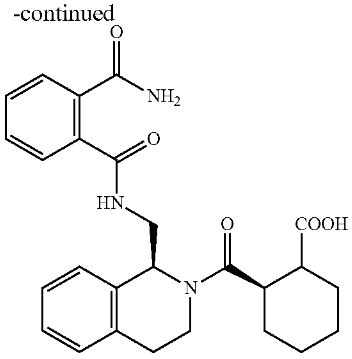

LH 627

LH627 [(1S,2R)-2-((S)-1-((2-carbamoylbenzamido) methyl)-1,2,3,4-tetrahydroisoquinoline-2-carbonyl) cyclohexanecarboxylic acid]: Anhydrous ammonium was bubbled into a solution of LH601A in methanol and stirred for 2 h at room temperature. The reaction mixture was concentrated and the residue was purified by column chromatography using acetonitrile (0 to 100%) in DCM as eluent to give the designed product (mixture of diastereomers). $^1$H-NMR (400 MHz, $CD_3OD$-$d_4$): δ 7.79-7.61 (m, 4H), 7.33-7.12 (m, 4H), 5.99 (dd, J=4, 8 Hz, 1H), 4.02 (dd, J=8, 12 Hz, 1H), 3.88-3.52 (m, 2H), 3.51-3.42 (m, 1H), 3.12-3.03 (m, 1H), 3.00-2.82 (m, 2H), 2.69-2.48 (m, 2H), 2.33-2.22 (m, 2H), 2.13-2.06 (m, 1H), 2.00-1.51 (m, 2H), 1.48-0.89 (m, 2H). MS (ESI+) m/z 477.2 (M+H).

Synthesis of Analogs Containing Replacements for or Substitutions on the Tetrahydro-Isoquinoline (THIQ). Group Example 21

Scheme 14

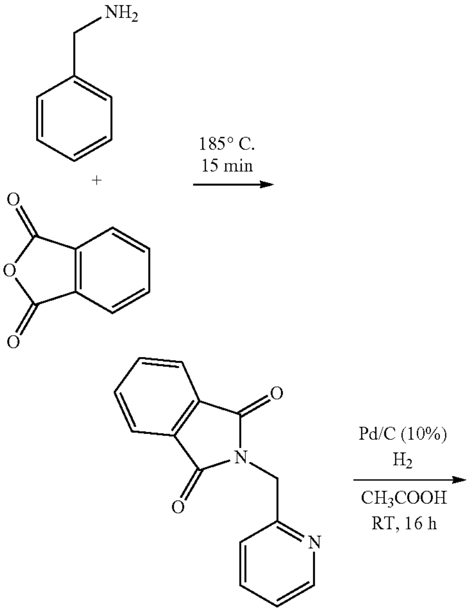

SM-II-166

-continued

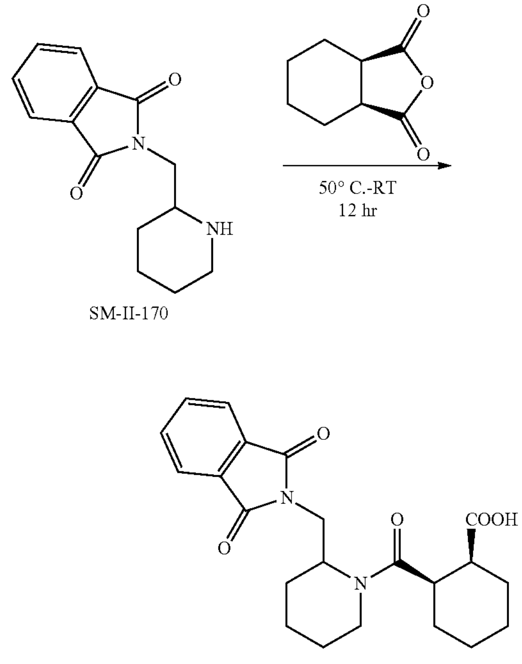

SM-II-170

LH641

Synthesis of 2-(pyridin-2-ylmethyl) isoindoline-1,3-dione (SM-II-166): 2-(Aminomethyl) pyridine (1.08 g; 10 mmol) and pththalic anhydride (1.48 g; 10 mmol) were taken together and fused at 180-185° C. with stirring for 15 min and cooled to RT. The obtained white solid was washed with ethanol and dried to get 2.1 g of product (88%). $^1$H NMR ($CDCl_3$, 400 MHz): δ 7.88 (m, 1H), 7.74 (m, 2H), 7.71 (m, 2H), 7.65 (m, 1H), 7.31 (d, 1H), 7.21 (m, 1H), 5.05 (s, 2H). MS (ESI+) m/z 239.2 (M+H).

Synthesis of 2-(piperidin-2-ylmethyl)isoindoline-1,3-dione (SM-II-170): 2-(pyridin-2-ylmethyl) isoindoline-1,3-dione (240 g, 1 mmol) was dissolved in AcOH (5 mL) and 10% Pd/C (100 mg) was added, and then reaction mixture was stirred at RT under $H_2$ (atm) for 16 hrs. The reaction mixture was filtered through a short bed of Celite and washed with excess of MeOH. The filtrate and washings were combined and concentrated in vacuo. The obtained crude was taken without further purification (~100 mg). $^1$H NMR ($CDCl_3$, 400 MHz): δ 7.73 (m, 2H), 7.69 (m, 2H), 5.01 (s, 2H), 2.11, 1.95, 1.66 (3m, 6H), 3.24 (m, 3H), MS (ESI+) m/z 245.2 (M+H).

Synthesis of LH641 [cis-2-(2-((1,3-dioxoisoindolin-2-yl) methyl)piperidine-1-carbonyl)cyclohexane carboxylic acid] (SM-II-171): The crude amine (SM-II-170, 100 mg) was dissolved in 2 mL of Xylene and Cis-1,2-Cyclohexanedicarboxylic anhydride (200 mg) was added slowly at 50° C. for 1 hr, then stirred at RT for 24 hrs. The obtained precipitate was filtered and washed with hexane (with 20% ethyl acetate) and dried to get 59 mg (~41%) of white powder. $^1$H NMR ($CDCl_3$, 400 MHz): δ 735 (m, 2H), 7.65 (m, 2H), 5.23 (d, 1H), 4.12 (m, 2H), 3.58 (m, 3H), 2.73 (m, 3H), 1.75 (m, 12H). MS (ESI+) m/z 399.4 (M+H).

Example 22

Scheme 15

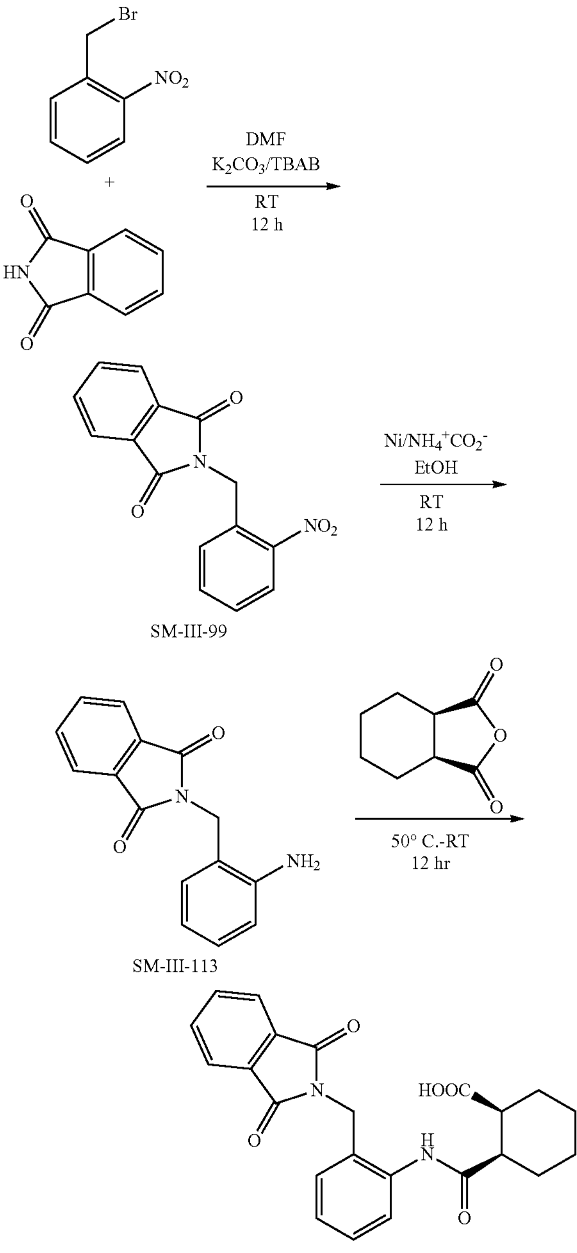

SM-III-99

SM-III-113

LH713

Synthesis of 2-(2-nitrobenzyl)isoindoline-1,3-dione (SM-III-99): 2-Nitro benzyl bromide (216 mg, 1 mmol), phthalimide (150 mg, ~1 $Bu_4NBr$ (32 mg, 0.1 mmol) and $K_2CO_3$ were taken together. DMF (5 mL) added to the reaction mixture and stirred at RT for 14 hrs. The reaction mixture was diluted with DCM (15 mL) and washed with 20% LiCl (15 mL) and water (3×10 mL), then dried and concentrated to give 226 mg of product (80%). MS (ESI+) m/z 283.2 (M+H).

Synthesis of 2-(2-aminobenzyl)isoindoline-1,3-dione (SM-III-113): 2-(2-nitrobenzyl)isoindoline-1,3-dione (140 mg, 0.5 mmol) was dissolved in EtOH (5 mL), ammonium formate (100 mg) and followed. Raney Ni was (70 mg) was added. The reaction mixture was stirred at RT for 12 hrs and then reaction was quenched with water (5 mL) and extracted with DCM (3×5 mL). The organic layer was washed with brine, dried and concentrated to the crude product. The crude was purified via column chromatography (ISCO) using Acetone (0 to 50%) in Hexane as eluent. The yield was 50 mg (42%). $^1$H NMR ($CD_3OD$, 400 MHz): δ 7.94 (m, 2H), 7.79 (m, 2H), 7.38 (t, 1H), 7.20 (m, 2H), 5.03 (s, 2H). MS (ESI+) m/z 253.2 (M+H).

Synthesis of LH713 [cis-2-(2-((1,3-dioxoisoindolin-2-yl) methyl)phenylcarbamoyl)cyclohexanecarboxylic acid] (SM-III-115): 2-(2-aminobenzyl)isoindoline-1,3-dione (SM-II-113, 50 mg) was dissolved in 2 mL of Xylene and Cis-1,2-Cyclohexanedicarboxylic anhydride (50 mg) was added slowly at 50° C. for 1 hr, then stirred at RT for 24 hrs. The obtained crude was purified via column chromatography (ISCO) using Ethyl acetate (0 to 100% with 1% AcOH) in Hexane. The yield was 48 mg (60%). $^1$H NMR ($CD_3OD$, 400 MHz): δ 7.92 (m, 2H), 7.78 (m, 2H), 7.36 (t, 1H), 7.24 (m, 2H), 5.13 (s, 2H), 2.64 (m, 2H), 1.65 (m, 8H). MS (ESI+) m/z 406.2 (M+H).

Synthesis of Analogs Containing Substitutions on the Tetrahydro-Isoquinoline (THIQ) Group General Experimental Procedure:

Same experimental conditions as given in Scheme 4, but using different substituted phenethylamines.

Example 23

LH669A [(1S,2R)-2-((S)-1-((1,3-dioxoisoindolin-2-yl)methyl)-7-methoxy-1,2,3,4 tetrahydroisoquinoline-2-carbonyl)cyclohexanecarboxylic acid]

LH669A

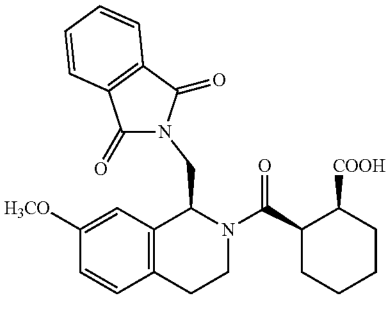

Example 24

LH669B [(1R,2S)-2-((R)-1-((1,3-dioxoisoindolin-2-yl)methyl)-7-methoxy-1,2,3,4-tetrahydroisoquinoline-2-carbonyl)cyclohexanecarboxylic acid]

LH669B

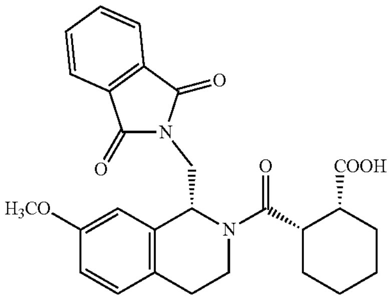

Scheme 16

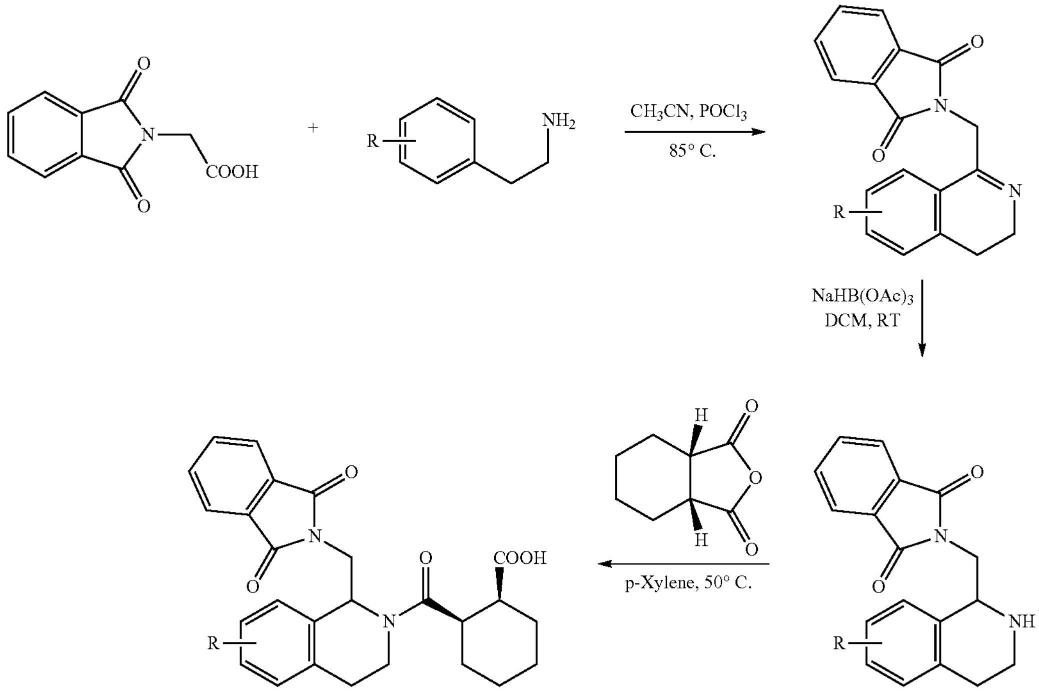

R = 4-F, 3-F, 2-F, 4-OMe, 2-OMe, 3 & 4-OMe

LH669A and LH669B: Prepared by following the general synthetic procedure and pure enantiomers were obtained by chiral HPLC separation. $^1$H-NMR (400 MHz, $CD_3OD-d_4$): δ 7.89-7.81 (m, 4H), 7.12 (d, J=8 Hz, 1H), 6.93 (s, 1H), 6.83 (d, J=4 Hz, 1H), 5.98 (dd, J=4, 8 Hz, 1H), 4.12 (dd, J=8, 12 Hz, 1H), 4.02-3.97 (m, 1H), 3.94 (dd, J=4, 16 Hz, 1H), 3.83 (s, 3H), 3.80-3.73 (m, 2H), 3.10-2.98 (m, 1H), 2.85-2.80 (m, 1H), 2.40-2.36 (m, 1H), 2.01-1.97 (m, 1H), 1.75-1.67 (m, 2H), 1.48-1.43 (m, 2H), 1.12-0.98 (m, 2H), 0.51-0.42 (m, 1H). MS (ESI+) m/z 477.2 (M+H).

Example 25

LH671A [(1S,2R)-2-((S)-1-((1,3-dioxoisoindolin-2-yl)methyl)-5-methoxy-1,2,3,4-tetrahydroisoquinoline-2-carbonyl)cyclohexanecarboxylic acid]

LH671A

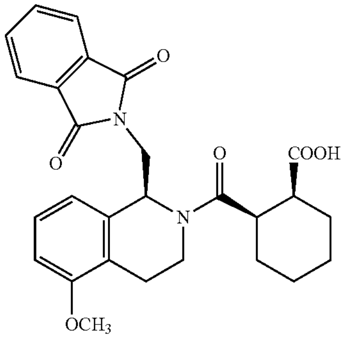

Example 26

LH671B [(1R,2S)-2-((R)-1-((1,3-dioxoisoindolin-2-yl)methyl)-5-methoxy-1,2,3,4-tetrahydroisoquinoline-2-carbonyl)cyclohexanecarboxylic acid]

LH671B

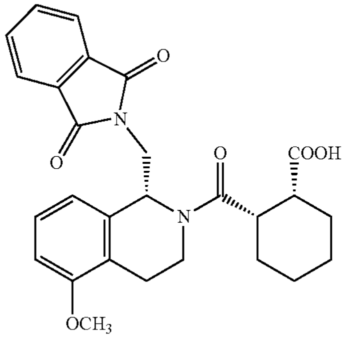

LH671A and LH671B: Prepared by following the general synthetic procedure and pure enantiomers were obtained by chiral HPLC separation. $^1$H-NMR (400 MHz, $CD_3OD-d_4$): δ 7.77-7.68 (m, 4H), 7.15 (dd, J=8, 8 Hz, 1H), 6.88 (d, J=8 Hz, 1H), 6.74 (d, J=8 Hz, 1H), 5.88 (dd, J=4, 8 Hz, 1H), 4.03 (dd, J=8, 12 Hz, 1H), 3.95 (dd, J=4, 16 Hz, 1H), 3.83 (dd, J=4, 16 Hz, 1H), 3.76 (s, 3H), 3.70-3.58 (m, 2H), 2.86-2.78 (m, 1H), 2.75-2.62 (m, 1H), 2.32-2.25 (m, 1H), 1.93-1.82 (m, 1H), 1.70-1.57 (m, 2H), 1.46-1.33 (m, 2H), 1.12-0.78 (m, 2H), 0.42-0.29 (m, 1H). MS (ESI+) in/z 477.2 (M+H).

Example 27

LH674AB [cis-2-((S)-1-((1,3-dioxoisoindolin-2-yl)methyl)-6,7-dimethoxy-1,2,3,4-tetrahydroisoquinoline-2-carbonyl)cyclohexanecarboxylic acid]

LH674A

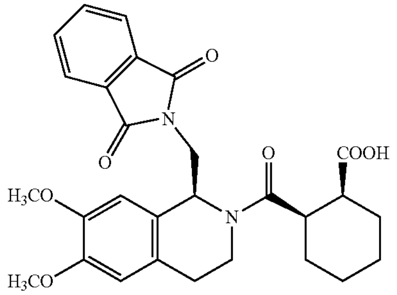

and

LH674B

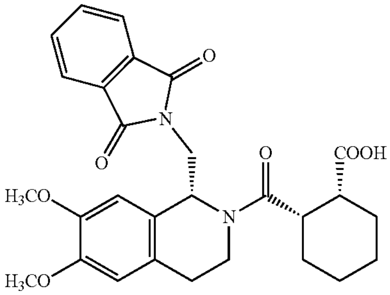

LH674AB: Prepared by following the general synthetic procedure and the diastereomers were obtained by HPLC separation. $^1$H-NMR (400 MHz, $CD_3OD-d_4$): δ 7.77-7.69 (m, 4H), 6.83 (s, 1H), 6.66 (s, 1H), 5.80 (dd, J=4, 8 Hz, 1H), 4.00 (dd, J=8, 12 Hz, 1H), 3.88 (dd, J=4, 16 Hz, 1H), 3.82 (dd, J=4, 16 Hz, 1H), 3.77 (s, 3H), 3.72 (s, 3H), 3.70-3.58 (m, 2H), 2.98-2.87 (m, 1H), 2.75-2.60 (m, 1H), 2.32-2.22 (m, 1H), 1.98-1.81 (m, 1H), 1.68-1.51 (m, 2H), 1.41-1.33 (m, 2H), 1.11-0.75 (m, 2H), 0.42-0.28 (m, 1H). MS (ESI+) m/z 507.2 (M+H).

Example 28

LH674CD [cis-2-((R)-1-((1,3-dioxoisoindolin-2-yl)methyl)-6,7-dimethoxy-1,2,3,4-tetrahydroisoquinoline-2-carbonyl)cyclohexanecarboxylic acid]

LH674C

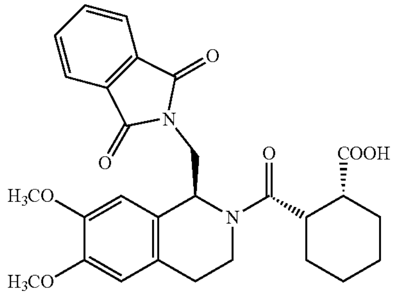

and

LH674D

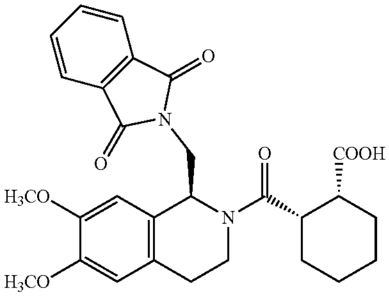

LH674CD: Prepared by following the general synthetic procedure and the diastereomers were obtained by HPLC separation. $^1$H-NMR (400 MHz, $CD_3OD-d_4$): δ 7.77-7.69 (m, 4H), 6.83 (s, 1H), 6.66 (s, 1H), 5.80 (dd, J=4, 8 Hz, 1H), 4.01 (dd, J=8, 12 Hz, 1H), 3.88 (dd, J=4, 16 Hz, 1H), 3.81 (dd, J=4, 16 Hz, 1H), 3.77 (s, 3H), 3.72 (s, 3H), 3.70-3.56 (m, 2H), 2.99-2.84 (m, 1H), 2.75-2.60 (m, 1H), 2.33-2.22 (m, 1H), 1.96-1.83 (m, 1H), 1.66-1.53 (m, 2H), 1.42-1.32 (m, 2H), 1.18-0.72 (m, 2H), 0.40-0.25 (m, 1H). MS (ESI+) m/z 507.2 (M+H).

Example 29

LH663 [2-(1-((1,3-dioxoisoindolin-2-yl)methyl)-7,8-dimethoxy-1,2,3,4-tetrahydroisoquinoline-2-carbonyl)cyclohexanecarboxylic acid]

LH663

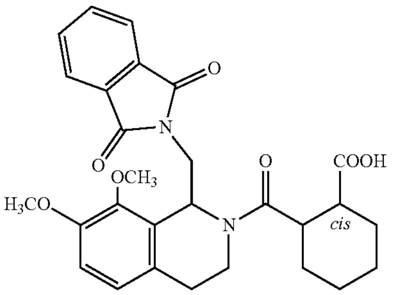

LH663: Prepared by following the general synthetic procedure (mixture of 4 isomers). $^1$H-NMR (400 MHz, $CD_3OD-d_4$): δ 7.87-7.79 (m, 4H), 6.68 (d, J=8 Hz, 1H), 6.56 (d, J=8 Hz, 1H), 5.82 (dd, J=4, 8 Hz, 1H), 4.05 (dd, J=8, 12 Hz, 1H), 3.86 (dd, J=4, 16 Hz, 1H), 3.82 (dd, J=4, 16 Hz, 1H), 3.75 (s, 3H), 3.71 (s, 3H), 3.70-3.58 (m, 2H), 2.98-2.86 (m, 1H), 2.77-2.61 (m, 1H), 2.42-2.35 (m, 1H), 1.99-1.85 (m, 1H), 1.69-1.53 (m, 2H), 1.41-1.32 (m, 2H), 1.10-0.79 (m, 2H), 0.42-0.29 (m, 1H). MS (ESI+) m/z 507.2 (M+H).

Example 30

LH700 [cis-2-(1-((1,3-dioxoisoindolin-2-yl)methyl)-7-fluoro-1,2,3,4-tetrahydroisoquinoline-2-carbonyl) cyclohexanecarboxylic acid]

LH700

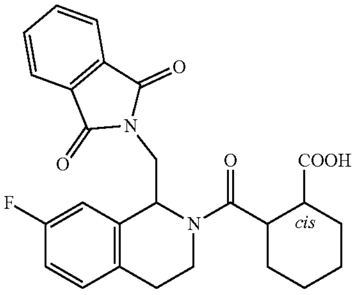

LH700: Prepared by following the general synthetic procedure (mixture of 4 isomers). $^1$H-NMR (400 MHz, $CD_3OD-d_4$): δ 7.78-7.69 (m, 4H), 7.13 (dd, J=8 Hz, 1H), 6.93 (d, 1H), 6.83 (dd, J=8 Hz, 1H), 5.92 (dd, J=4, 8 Hz, 1H), 4.02 (dd, J=8, 12 Hz, 1H), 3.92 (dd, J=4, 12 Hz, 1H), 3.80 (dd, J=4, 16 Hz, 1H), 3.66-3.60 (m, 2H), 3.10-2.90 (m, 1H), 2.85-2.80 (m, 1H), 2.30-2.26 (m, 1H), 2.01-1.97 (m, 1H), 1.70-1.50 (m, 2H), 1.48-1.43 (m, 2H), 1.12-0.99 (m, 2H), 0.49-0.38 (m, 1H). MS (ESI+) m/z 465.2 (M+H).

Example 31

LH689 [(cis-2-(1-((1,3-dioxoisoindolin-2-yl) methyl)-5-fluoro-1,2,3,4-tetrahydroisoquinoline-2-carbonyl)cyclohexanecarboxylic acid]

LH689

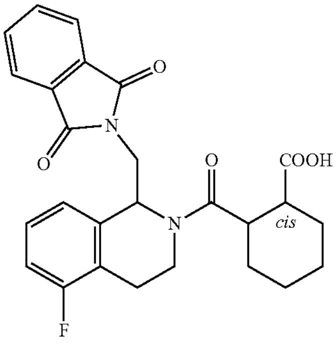

LH689: Prepared by following the general synthetic procedure (mixture of 4 isomers). $^1$H-NMR (400 MHz, $CDCl_3$-d): δ 7.78-7.50 (m, 4H), 7.21-6.82 (m, 3H), 6.02 (dd, J=4, 8 Hz, 1H), 4.18-3.50 (m, 5H), 3.11-2.41 (m, 3H), 2.33-1.71 (m, 4H), 1.29-0.082 (m, 5H). MS (ESI+) m/z 465.2 (M+H).

Example 32

Scheme 17

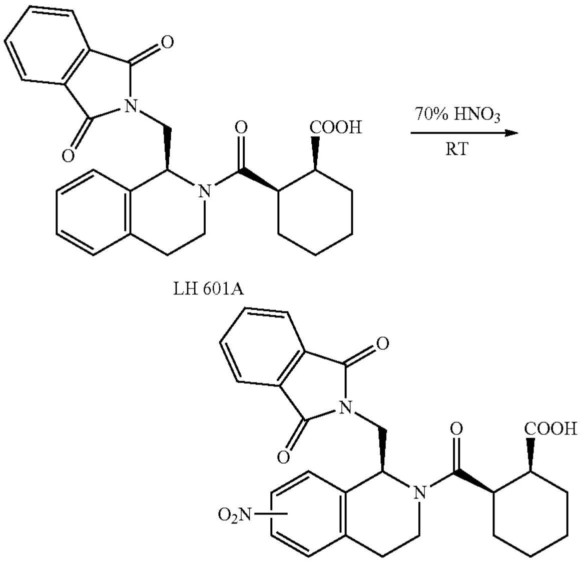

LH 601A

LH704

LH704 [(1S,2R)-2-((S)-7-(1S,2R)-2-((S)-1-((1,3-dioxoisoindolin-2-yl)methyl)-nitro-1,2,3,4-tetrahydroisoquinoline-2-carbonyl)cyclohexanecarboxylic acid]: LH601A was dissolved in 70% $HNO_3$ and stirred for 1 h at room temperature. Water was added to the solution and the resulted precipitated was collected by filtration and washed with water. The collected solid was dried over vacuum to give the product. $^1$H-NMR (400 MHz, $CD_3OD-d_4$): δ 8.15 (d, J=4 Hz, 1H), 8.01 (dd, J=4, 8 Hz, 1H), 7.80-7.69 (m, 4H), 6.01 (dd, J=4, 8 Hz, 1H), 4.12-4.03 (m, 1H), 4.01 (dd, J=8, 12 Hz, 1H), 4.01-3.92 (m, 1H), 3.81-3.73 (m, 2H), 3.13-2.88 (m, 1H), 2.85-2.73 (m, 1H), 2.30-2.26 (m, 1H), 1.91-1.87 (m, 1H), 1.72-1.55 (m, 2H), 1.48-1.31 (m, 2H), 1.02-0.80 (m, 2H), 0.50-0.32 (m, 1H). MS (ESI+) m/z, 491.2 (M+H).

Example 33

Scheme 18

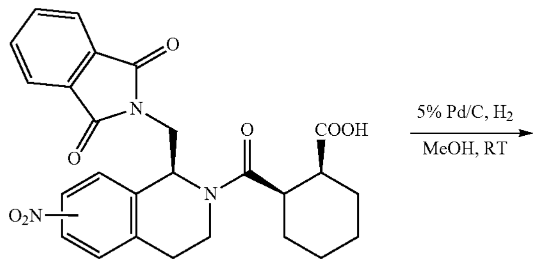

LH704

-continued

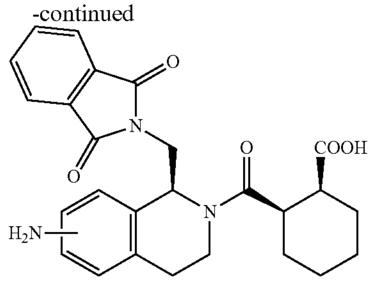

LH721

LH721 [(1S,2R)-2-((S)-amino-1-((1,3-dioxoisoindolin-2-yl)methyl)-1,2,3,4-tetrahydroisoquinoline-2-carbonyl)cyclohexanecarboxylic acid]: A catalytical amount of 5% Pd/C was added to a solution of LH704 in methanol and stirred for 2 h under $H_2$. The Pd/C was filtered off and the filtration was concentrated. The residue was purified by column chromatography using acetonitrile (0 to 100%) in DCM as eluent to give the designed product. $^1$H-NMR (400 MHz, $CD_3OD-d_4$): δ 7.79-7.69 (m, 4H), 7.13 (d, J=8 Hz, 1H), 7.11 (s, 1H), 6.93 (d, J=8 Hz, 1H), 5.96 (dd, J=4, 8 Hz, 1H), 4.02 (dd, J=8, 12 Hz, 1H), 4.02-3.92 (m, 1H), 3.86 (dd, J=4, 16 Hz, 1H), 3.81-3.73 (m, 2H), 3.13-2.98 (m, 1H), 2.81-2.76 (m, 1H), 2.30-2.26 (m, 1H), 2.01-1.87 (m, 1H), 1.72-1.57 (m, 2H), 1.48-1.41 (m, 2H), 1.12-0.98 (m, 2H), 1.11-0.82 (m, 1H). MS (ESI+) m/z 462.2 (M+H).

Scheme 19

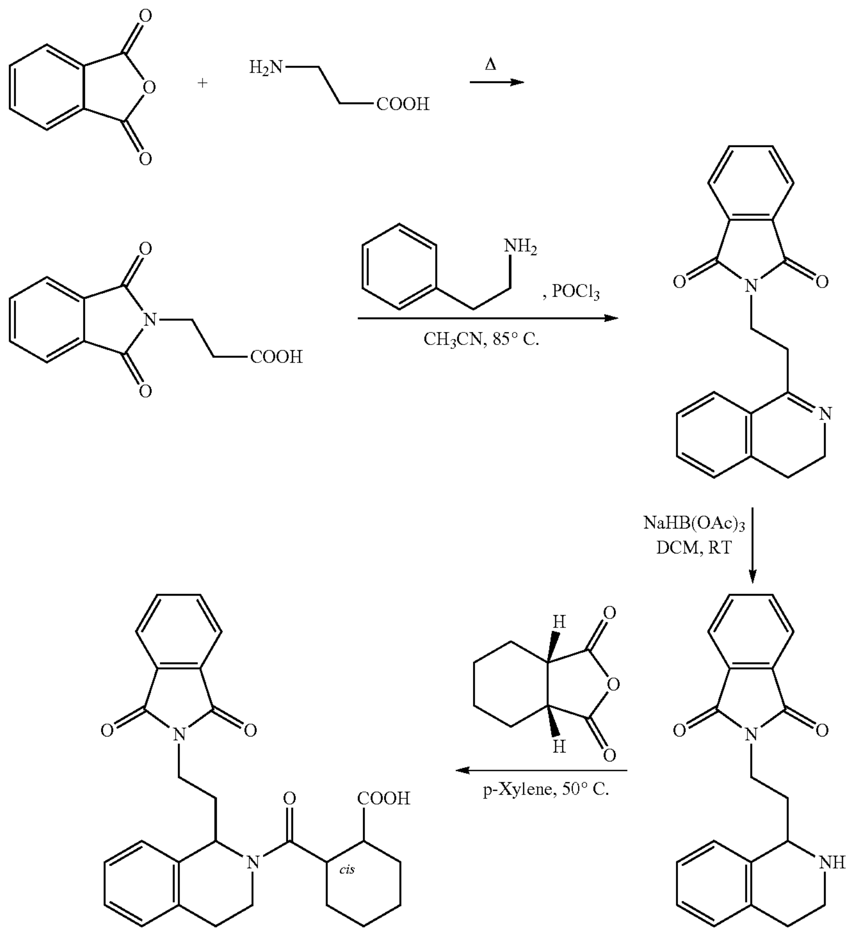

LH705

A mixture of phthalic anhydride and beta-alanine were heated to 190-200° C. in a sealed tube. Stirred for additional 30 min at 190-200° C. after the solids totally melted. The reaction mixture was cooled to room temperature and 50% EtOH/water was added. The resulted suspension was filtered and the white precipitate was further washed with 50% EtOH/water, and then dried under vacuum overnight to give the N-phthaloyl-beta-alanine. Phosphoryl chloride was added to a suspension of N-phthaloyl-beta-alanine and phenylethylamine in acetionitrile. The suspension was stirred for 6 h under reflux. Acetonitrile and phosphoryl chloride was removed by vacuum. The reaction mixture was then diluted with DCM and washed with sat $NaHCO_3$ solution, water and brine, then dried over anhydrous $Na_2SO_4$. The filtration was concentrated and the residue was purified by column chromatography using acetonitrile (0 to 20%) in DCM as eluent to afford the imine compound. Acetic acid and sodium triacetoxyborohydride were added to a solution of imine compound in DCM and stirred for 1 h at room temperature. The reaction mixture was then washed with sat $NaHCO_3$ solution, water and brine, then dried over anhydrous $Na_2SO_4$. The filtration was concentrated and the residue was purified by column chromatography using acetonitrile (0 to 50%) in DCM as eluent to give the amine compound. Cis-1,2-Cyclohexanedicarboxylic anhydride was added to a solution of amine compound in p-xylene at 50° C. and stirred for 3 h. The reaction mixture was concentrated under vacuum and the residue was purified by column chromatography using acetonitrile (0 to 20% with 1% AcOH) in DCM as eluent to give the designed product. Two diastereomers were separated by HPLC using water plus 0.1% TFA and acetonitrile plus 0.1% TFA as solvents.

Example 34

LH705AB [cis-2-((R)-1-(2-(1,3-dioxoisoindolin-2-yl)ethyl)-1,2,3,4-tetrahydroisoquinoline-2-carbonyl) cyclohexanecarboxylic acid]

LH705A

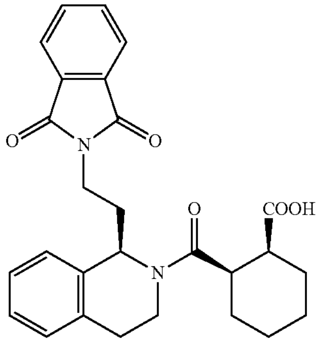

and

LH705B

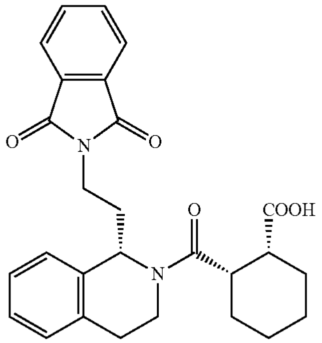

LH705AB: Prepared by following the above synthetic procedure and diastereomers were obtained by HPLC separation (mixture of 2 isomers)$^1$H-NMR (400 MHz, $CD_3OD$-$d_4$): δ 7.89-7.79 (m, 4H), 7.26-7.10 (m, 4H), 5.68 (dd, J=4, 8 Hz, 1H), 4.12-3.50 (m, 4H), 3.49-3.38 (m, 2H), 3.20-3.03 (m, 2H), 2.68-2.50 (m, 1H), 2.40-2.00 (m, 4H), 1.92-1.51 (m, 3H), 1.50-1.32 (m, 2H). MS (ESI+) m/z 461.2 (M+H).

Example 35

LH705CD [cis-2-((S)-1-(2-(1,3-dioxoisoindolin-2-yl)ethyl)-1,2,3,4-tetrahydroisoquinoline-2-carbonyl) cyclohexanecarboxylic acid]

LH705C

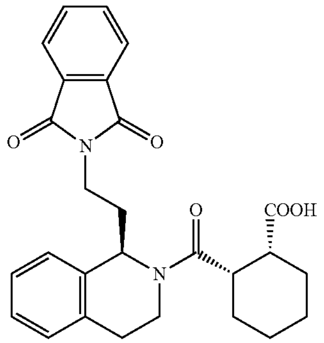

and

LH705D

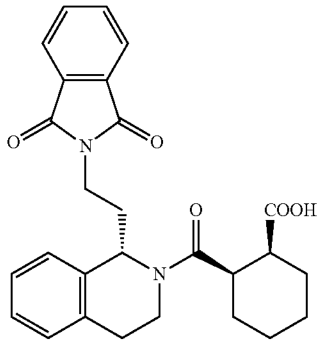

LH705CD: Prepared by following the above synthetic procedure. $^1$H-NMR (400 MHz, $CD_3OD$-$d_4$): δ 7.82-7.76 (m, 4H), 7.23-7.11 (m, 4H), 5.58 (dd, J=4, 8 Hz, 1H), 4.11-3.55 (m, 4H), 3.50-3.40 (m, 2H), 3.00-2.92 (m, 2H), 2.65-2.50 (m, 1H), 2.30-2.00 (m, 4H), 2.00-1.51 (m, 3H), 1.50-1.22 (m, 2H). MS (ESI+) m/z 461.2 (M+H).

Stereoselective Synthesis of Analogs LH601

Example 36

Scheme 20

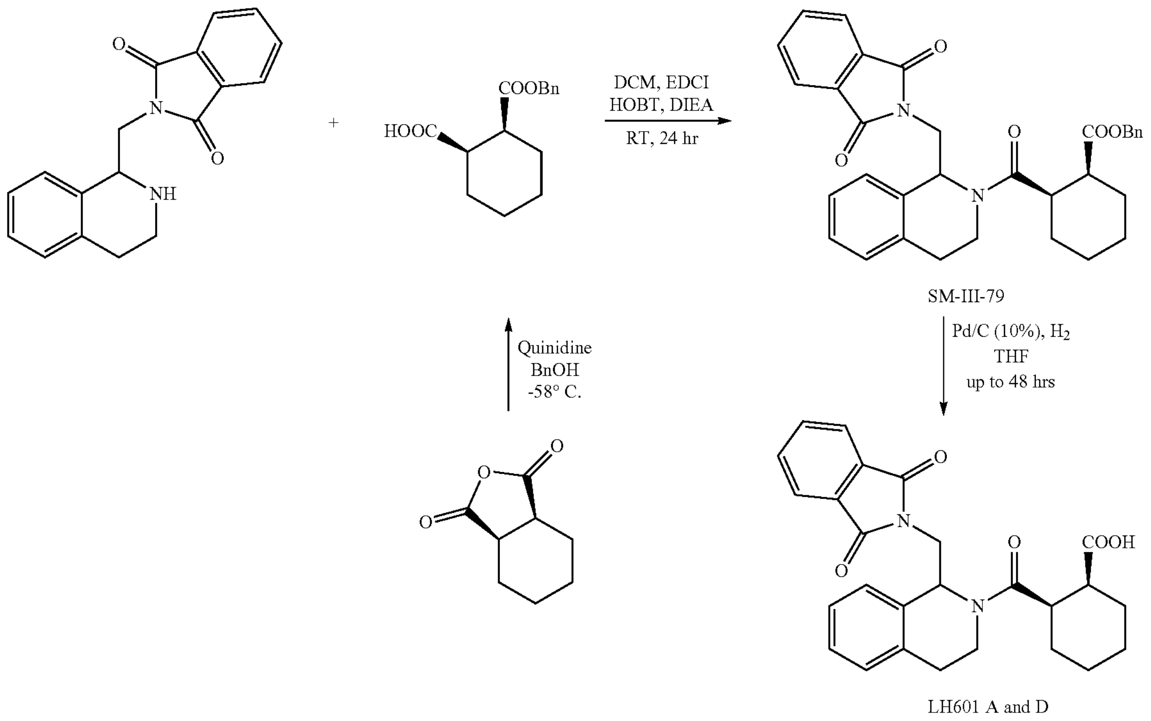

(1R,2S)-2-(benzyloxycarbonyl) cyclohexanecarboxylic acid was prepared from the meso anhydride cis-cyclohexane-dicarboxylic anhydride by reaction with benzyl alcohol at low temperature in the presence of quinidine (Christov, C.; et al., *ChemMedChem* 2011, 6, 131-140), Synthesis of SM-III-79 ((1S,2R)-benzyl 2-(1-((1,3-dioxoisoindolin-2-yl)methyl)-1,2,3,4-tetrahydroisoquinoline-2-carbonyl)cyclohexane carboxylate): (1R,2S)-2-(benzyloxycarbonyl) cyclohexanecarboxylic acid (hemi ester, 1.31 g, 5 mmol) was dissolved in DCM (50 mL) and then EDC.HCl (1.05 g, 5.5 mmol) HOBT (675 mg, 5 mmol), D1EA 1.75 mL. 10 mmol) were added. After 30 min, 1-pthalimidomethyl-1,2,3,4-tetrahydroisoquinoline (Racemic amine) in 30 mL of DCM was added slowly. The reaction mixture was stirred at RT for 24 hrs and solvent was evaporated under reduced pressure. The obtained crude was purified via column chromatography (ISCO) using Ethyl acetate (0 to 50%) in Hexane as eluent fractions were concentrated to give 1.076 g of solid (40%). Diastereomeric pairs could not be separated under these chromatographic conditions. $^1H$ NMR ($CDCl_3$, 400 MHz): δ 7.57 (m, 4H), 6.88 (m, 9H), 5.83 (dd, 1H), 4.61 (s, 1H), 3.82 (dd, 1H), 3.65 (m, 3H), 3.00 (d, 1H), 2.52 (m, 1H), 2.16 (m, 1H), 1.45 (m, 9H). MS (ESI+) m/z 537.2 (M+H).

Synthesis of SM-III-80 (LH601A and D): SM-III-79 (1.076 g) was dissolved in THF (15 mL) and 10% Pd/C (250 mg) was added, and then reaction mixture was stirred at RT under $H_2$ (atm) for 2 days. The reaction mixture was filtered through a short bed of Celite and washed with excess of MeOH. The filtrate and washings were combined and concentrated in vacuo. The obtained crude was purified via column chromatography (ISCO) using Ethyl acetate (0 to 50% with 1% AcOH) in Hexane. Diastereomeric pairs could be separated under these chromatographic conditions. 354 mg LH601 A and ~340 mg of LH 601 D were isolated. The yield was 77%.

BIOLOGICAL ASSAY

The activity of the compounds synthesized was screened using the SPR assay as we published previously (Yu Chen, L. Hu, et al., *Chem. Biol. Drug Des.* 2011, 78(6), 1014-1021.) Briefly, the concentration of the unbound Keapl Kelch domain was measured using SA chip immobilized with biotin-16mer Nrf2 peptide (300 RU) when 40 nM of Keapl Kelch domain was incubated in the presence of test compounds at two concentrations (5 μM and 50 μM) at room temperature. Each solution of Keapl Kelch domain was injected through Fc1 and Fc2 with a 1-min association time and a 3-min dissociation time at 25° C. and a flow rate of 50 μL/min. The sensor chip surface was regenerated with NaCl (1 M) at a flow rate of 100 μL/min for 1 min followed by two consecutive 1-min washes with the running buffer at a flow rate of 100 μL/min. To generate the standard curve, double subtractions from the reference surface (Fc1) and the blank were performed to the sensorgrams obtained at varying concentrations of Keapl Kelch domain. The slopes of the initial association phase from the corrected SPR sensorgrams were calculated by fitting to the linear model in BIAevaluation software 4.1 and plotted against the concentration of Keapl Kelch domain protein. The percent inhibition was then derived from the calculated concentration of the unbound Keapl Kelch domain. Representative results are shown in FIG. 8.

Figure 9:
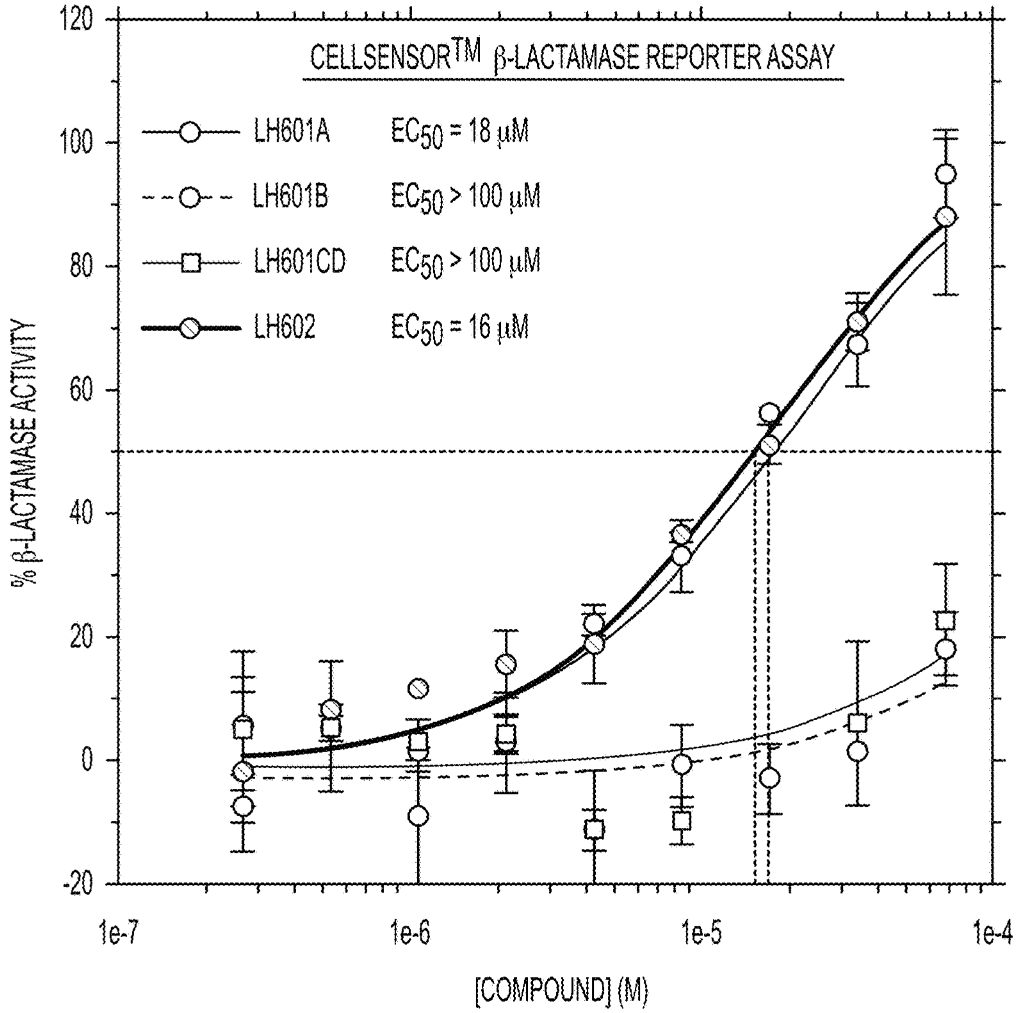
FIG. 9 illustrates ARE inducing activity of the two leads (LH601 and LH602) in CellSensor™ β-lactamase reporter assay.

Select compounds are also evaluated in cell-based ARE β-lactamase reporter assay using CellSensor HepG2 cell line. As shown in FIG. 9, both LH601A and LH602 exhibit about the same level of ARE-inducing activity in the CellSensor® ARE-bla Hep G2 cell line with an $EC_{50}$ of about 16-18 μM using 150 μM tBHQ as 100%. Consistent with our biochemical assays, LH601B and LH601C/D, the stereoisomers of LH601A, are inactive. We recently demonstrated successfully the nuclear translocation of Nrf2 upon inhibition of Keap1-Nrf2 interaction by our lead inhibitors (EC50=15 μM) using the PathHunter® nuclear translocation assay kit from DiscoveRx.

It will be understood by those skilled in the art that numerous and various modifications can be made without departing from the spirit of the present invention. Therefore, it should be clearly understood that the various embodiments of the present invention described herein are illustrative only and not intended to limit the scope of the present invention.

What is claimed is:

1. A compound of formula (Ia):

(Ia)

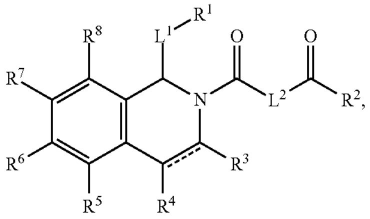

or a stereoisomer, a prodrug, or a pharmaceutically acceptable salt or solvate thereof, wherein:

“═══” is a single or double bond;

$L^1$ is $—[C(R^{10})_2]_i—$, wherein $R^{10}$ at each occurrence is independently hydrogen, halogen, $C_1$-$C_4$ alkyl, and i is 1, 2, or 3;

$L^2$ is $—[C(R^{20})_2]_j—$, $C_3$-$C_8$ cycloalkylene, $C_6$-$C_{10}$ arylene, 5- to 10-membered heteroarylene, 5- to 10-membered heterocyclylene, wherein $R^{20}$ at each occurrence is independently hydrogen, halogen, or $C_1$-$C_4$ alkyl, and j is an integer selected from 1 through 6;

$R^1$ is selected from

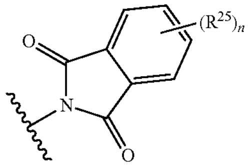

,

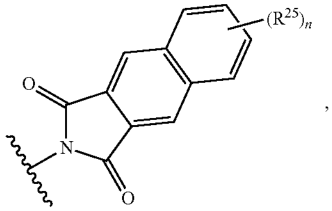

,

-continued

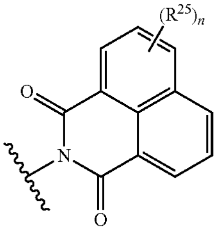

,

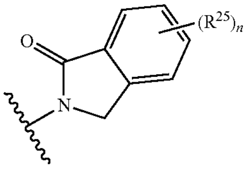

,

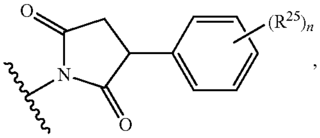

,

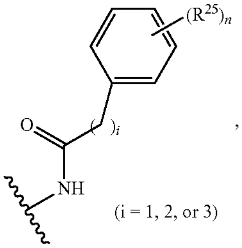

(i = 1, 2, or 3)

, and

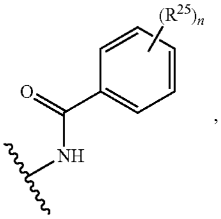

, wherein n at each occurrence is independently 0 or an integer from 1 to 4, and $R^{25}$ at each occurrence is independently hydrogen, halogen, hydroxyl, $C_1$-$C_6$ alkyl, $C_1$-$C_6$ haloalkyl, $C_1$-$C_6$ alkoxy, $C_1$-$C_6$ haloalkoxy, —CN, nitro, $—COOR^{11}$, $—CONR^aR^b$, substituted or unsubstituted $C_6$-$C_{10}$ aryl, and $—NR^aR^b$;

$R^2$ is $—OR^9$ or $—NR^aR^b$;

$R^3$ through $R^8$ are each independently hydrogen, halogen, hydroxyl, $C_1$-$C_6$ alkyl, $C_1$-$C_6$ haloalkyl, $C_1$-$C_6$ alkoxy, $C_1$-$C_6$ haloalkoxy, $C_3$-$C_8$ cycloalkyl, $C_6$-$C_{10}$ aryl, 5- to 10-membered heteroaryl, 5- to 10-membered heterocyclyl, —CN, nitro, $—COOR^{11}$, or $—NR^aR^b$;

$R^9$ at each occurrence is independently hydrogen or $C_1$-$C_6$ alkyl;

wherein any said cycloalkyl, or heterocyclyl is optionally substituted by one or more substituents independently selected from halogen, hydroxyl, $C_1$-$C_6$ alkyl, $C_1$-$C_6$ haloalkyl, $C_1$-$C_6$ alkoxy, $C_1$-$C_6$ haloalkoxy, —CN, nitro, oxo, $—COOR^{11}$, and $—NR^aR^b$;

each said aryl or heteroaryl is optionally substituted by one or more substituents independently selected from halogen, hydroxyl, $C_1$-$C_6$ alkyl, $C_1$-$C_6$ haloalkyl, $C_1$-$C_6$ alkoxy, $C_1$-$C_6$ haloalkoxy, —CN, nitro, $—COOR^{11}$, and $—NR^aR^b$;

$R^a$ and $R^b$ are each independently hydrogen or $C_1$-$C_6$ alkyl; and $R^{11}$ at each occurrence is independently hydrogen or $C_1$-$C_6$ alkyl;

provided that the compound of formula (Ia) is not

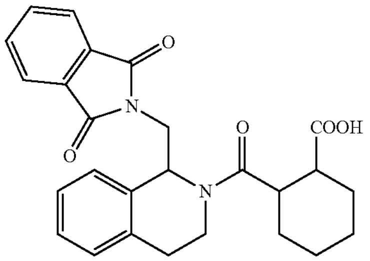 [SMILES: O=C(O)C1CCCCC1C(=O)N1CCc2ccccc2C1CN1C(=O)c2ccccc2C1=O]

or stereomers thereof.

2. The compound of claim 1, wherein:

"⚌" is a single bond;

$L^1$ is $—CH_2—$ or $—(CH_2)_2—$;

$L^2$ is $—(CH_2)_j—$ (j=1, 2, or 3), cyclohexylene, or cyclopentylene;

$R^1$ is selected from

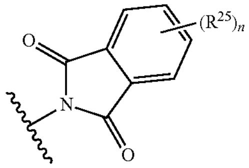

,

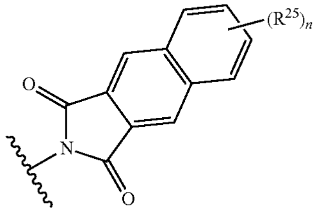

,

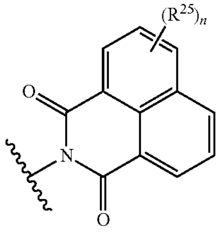

,

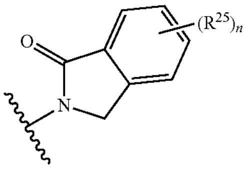

,

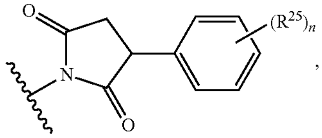

,

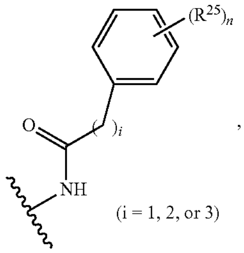

(i = 1, 2, or 3)

,

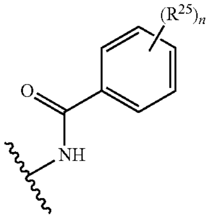

, and

-continued

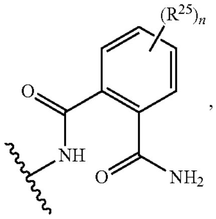

, wherein n at each occurrence is independently 0, 1, or 2; and $R^{25}$ at each occurrence is independently halogen, hydroxyl, $C_1$-$C_6$ alkyl, $C_1$-$C_6$ haloalkyl, $C_1$-$C_6$ alkoxy, $C_1$-$C_6$ haloalkoxy, —CN, nitro, $—COOR^{11}$, phenyl, and $—NR^aR^b$;

$R^2$ is $—OR^9$;

$R^3$ and $R^4$ are each hydrogen;

$R^5$ through $R^8$ are each independently hydrogen, halogen, hydroxyl, $C_1$-$C_6$ alkyl, $C_1$-$C_6$ haloalkyl, $C_1$-$C_6$ alkoxy, $C_1$-$C_6$ haloalkoxy, phenyl, or $—NR^aR^b$;

$R^9$ is hydrogen; and $R^a$ and $R^b$ are each independently hydrogen or $C_1$-$C_6$ alkyl.

3. The compound of claim 1, wherein:

"⚌" is a single bond;

$L^1$ is $—CH_2—$ or $—(CH_2)_2—$;

$L^2$ is $—(CH_2)_2—$, $—(CH_2)_3—$,

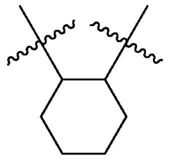

or

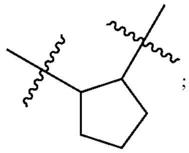

;

$R^1$ is selected from:

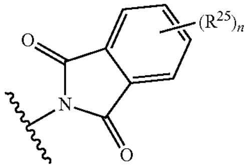

,

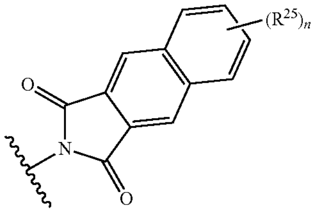

,

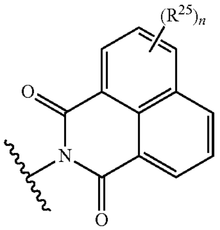

,

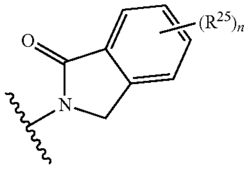

,

-continued

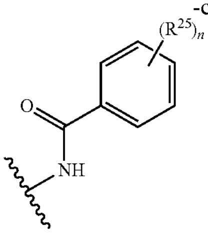

,

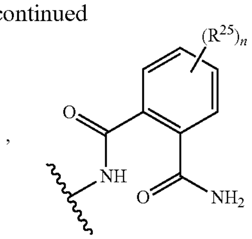

,

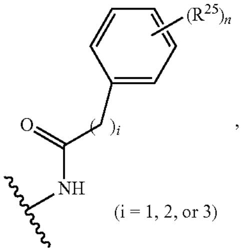

, (i = 1, 2, or 3)

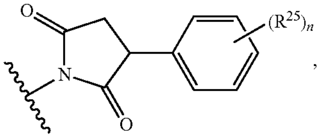

, wherein n is 0 or 1; and $R^{25}$ is selected from H, F, Cl, Br, -Ph, —$NO_2$, —$NH_2$, $C_1$-$C_4$ alkyl, and —$CO_2H$;

$R^2$ is —OH, —$OCH_3$, —$OCH_2Ph$, or —$NH_2$;

$R^3$ and $R^4$ are each hydrogen; and $R^5$ through $R^8$ are each independently hydrogen, F, Cl, Br, OMe, —$NO_2$, or —$NH_2$.

4. The compound of claim 1, wherein:

"⎓" is a single bond;

$L^1$ is —$CH_2$—;

$L^2$ is

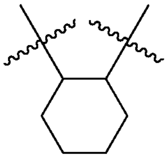

or

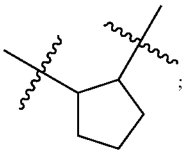

;

$R^1$ is selected from:

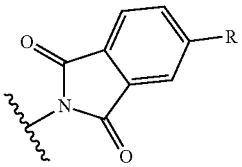

(R=H, F, Br, or -Ph),

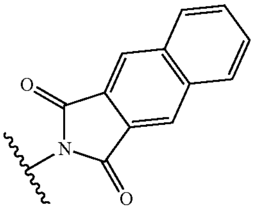

,

-continued

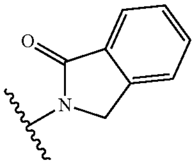

,

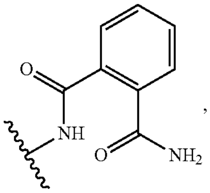

, and

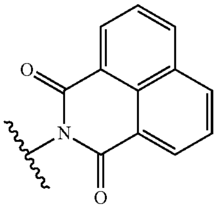

;

$R^2$ is —OH;

$R^3$ and $R^4$ are each hydrogen; and $R^5$ through $R^8$ are each independently hydrogen, F, —OMe, or —$NH_2$.

5. The compound of claim 1, selected from the group consisting of:

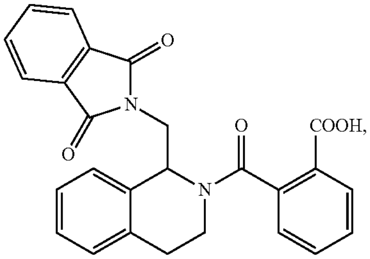

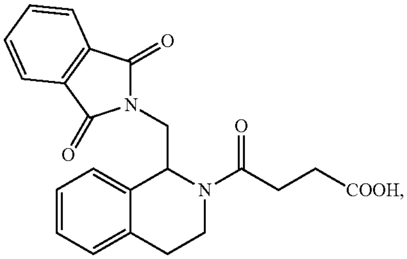

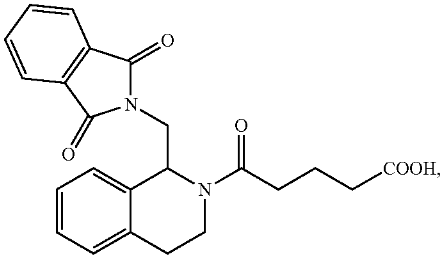

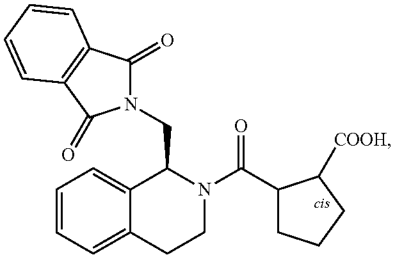

-continued
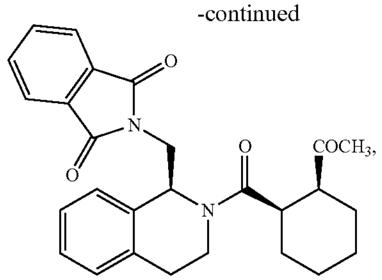
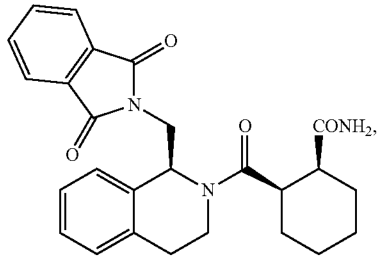
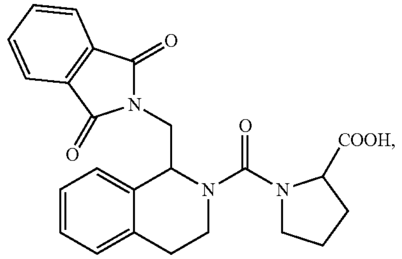
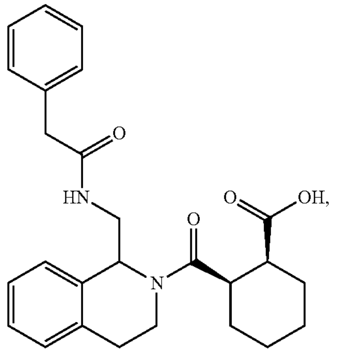
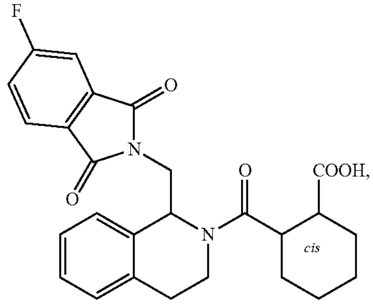
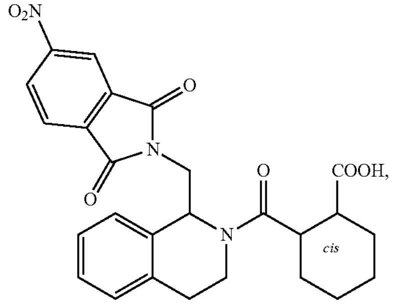
-continued
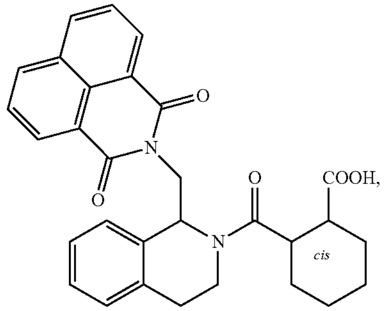
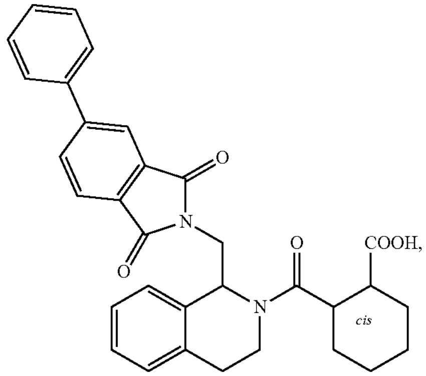
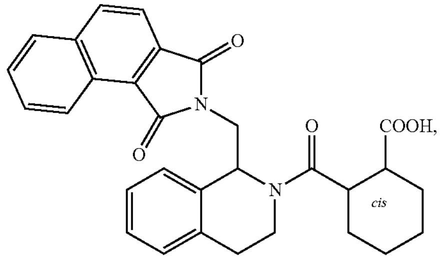
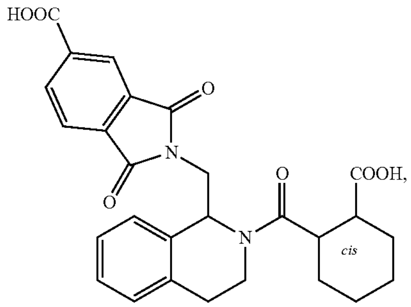
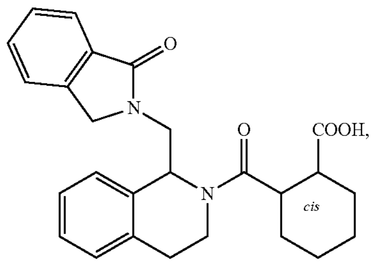

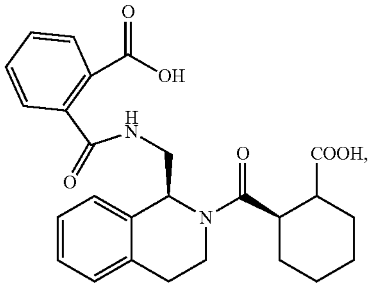
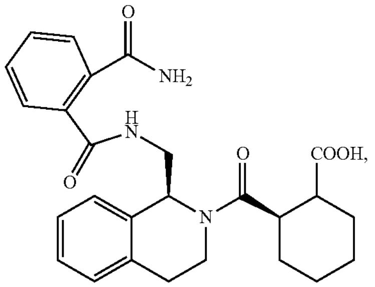
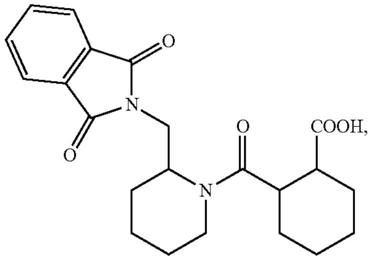
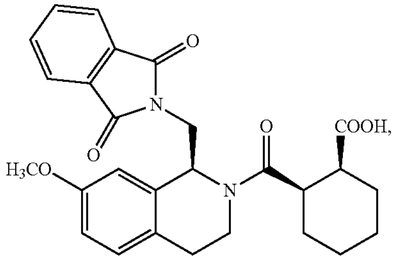
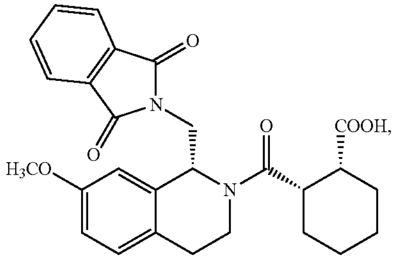
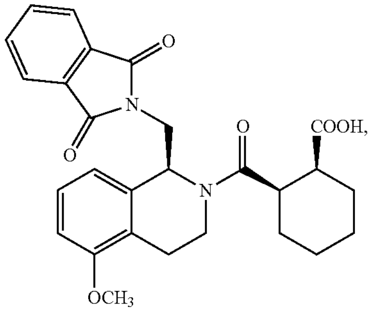
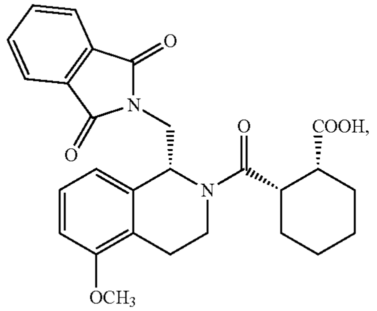
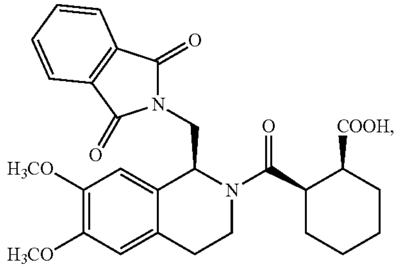
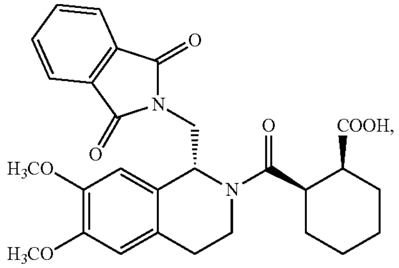
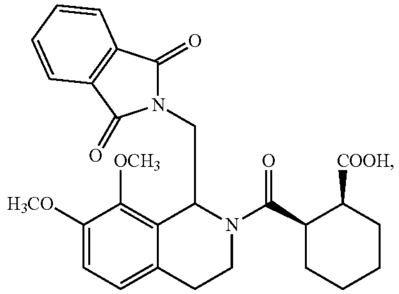
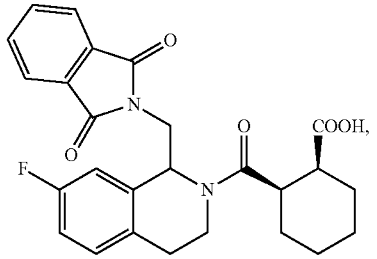
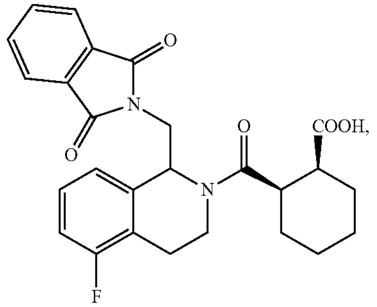

-continued
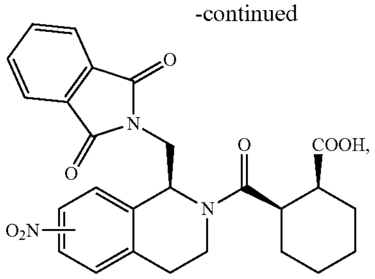
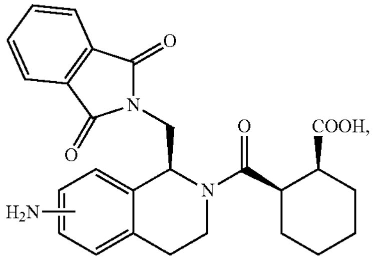
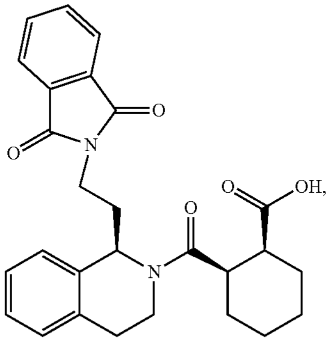
and
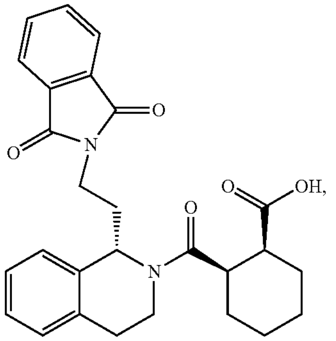
or a stereoisomer, a prodrug, or a pharmaceutically acceptable salt or solvate thereof.
6. A composition comprising a compound according to claim 1, and a pharmaceutically acceptable carrier.
7. A substantially enantiomerically pure compound selected from the group consisting of:
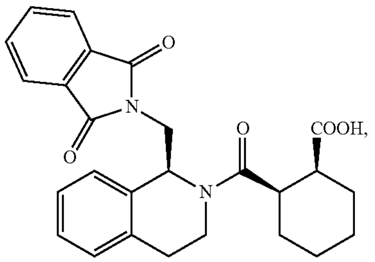
-continued
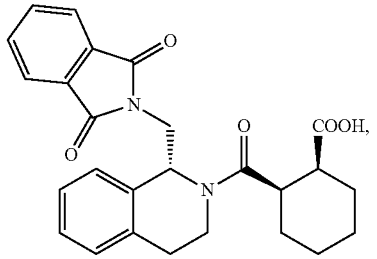
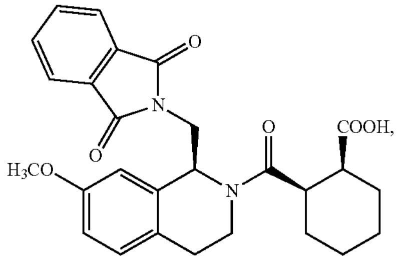
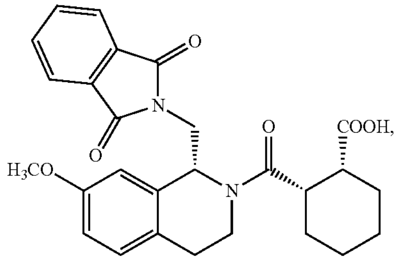
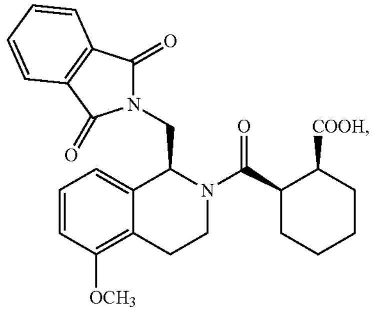
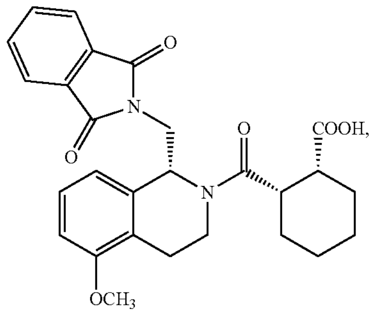
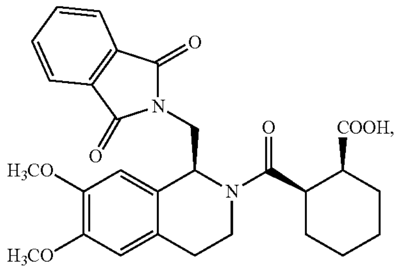
and -continued
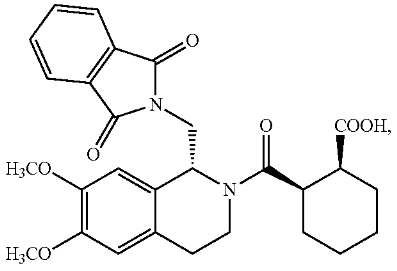
or a prodrug, a pharmaceutically acceptable salt or solvate thereof.
8. The substantially enantiomerically pure compound of claim 7, selected from:
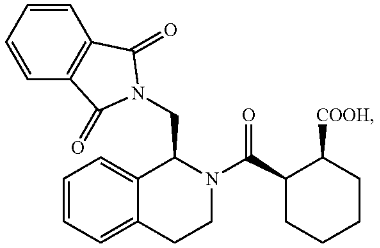
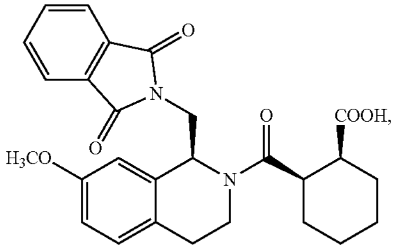
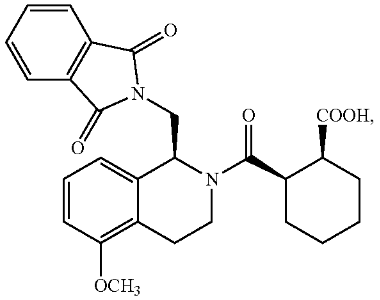
and
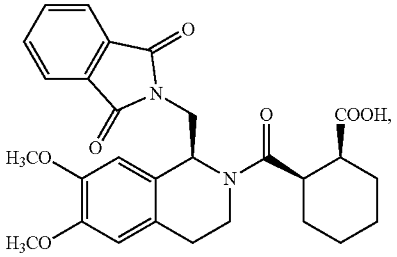
or a stereoisomer, a prodrug, or a pharmaceutically acceptable salt or solvate thereof.
9. The substantially enantiomerically pure compound of claim 7, selected from the group consisting of:
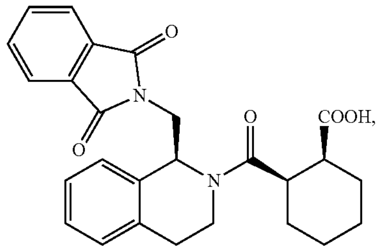
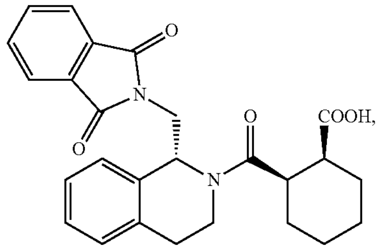
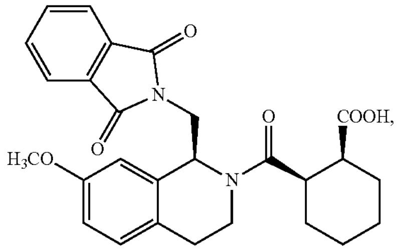
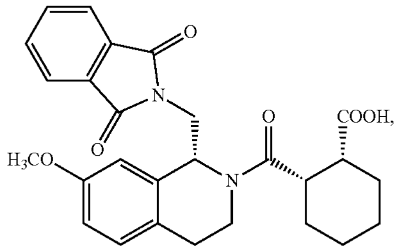
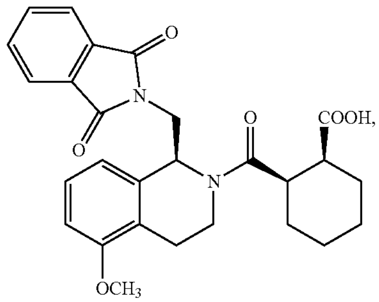
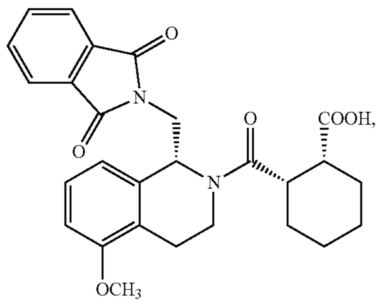

-continued

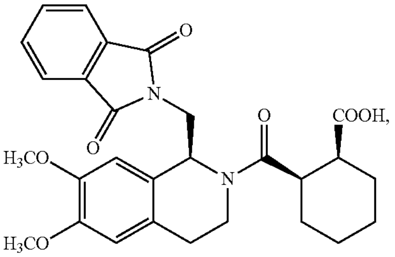

and

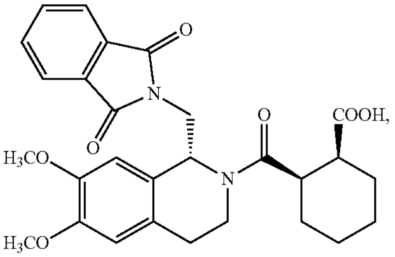

or a prodrug, a pharmaceutically acceptable salt or solvate thereof.

10. The compound of claim 1, wherein $R^1$ is

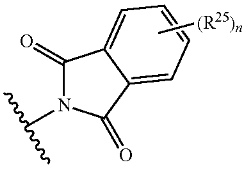

, wherein n at each occurrence is independently an integer from 1 to 4, and $R^{25}$ at each occurrence is independently halogen, hydroxyl, $C_1$-$C_6$ alkyl, $C_1$-$C_6$ haloalkyl, $C_1$-$C_6$ alkoxy, $C_1$-$C_6$ haloalkoxy, —CN, nitro, —$COOR^{11}$, —$CONR^aR^b$, substituted or unsubstituted $C_6$-$C_{10}$ aryl, and —$NR^aR^b$.

11. The compound of claim 1, wherein $R^1$ is selected from

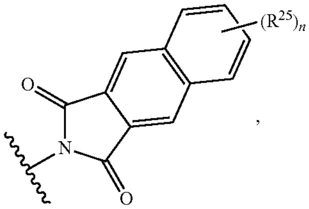

,

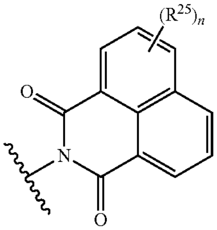

,

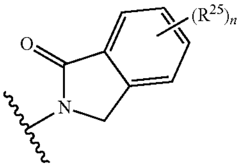

,

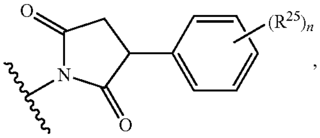

,

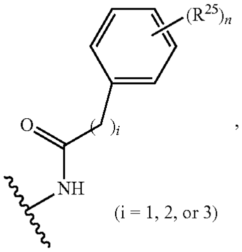

(i = 1, 2, or 3)

, and

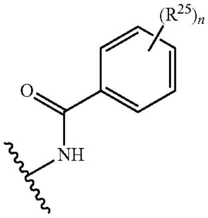

.

* * * * *

UNITED STATES PATENT AND TRADEMARK OFFICE

CERTIFICATE OF CORRECTION

PATENT NO. : 10,106,502 B2
APPLICATION NO. : 15/718987
DATED : October 23, 2018
INVENTOR(S) : Longqin Hu et al.

It is certified that error appears in the above-identified patent and that said Letters Patent is hereby corrected as shown below:

In the Specification

At Column 1, Line number 21, please amend:
The invention described herein was supported in whole or in part by grants from the National Institute of Health via Grant No. R03 MH093197 and No. R01 CA133791. The U.S. Government has certain rights in this invention.

To:
This invention was made with government support under grant numbers R03 MH093197 and R01 CA133791 awarded by the National Institutes of Health. The government has certain rights in the invention.

Signed and Sealed this
Fifth Day of April, 2022

Drew Hirshfeld
*Performing the Functions and Duties of the*
*Under Secretary of Commerce for Intellectual Property and*
*Director of the United States Patent and Trademark Office*